(12) United States Patent
Kinsho et al.

(10) Patent No.: US 8,053,165 B2
(45) Date of Patent: Nov. 8, 2011

(54) HYDROXYL-CONTAINING MONOMER, POLYMER, RESIST COMPOSITION, AND PATTERNING PROCESS

(75) Inventors: Takeshi Kinsho, Joetsu (JP); Masaki Ohashi, Joetsu (JP); Koji Hasegawa, Joetsu (JP); Takeru Watanabe, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 225 days.

(21) Appl. No.: 12/405,670

(22) Filed: Mar. 17, 2009

(65) Prior Publication Data

US 2009/0239179 A1 Sep. 24, 2009

(30) Foreign Application Priority Data

Mar. 18, 2008 (JP) .................................. 2008-069020

(51) Int. Cl.
G03F 7/038 (2006.01)
G03F 7/039 (2006.01)
G03F 7/20 (2006.01)
G03F 7/30 (2006.01)
G03F 7/38 (2006.01)

(52) U.S. Cl. ..................... 430/270.1; 430/910; 430/907; 430/325; 430/326; 430/330; 430/311; 560/205; 560/219; 560/220; 526/328; 526/320

(58) Field of Classification Search .................... None
See application file for complete search history.

(56) References Cited

U.S. PATENT DOCUMENTS

| | | |
|---|---|---|
| 3,470,124 A | 9/1969 | Van Eygen et al. |
| 5,714,625 A | 2/1998 | Hada et al. |
| 6,004,724 A | 12/1999 | Yamato et al. |
| 6,063,953 A | 5/2000 | Hada et al. |
| 6,261,738 B1 | 7/2001 | Asakura et al. |
| 6,280,898 B1 | 8/2001 | Hasegawa et al. |
| 6,312,867 B1 | 11/2001 | Kinsho et al. |
| 6,329,125 B2 | 12/2001 | Takechi et al. |
| 6,448,420 B1 | 9/2002 | Kinsho et al. |
| 6,512,020 B1 | 1/2003 | Asakura et al. |
| 6,830,866 B2 | 12/2004 | Kobayashi et al. |
| 6,916,591 B2 | 7/2005 | Ohsawa et al. |
| 6,946,233 B2 | 9/2005 | Nishi et al. |
| 7,399,577 B2 | 7/2008 | Yamato et al. |
| 2003/0054287 A1 | 3/2003 | Yasunami et al. |
| 2003/0148206 A1 | 8/2003 | Kodama |
| 2009/0023878 A1 | 1/2009 | Maeda et al. |
| 2009/0053657 A1* | 2/2009 | Hatakeyama et al. ........ 430/324 |

FOREIGN PATENT DOCUMENTS

| | | |
|---|---|---|
| EP | 1 053 986 A1 | 11/2000 |
| EP | 1300727 A2 | 4/2003 |
| EP | 1300727 A3 | 10/2003 |
| JP | 9-90637 A | 4/1997 |
| JP | 9-095479 A | 4/1997 |
| JP | 9-208554 A | 8/1997 |
| JP | 9-230588 A | 9/1997 |
| JP | 9-301948 A | 11/1997 |
| JP | 2906999 B2 | 4/1999 |
| JP | 2000-26446 A | 1/2000 |
| JP | 2000-159758 A | 6/2000 |
| JP | 2000-314956 A | 11/2000 |
| JP | 2000-327633 A | 11/2000 |
| JP | 2000-336121 A | 12/2000 |
| JP | 2003-66596 A | 3/2003 |
| JP | 2003-66612 A | 3/2003 |
| JP | 2003-113213 A | 4/2003 |
| JP | 2003-114522 A | 4/2003 |
| JP | 2004-86020 A | 3/2004 |
| JP | 2004-219822 A | 8/2004 |
| WO | WO-2004/074242 A2 | 9/2004 |

OTHER PUBLICATIONS

Arimitsu et at., "Sensitivity Enhancement of Chemical-Amplification-Type Photoimaging Materials by Acetoacetic Acid Derivatives", Journal of Photopolymer Science and Technology, vol. 8, No. 1, 1995, pp. 43-44.
Judo et al., "Enhancement of the Sensitivity of Chemical-Amplification-Type Photoimaging Materials by β-Tosyloxyketone Acetals", Journal of Photopolymer Science and Technology, vol. 8, No. 1, 1995, pp. 45-46.
Arimitsu et al., "Effect of Phenolic Hydroxyl Residues on the Improvement of Acid-Proliferation-Type Photoimaging Materials", Journal of Photopolymer Science and Technology, vol. 9, No. 1, 1996, pp. 29-30.
Maenhoudt et al., "Double Patterning scheme for sub-0.25 k1 single damascene structures at NA=0.75, λ=193nm", Proceedings of SPIE, vol. 5754, 2005, p. 1508.
Shibuya et al., "Performance of Resolution Enhancement Technique Using Both Multiple Exposure and Nonlinear Resist", Japan Journal of Applied Physics, vol. 33, 1994, Part 1, No. 12B, pp. 6874-6877.
Japanese Office Action issued Jun. 21, 2010, in Japanese Application JP-2008-069020.
EPO European Search Report, Appl. No. 09003777.1, Dec. 10, 2010, pp. 1-5.

* cited by examiner

Primary Examiner — Sin J. Lee
(74) Attorney, Agent, or Firm — Birch, Stewart, Kolasch & Birch, LLP

(57) ABSTRACT

A hydroxyl-containing monomer of formula (1) is provided wherein $R^1$ is H, F, methyl or trifluoromethyl, $R^2$ and $R^3$ are monovalent $C_1$-$C_{15}$ hydrocarbon groups, or $R^2$ and $R^3$ may form an aliphatic ring. The monomers are useful for the synthesis of polymers which have high transparency to radiation of up to 500 nm and the effect of controlling acid diffusion so that the polymers may be used as a base resin to formulate radiation-sensitive resist compositions having a high resolution.

(1)

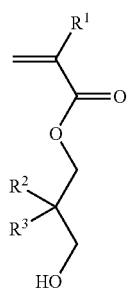

10 Claims, No Drawings

HYDROXYL-CONTAINING MONOMER, POLYMER, RESIST COMPOSITION, AND PATTERNING PROCESS

CROSS-REFERENCE TO RELATED APPLICATION

This non-provisional application claims priority under 35 U.S.C. §119(a) on Patent Application No. 2008-069020 filed in Japan on Mar. 18, 2008, the entire contents of which are hereby incorporated by reference.

TECHNICAL FIELD

This invention relates to novel hydroxyl-containing monomers useful as reactants for the synthesis of functional materials. The monomers are useful in preparing polymers which are used as a base resin to formulate a radiation-sensitive resist composition having high transparency to radiation with a wavelength of up to 500 nm, especially up to 300 nm, e.g., KrF laser, ArF laser or $F_2$ laser light as well as good development characteristics. The invention also relates to polymers comprising recurring units derived from the hydroxyl-containing monomers, photoresist compositions comprising the polymers, and pattern forming processes using the photoresist compositions.

BACKGROUND ART

While a number of recent efforts are being made to achieve a finer pattern rule in the drive for higher integration and operating speeds in LSI devices, deep-ultraviolet lithography is thought to hold particular promise as the next generation in microfabrication technology. In particular, photolithography using a KrF, ArF or $F_2$ laser as the light source is strongly desired to reach the practical level as the micropatterning technique capable of achieving a feature size of 0.3 μm or less. In these lithography processes, resist materials comprising various alkali-soluble resins as the base resin are used.

For resist materials for use in the KrF laser lithography, in fact, polyhydroxystyrene resins become the standard. For ArF resist materials, studies are made on poly(meth)acrylate resins utilizing carboxyl groups as the alkali soluble group and polymers of cycloaliphatic olefins such as norbornene. Of these, poly(meth)acrylate resins are practically used because of ease of polymerization.

As for the poly(meth)acrylate, JP-A 9-90637 proposes a combination of methyladamantyl(meth)acrylate as acid labile group-containing recurring units with lactone ring-containing (meth)acrylate as adhesive group-containing recurring units. JP-A 2000-327633 discloses an acid labile group having an exo-isomer of a tertiary alkyl group of alkylbicyclo[2.2.1]heptanol form. This acid labile group is easily acid eliminatable, requires only low activation energy for acid elimination, and provides for a high resolution and less dependence on post-exposure baking (PEB). As the adhesive groups with enhanced etching resistance, JP-A 2000-26446 and JP-A 2000-159758 propose (meth)acrylate units having norbornane-lactone and oxanorbornane-lactone, respectively. These works resulted in ArF resist materials having significantly improved resolution. Also, JP-A 2003-113213 discloses a ternary polymer comprising acid labile group units, lactone units, and hydroxyl-containing recurring units as derived from 3-hydroxy-1-adamantyl(meth)acrylate, for controlling the diffusion within a resist film of the acid generated by the photoacid generator upon exposure. This polymer is also useful as a base resin in resist materials.

While the control of acid diffusion within resist film is indispensable to maintain various process margins, typically exposure latitude (EL) and mask error enhancement factor (MEEF), and to establish high resolution resists, the 3-hydroxy-1-adamantyl(meth)acrylate units have the drawbacks of lower resist sensitivity and pattern collapse due to excessive swelling. There is a desire to have novel acid diffusion control units.

Citation List

Patent Document 1: JP-A H09-90637

Patent Document 2: JP-A 2000-327633 (U.S. Pat. No. 6,448,420, EP 1053986B1)

Patent Document 3: JP-A 2000-26446

Patent Document 4: JP-A 2000-159758 (U.S. Pat. No. 6,280,898)

Patent Document 5: JP-A 2003-113213

SUMMARY OF INVENTION

The invention aims to establish a resist composition which features controlled acid diffusion a high resolution and an increased process margin, when processed by photolithography using high-energy radiation such as ArF excimer laser light as the light source. An object of the invention is to provide a hydroxyl-containing monomer which is useful in forming a polymer as the base resin, a polymer derived from the hydroxyl-containing monomer, a resist composition comprising the polymer as the base resin, and a pattern forming process using the same.

The inventors have found that a hydroxyl-containing monomer having the general formula (1) can be readily prepared, that a polymer obtained from this monomer is a useful base resin to formulate a resist composition, and that the resist composition has the significant effect of controlling acid diffusion and is advantageously used in precise micropatterning.

The invention provides a hydroxyl-containing monomer, polymer, resist composition, and pattern forming process, as defined below.

A first embodiment of the invention is a hydroxyl-containing monomer having the general formula (1).

(1)

Herein $R^1$ is hydrogen, fluorine, methyl or trifluoromethyl, $R^2$ and $R^3$ are each independently a monovalent, straight, branched or cyclic hydrocarbon group having 1 to 15 carbon atoms, or $R^2$ and $R^3$ may bond together to form an aliphatic hydrocarbon ring with the carbon atom to which they are attached. Preferably, the aliphatic hydrocarbon ring that $R^2$ and $R^3$ form is a bridged hydrocarbon ring.

A second embodiment of the invention is a polymer comprising recurring units derived from the hydroxyl-containing monomer of the first embodiment. The recurring units have the general formula (1a).

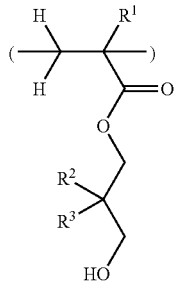

(1a)

Herein $R^1$, $R^2$ and $R^3$ are as defined above.

A third embodiment of the invention is a resist composition comprising the polymer of the second embodiment as a base resin.

A fourth embodiment of the invention is a process for forming a pattern, comprising the steps of applying the resist composition of the third embodiment onto a substrate, heat treating, exposing to high-energy radiation or electron beam through a photomask, optionally heat treating, and developing with a developer.

ADVANTAGEOUS EFFECT OF INVENTION

The hydroxyl-containing monomers of the invention are useful as reactants for the synthesis of functional materials, typically polymers which have high transparency to radiation with a wavelength of up to 500 nm, especially up to 300 nm, and the effect of controlling acid diffusion so that the polymers may be used as a base resin to formulate a radiation-sensitive resist composition having a high resolution. The polymers are useful base resins in radiation-sensitive resist compositions.

DESCRIPTION OF EMBODIMENTS

As used herein, the singular forms "a," "an" and "the" include plural referents unless the context clearly dictates otherwise. The notation (Cn-Cm) means a group containing from n to m carbon atoms per group. The term "monomer" refers to a polymerizable compound.

It is understood that for many structures represented by chemical formulae, there can exist enantiomers and diastereomers. Unless otherwise stated, a single formula collectively represents all such stereoisomers. The stereoisomers may be used alone or in admixture.

Monomer

The hydroxyl-containing monomers of the invention have the general formula (1).

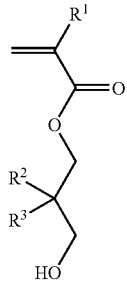

(1)

Herein $R^1$ is a hydrogen atom, fluorine atom, methyl group or trifluoromethyl group. $R^2$ and $R^3$ are each independently a monovalent, straight, branched or cyclic hydrocarbon group having 1 to 15 carbon atoms, preferably 1 to 8 carbon atoms, or $R^2$ and $R^3$ may bond together to form an aliphatic hydrocarbon ring with the carbon atom to which they are attached.

Examples of suitable monovalent, straight, branched or cyclic $C_1$-$C_{15}$ hydrocarbon groups represented by $R^2$ and $R^3$ include, but are not limited to, methyl, ethyl, propyl, isopropyl, n-butyl, sec-butyl, tert-butyl, tert-amyl, n-pentyl, n-hexyl, n-heptyl, n-octyl, n-nonyl, n-decyl, cyclopropyl, cyclobutyl, cyclopentyl, cyclopentylmethyl, cyclopentylethyl, cyclopentylbutyl, cyclohexyl, cyclohexylmethyl, cyclohexylethyl, cyclohexylbutyl, methylcyclohexylmethyl, ethylcyclohexylmethyl, ethylcyclohexylethyl, bicyclo[2.2.1]heptyl, bicyclo[2.2.1]heptylmethyl, bicyclo[2.2.1]heptylethyl, bicyclo[2.2.1]heptylbutyl, methylbicyclo[2.2.1]heptylmethyl, ethylbicyclo[2.2.1]heptylmethyl, ethylbicyclo[2.2.1]heptylethyl, bicyclo[2.2.2]octyl, bicyclo[2.2.2]octylmethyl, bicyclo[2.2.2]octylethyl, bicyclo[2.2.2]octylbutyl, methylbicyclo[2.2.2]octylmethyl, ethylbicyclo[2.2.2]octylmethyl, ethylbicyclo[2.2.2]octylethyl, tricyclo[5.2.1.0$^{2,6}$]decyl, tricyclo[5.2.1.0$^{2,6}$]decylmethyl, tricyclo[5.2.1.0$^{2,6}$]decylethyl, tricyclo[5.2.1.0$^{2,6}$]decylbutyl, methyltricyclo[5.2.1.0$^{2,6}$]decylmethyl, ethyltricyclo[5.2.1.0$^{2,6}$]decylmethyl, ethyltricyclo[5.2.1.0$^{2,6}$]decylethyl, adamantyl, adamantylmethyl, adamantylethyl, adamantylbutyl, methyladamantylmethyl, ethyladamantylmethyl, ethyladamantylethyl, tetracyclo[4.4.0.1$^{2,5}$.1$^{7,10}$]dodecyl, tetracyclo[4.4.0.1$^{2,5}$.1$^{7,10}$]dodecylmethyl, tetracyclo[4.4.0.1$^{2,5}$.1$^{7,10}$] dodecylethyl, tetracyclo[4.4.0.1$^{2,5}$.1$^{7,10}$] dodecylbutyl, tetracyclo[4.4.0.1$^{2,5}$.1$^{7,10}$]dodecylmethyl, ethyltetracyclo[4.4.0.1$^{2,5}$.1$^{7,10}$]dodecylmethyl, ethyltetracyclo[4.4.0.1$^{2,5}$.1$^{7,10}$]dodecylethyl, phenyl, tolyl and naphthyl. These groups may contain an unsaturated bond. Of these monovalent hydrocarbon groups, methyl, ethyl, propyl, isopropyl and n-butyl are preferred.

Alternatively, $R^2$ and $R^3$ may bond together to form an aliphatic hydrocarbon ring with the carbon atom to which they are attached. Suitable aliphatic hydrocarbon rings include $C_3$-$C_{12}$ aliphatic hydrocarbons such as cyclopropane, cyclobutane, cyclopentane, cyclohexane, bicyclo[2.2.1]heptane, bicyclo[2.2.2]octane, tricyclo[5.2.1.0$^{2,6}$]decane, adamantane, and tetracyclo[4.4.0.1$^{2,5}$.1$^{7,10}$]dodecane, as well as fused rings containing at least one of the foregoing, and substituted forms of the foregoing in which some hydrogen atoms are replaced by straight, branched or cyclic monovalent hydrocarbon groups. The foregoing groups may contain an unsaturated bond. Of these aliphatic hydrocarbon rings, cyclopentane, cyclohexane, bicyclo[2.2.1]heptane, bicyclo[2.2.2]octane, tricyclo[5.2.1.0$^{2,6}$]decane, and adamantane are preferred, and bridged hydrocarbon rings such as bicyclo

[2.2.1]heptane, bicyclo[2.2.2]octane, tricyclo[5.2.1.0$^{2,6}$]decane, and adamantane are more preferred.

Illustrative, non-limiting examples of the hydroxyl-containing monomers of the invention are given below.

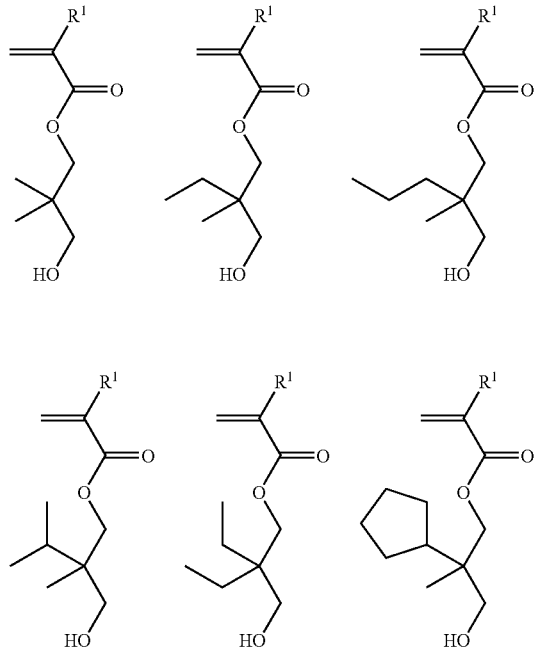

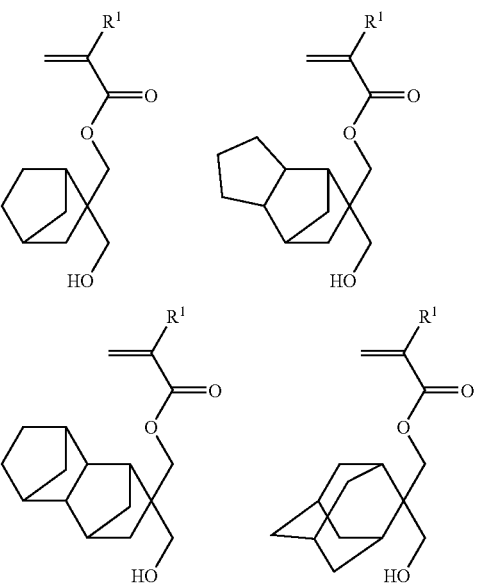

Note that R$^1$ is as defined above.

The method for preparing the hydroxyl-containing monomers of the invention may be by (mono)acylation of a diol compound having the following general formula (2).

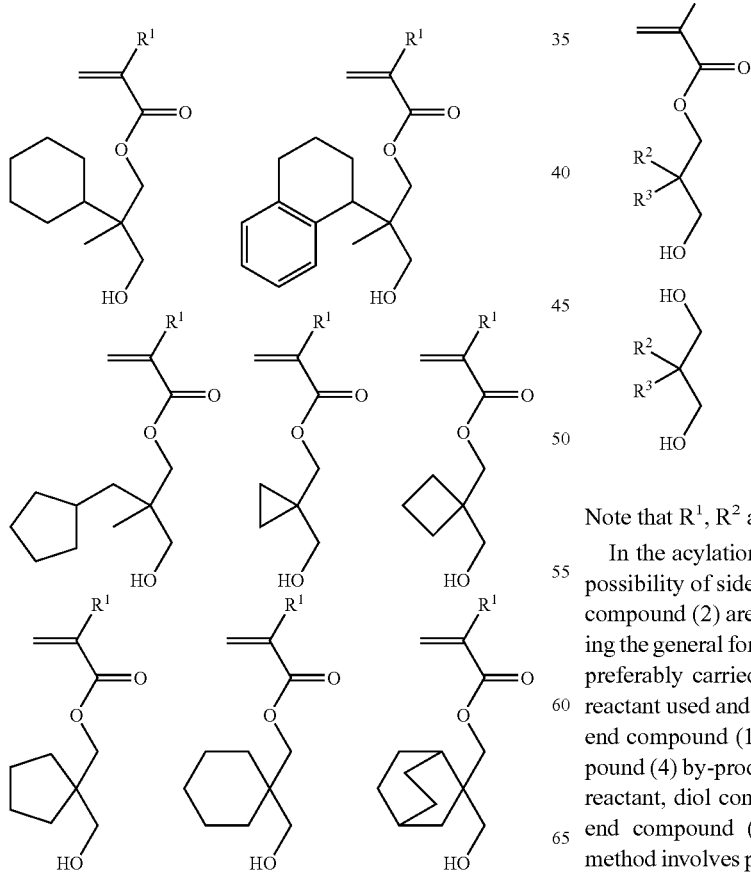

Note that R$^1$, R$^2$ and R$^3$ are as defined above.

In the acylation reaction of diol compound (2), there is a possibility of side reaction that both hydroxyl groups of diol compound (2) are acylated to form a diester compound having the general formula (4), shown below. Thus the reaction is preferably carried out while controlling the amount of the reactant used and reaction conditions, so that a proportion of end compound (1) becomes predominant. The diester compound (4) by-produced may be converted back to the starting reactant, diol compound (2) by hydrolysis or the like, or to end compound (1) by partial hydrolysis. An alternative method involves previously protecting one hydroxyl group of the diol compound with a protective group, acylating the compound, and deprotecting the protective group to convert the acylated compound into end compound (1).

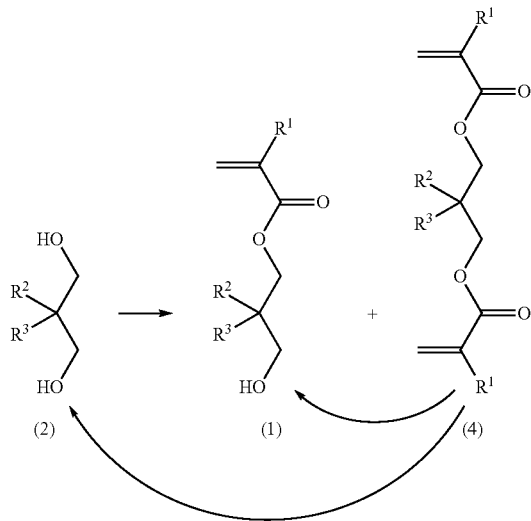

Note that $R^1$, $R^2$ and $R^3$ are as defined above.

For the acylation reaction, any well-known procedures for ester production including reaction with acylating agents, reaction with carboxylic acid, and ester exchange reaction may be applied. As for the reaction with acylating agents, the starting diol compound (2), an acylating agent, and a base are successively or simultaneously added to a solvent whereupon reaction takes place. Exemplary solvents include chlorine-based solvents such as methylene chloride, chloroform and trichloroethylene, hydrocarbons such as hexane, heptane, benzene, toluene, xylene and cumene, ethers such as dibutyl ether, diethylene glycol diethyl ether, diethylene glycol dimethyl ether, tetrahydrofuran, and 1,4-dioxane, nitriles such as acetonitrile, ketones such as acetone and 2-butanone, esters such as ethyl acetate and n-butyl acetate, and aprotic polar solvents such as N,N-dimethylformamide, dimethyl sulfoxide and hexamethylphosphoric triamide, and mixtures comprising two or more thereof. Exemplary acylating agents include acid halides such as acrylic chloride, methacrylic chloride, acrylic bromide, methacrylic bromide, and α-trifluoromethylacrylic chloride, and acid anhydrides such as acrylic anhydride, methacrylic anhydride, α-trifluoromethylacrylic anhydride, mixed acrylic/trifluoroacetic anhydride, mixed methacrylic/trifluoroacetic anhydride, mixed α-trifluoromethylacrylic/trifluoroacetic anhydride, mixed acrylic/pivalic anhydride, mixed methacrylic/pivalic anhydride, α-trifluoromethylacrylic/pivalic anhydride, mixed acrylic/p-nitrobenzoic anhydride, mixed methacrylic/p-nitrobenzoic anhydride, mixed ethyl acrylate/carbonic anhydride, mixed ethyl methacrylate/carbonic anhydride, acrylic acid/p-nitrophenyl, methacrylic acid/p-nitrophenyl, and α-trifluoromethylacrylic acid/p-nitrophenyl. Exemplary bases include triethylamine, diisopropylethylamine, N,N-dimethylaniline, pyridine, and 4-dimethylaminopyridine. When acid anhydrides are used as the acylating agent, the reaction may be carried out in the presence of an acid catalyst instead of the base, the acid catalyst being selected from mineral acids such as hydrochloric acid, hydrobromic acid, sulfuric acid and nitric acid and organic acids such as oxalic acid, trifluoroacetic acid, methanesulfonic acid, benzenesulfonic acid, and p-toluenesulfonic acid. For the acylation reaction, an appropriate reaction temperature may be selected in accordance with the type of acylating agent and reaction conditions. The reaction temperature generally ranges from −50° C. to around the boiling point of the solvent, and preferably from −20° C. to room temperature. The amount of acylating agent used varies depending on its structure and is usually 1 to 40 moles, and preferably 1 to 5 moles per mole of diol compound (2).

The reaction with carboxylic acid is dehydration reaction between a corresponding carboxylic acid (i.e., acrylic acid, methacrylic acid, or α-trifluoromethylacrylic acid) and the starting diol compound (2), which is generally carried out in the presence of an acid catalyst. The amount of carboxylic acid used varies depending on its structure and is usually 1 to 40 moles, and preferably 1 to 5 moles per mole of diol compound (2). Suitable acid catalysts include mineral acids such as hydrochloric acid, hydrobromic acid, sulfuric acid and nitric acid and organic acids such as oxalic acid, trifluoroacetic acid, methanesulfonic acid, benzenesulfonic acid, and p-toluenesulfonic acid, which may be used alone or in admixture. The acid catalyst may be used in an amount of 0.001 to 1 mole, and preferably 0.01 to 0.05 mole per mole of diol compound (2). The solvent may be the same as exemplified for the reaction with esterifying agents. Often, the reaction temperature preferably ranges from −50° C. to around the boiling point of the solvent. It is acceptable to carry out the reaction in a solvent containing a hydrocarbon such as hexane, heptane, benzene, toluene, xylene or cumene while azeotroping off the water generated during the reaction. In this embodiment, water may be distilled off while refluxing at the boiling point of the solvent under atmospheric pressure. Water may also be distilled off at a temperature below the boiling point under vacuum.

As for the ester exchange reaction, an ester of a corresponding carboxylic acid (i.e., acrylate, methacrylate or α-trifluoromethylacrylate) and the starting diol compound (2) are reacted in the presence of a catalyst while the alcohol generated during the reaction is removed from the system. The carboxylates used herein are preferably primary alkyl esters, of which methyl, ethyl and n-propyl esters are preferred for cost and fast progress of reaction. The amount of carboxylate used varies depending on its structure and is usually 1 to 40 moles, and preferably 1 to 5 moles per mole of diol compound (2). Suitable catalysts include mineral acids such as hydrochloric acid, hydrobromic acid, sulfuric acid and nitric acid; organic acids such as oxalic acid, trifluoroacetic acid, methanesulfonic acid, benzenesulfonic acid, and p-toluenesulfonic acid; bases such as sodium methoxide, sodium ethoxide, potassium t-butoxide, and 4-dimethylaminopyridine; salts such as sodium cyanide, potassium cyanide, sodium acetate, potassium acetate, calcium acetate, tin acetate, aluminum acetate, aluminum acetoacetate, and alumina; and Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium(IV) oxide, which may be used alone or in admixture. The catalyst may be used in an amount of 0.001 to 20 moles, and preferably 0.01 to 0.05 mole per mole of diol compound (2). The reaction may be carried out in a solventless system (one reactant, carboxylate itself may serve as the solvent), which is preferred because extra steps such as concentration and solvent recovery are unnecessary. In certain cases, however, a solvent may be used in an auxiliary manner for the purposes of preventing the end compound or reactants from polymerization. The solvent used herein is preferably selected from hydrocarbons such as hexane, heptane, benzene, toluene, xylene and cumene, and ethers such as dibutyl ether, diethylene glycol diethyl ether, diethylene glycol dimethyl ether, tetrahydrofuran and 1,4-dioxane, alone or in admixture. An appropriate reaction temperature may be selected in accordance with the type of carboxylate used and reaction conditions. The reaction is often carried out at an elevated temperature, typically near the boiling point of a low-boiling alcohol resulting from ester exchange reaction, such as methanol, ethanol or 1-propanol while distilling off the alcohol being generated. The alcohol may be distilled off at a temperature below the boiling point under vacuum.

Where the reactant to be acylated, diol compound (2) is not commercially available, it may be synthesized by a variety of methods, for example, (A) reduction of 2,2-disubstituted malonic acid or its ester, and (B) reaction of an aldehyde of the general formula (3) with formaldehyde in the presence of a base, known as Tollens reaction. Method (A) is advantageous in that various alkyl groups can be introduced as $R^2$ and $R^3$. Method (B) is effective when a corresponding aldehyde is available or may be readily derived from another derivative, and preferable particularly when the aliphatic hydrocarbon ring that $R^2$ and $R^3$ form together with the carbon atom to which they are attached is a bridged hydrocarbon ring.

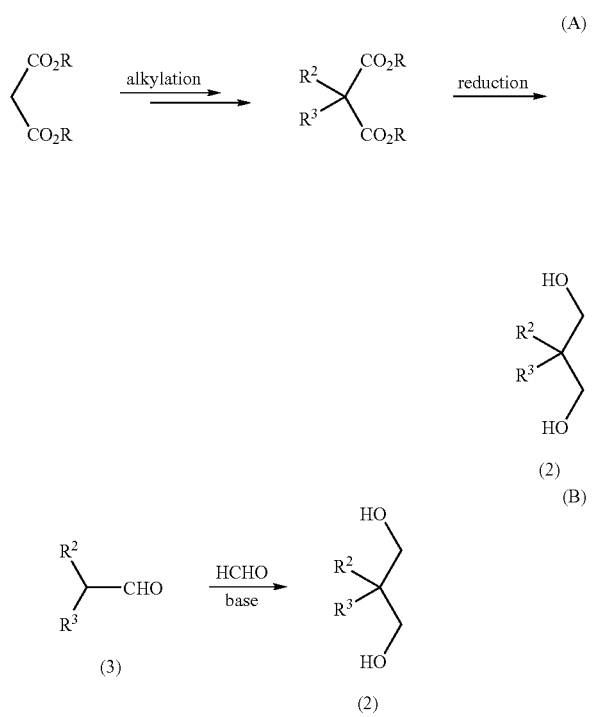

Note that $R^2$ and $R^3$ are as defined above, and R is alkyl or hydrogen.

The monomer and any synthesis intermediate thereof may be purified prior to use by any standard techniques including distillation, crystallization, recrystallization, and chromatography.

Next, the design concept of the hydroxyl-containing monomer is described. The hydroxyl-containing monomer is a useful monomer from which recurring units (1a) of a polymer to be described later are derived, which polymer is used as a base resin in a radiation-sensitive resist composition to be described later.

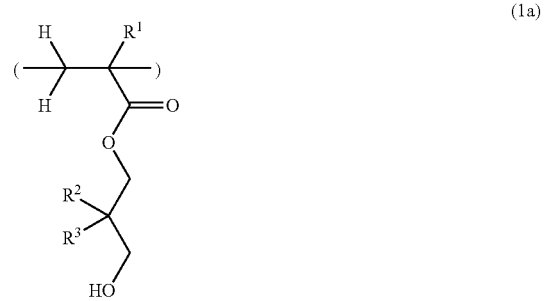

(1a)

Note that $R^1$, $R^2$ and $R^3$ are as defined above.

While a photoacid generator in a resist composition generates an acid upon exposure, a free hydroxyl group has affinity to the proton ($H^+$) of this acid due to interaction thereof with a lone pair on the oxygen atom. It is believed that this exerts the function of controlling acid diffusion. In recurring units (1a), the carbon atom (β-carbon) adjoining the carbon atom (α-carbon) to which the hydroxyl group is attached is a tertiary carbon owing to substitution of $R^2$ and $R^3$ thereon. Absent a hydrogen atom (β-hydrogen) on this β-carbon, it never happens that the hydroxyl group is lost by elimination of water. Since this β-carbon is also regarded as β-carbon when viewed from the ester linked to the polymer backbone, it never happens that acid catalyzed elimination reaction occurs to create carboxylic acid. It is thus believed that the hydroxyl group's effect on the movement of proton in the polymer matrix is not impaired. It is also believed that since the position of hydroxyl group is at a distance from the polymer backbone, the hydroxyl group has a proper mobility.

In addition, substituents $R^2$ and $R^3$ on β-carbon may be selected from a wide variety of groups, affording an increased freedom of molecular design. A proper choice of substituent groups $R^2$ and $R^3$ permits to optimize polymer properties including molecular mobility, carbon density, thermal properties (e.g., glass transition temperature) of a polymer, and polymerization reactivity, and hence, to tailor resist performance factors including exposure latitude (EL), mask error enhancement factor (MEEF), depth of focus (DOF), and etching resistance. Although the ability to optimize these performance factors largely depends not only on the recurring units (1a), but also on the type and combination of other recurring units (or comonomer) to be copolymerized, it is preferred for such optimization that $R^2$ and $R^3$ bond together to form an aliphatic hydrocarbon ring, especially a bridged hydrocarbon ring, with the carbon atom to which they are attached.

Polymer

The polymer of the invention is characterized by comprising recurring units derived from the hydroxyl-containing monomer defined above, the recurring units being represented by the general formula (1a):

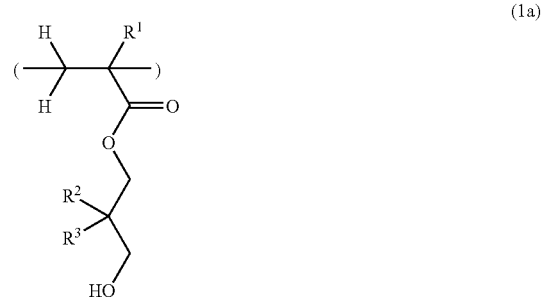

(1a)

wherein $R^1$, $R^2$ and $R^3$ are as defined above.

In addition to recurring units of formula (1a), the inventive polymer may further comprise recurring units of at least one type selected from the following general formulae (5a) to (8a).

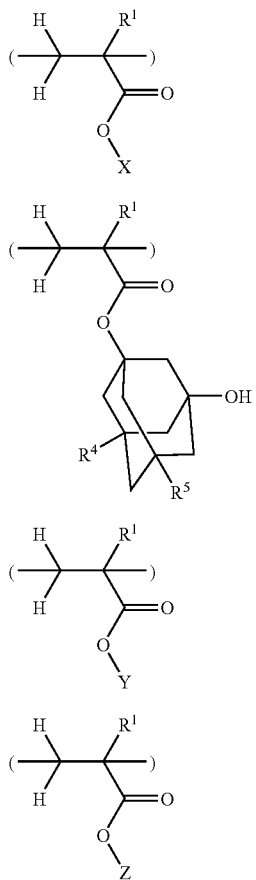

(5a)

(6a)

(7a)

(8a)

Herein R¹ is as defined above, R⁴ and R⁵ are each independently hydrogen or hydroxyl, X denotes an acid labile group, Y denotes a substituent group having lactone structure, and Z denotes hydrogen, a $C_1$-$C_{15}$ fluoroalkyl group or a $C_1$-$C_{15}$ fluoroalcohol-containing substituent group.

A polymer comprising recurring units of formula (5a) is decomposable under the action of an acid to generate a carboxylic acid so that the polymer may become alkali soluble. The acid labile groups represented by X may be selected from a variety of such groups, for example, groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

(L1)

(L2)

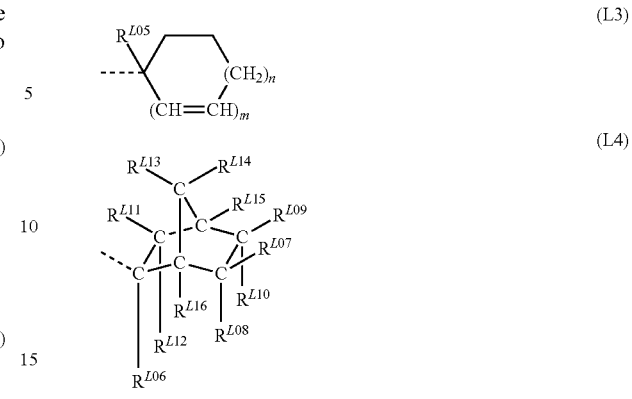

(L3)

(L4)

The broken line denotes a valence bond. In formula (L1), $R^{L01}$ and $R^{L02}$ are hydrogen or straight, branched or cyclic alkyl groups of 1 to 18 carbon atoms, preferably 1 to 10 carbon atoms, examples of which include methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl. $R^{L03}$ is a monovalent hydrocarbon group of 1 to 18 carbon atoms, preferably 1 to 15 carbon atoms, which may contain a heteroatom such as oxygen, examples of which include straight, branched or cyclic alkyl groups and substituted forms of these groups in which some hydrogen atoms are replaced by hydroxyl, alkoxy, oxo, amino, alkylamino or the like. Examples of suitable substituted alkyl groups are shown below.

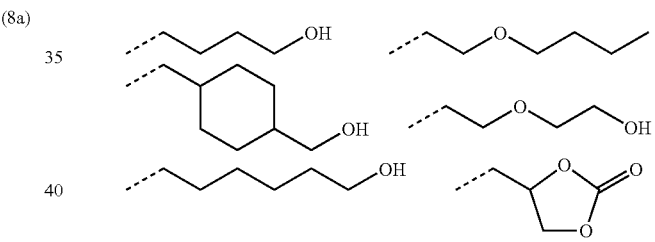

A pair of $R^{L01}$ and $R^{L02}$, $R^{L01}$ and $R^{L03}$, or $R^{L02}$ and $R^{L03}$ may bond together to form a ring with the carbon and oxygen atoms to which they are attached. Each participant of $R^{L01}$, $R^{L02}$ and $R^{L03}$ is a straight or branched alkylene group of 1 to 18 carbon atoms, preferably 1 to 10 carbon atoms when they form a ring.

In formula (L2), $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. In formula (L2), y is an integer of 0 to 6.

In formula (L3), $R^{L05}$ is a substituted or unsubstituted, straight, branched or cyclic $C_1$-$C_8$ alkyl group or a substituted or unsubstituted $C_6$-$C_{20}$ aryl group. Examples of the optionally substituted alkyl groups include straight, branched or cyclic ones such as methyl, ethyl, propyl, isopropyl, n-butyl, sec-butyl, tert-butyl, tert-amyl, n-pentyl, n-hexyl, cyclopentyl, and cyclohexyl; and substituted forms of the foregoing in which some hydrogen atoms are replaced by hydroxyl, alkoxy, carboxy, alkoxycarbonyl, oxo, amino, alkylamino, cyano, mercapto, alkylthio, sulfo or other groups and/or some —CH$_2$— are replaced by oxygen atoms. Exemplary optionally substituted aryl groups are phenyl, methylphenyl, naphthyl, anthryl, phenanthryl, and pyrenyl. In formula (L3), m is 0 or 1, n is 0, 1, 2 or 3, and 2m+n is equal to 2 or 3.

In formula (L4), $R^{L06}$ is a substituted or unsubstituted, straight, branched or cyclic $C_1$-$C_8$ alkyl group or a substituted or unsubstituted $C_6$-$C_{20}$ aryl group. Examples of these groups are the same as exemplified for $R^{L05}$. $R^{L07}$ to $R^{L16}$ independently denote hydrogen or monovalent $C_1$-$C_{15}$ hydrocarbon groups. Exemplary hydrocarbon groups are straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of the foregoing in which some hydrogen atoms are replaced by hydroxyl, alkoxy, carboxy, alkoxycarbonyl, oxo, amino, alkylamino, cyano, mercapto, alkylthio, sulfo or other groups. Alternatively, two of $R^{L07}$ to $R^{L16}$ may bond together to form a ring with the carbon atom to which they are attached (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, $R^{L13}$ and $R^{L14}$, or a similar pair). Each participant of $R^{L07}$ to $R^{L16}$ represents a divalent $C_1$-$C_{15}$ hydrocarbon group when they form a ring, examples of which are the ones exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, or a similar pair).

Of the acid labile groups of formula (L1), the straight and branched ones are exemplified by the following groups.

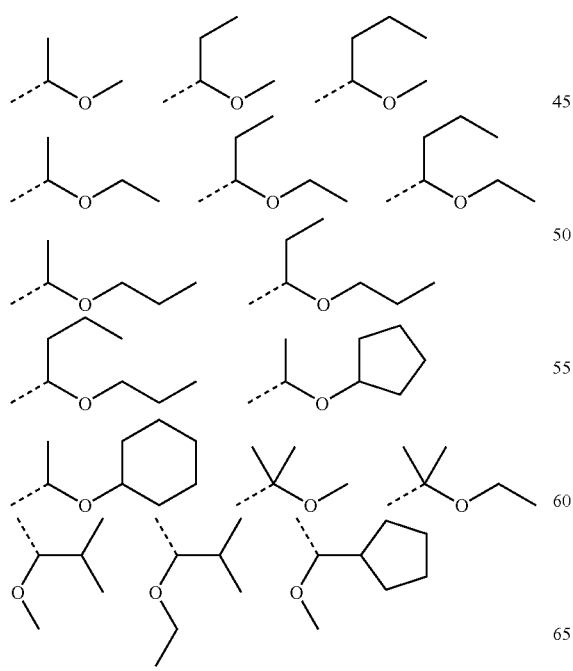

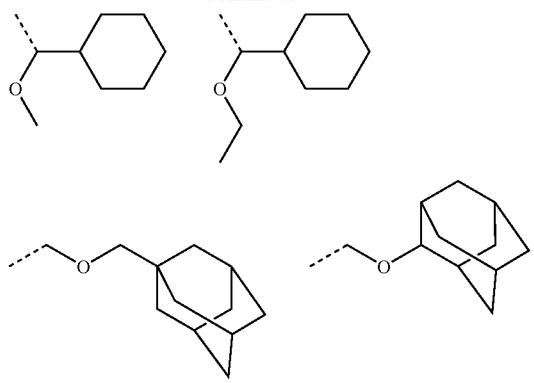

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl.

The acid labile group of formula (L4) is preferably selected from groups of the following formulae (L4-1) to (L4-4).

(L4-1)

(L4-2)

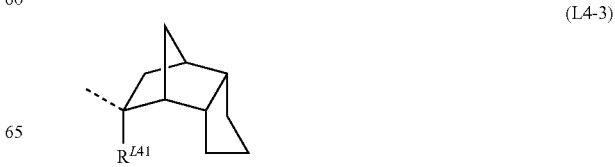

(L4-3)

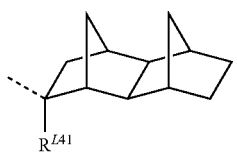
(L4-4)

In formulae (L4-1) to (L4-4), the broken line denotes a bonding site and direction. $R^{L41}$ is each independently selected from monovalent hydrocarbon groups, typically straight, branched or cyclic $C_1$-$C_{10}$ alkyl groups, for example, methyl, ethyl, propyl, isopropyl, n-butyl, sec-butyl, tert-butyl, tert-amyl, n-pentyl, n-hexyl, cyclopentyl, and cyclohexyl.

For formulas (L4-1) to (L4-4), there can exist enantiomers and diastereomers. Each of formulae (L4-1) to (L4-4) collectively represents all such stereoisomers. Such stereoisomers may be used alone or in admixture.

For example, the general formula (L4-3) represents one or a mixture of two selected from groups having the following general formulas (L4-3-1) and (L4-3-2).

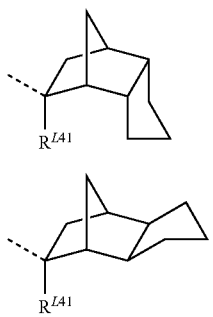
(L4-3-1)

(L4-3-2)

$R^{L41}$ is as defined above.

Similarly, the general formula (L4-4) represents one or a mixture of two or more selected from groups having the following general formulas (L4-4-1) to (L4-4-4).

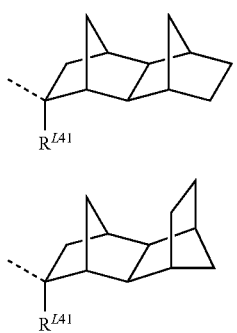
(L4-4-1)

(L4-4-2)

(L4-4-3)

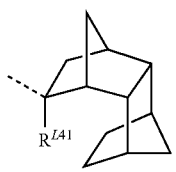

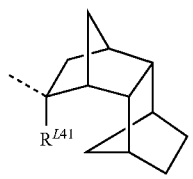
(L4-4-4)

$R^{L41}$ is as defined above.

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1]heptane ring, which ensures high reactivity for acid catalyzed elimination reaction (see JP-A 2000-336121). In preparing these monomers having a tertiary exo-alkyl group of bicyclo[2.2.1]heptane skeleton as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

(L4-1-endo)

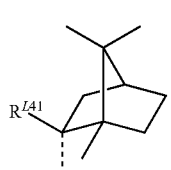
(L4-2-endo)

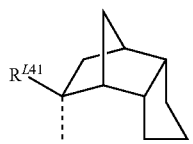
(L4-3-endo)

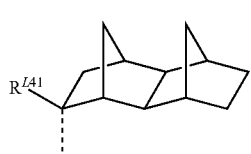
(L4-4-endo)

$R^{L41}$ is as defined above.

Illustrative examples of the acid labile group of formula (L4) are given below, but not limited thereto.

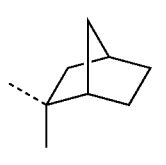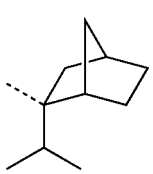

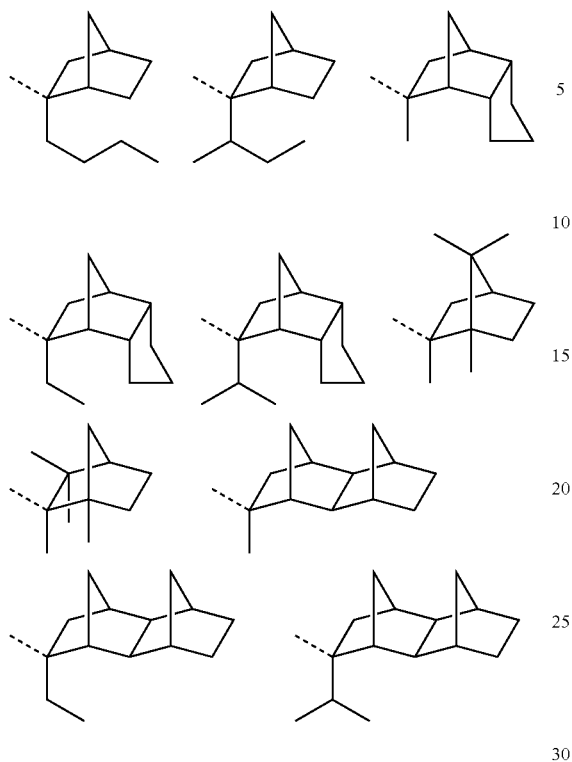
Examples of the tertiary $C_4$-$C_{20}$ alkyl, tri($C_1$-$C_6$-alkyl)silyl and $C_4$-$C_{20}$ oxoalkyl groups are as exemplified above for $R^{L04}$.
Illustrative, non-limiting examples of the recurring units of formula (5a) are given below.
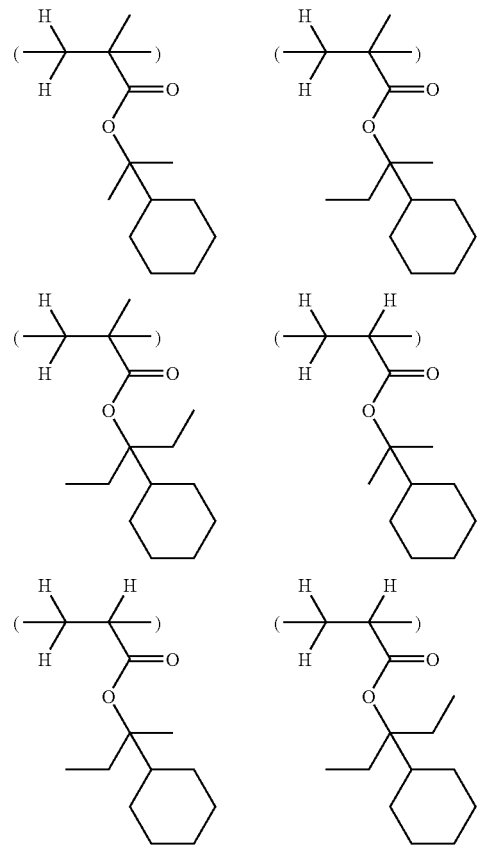
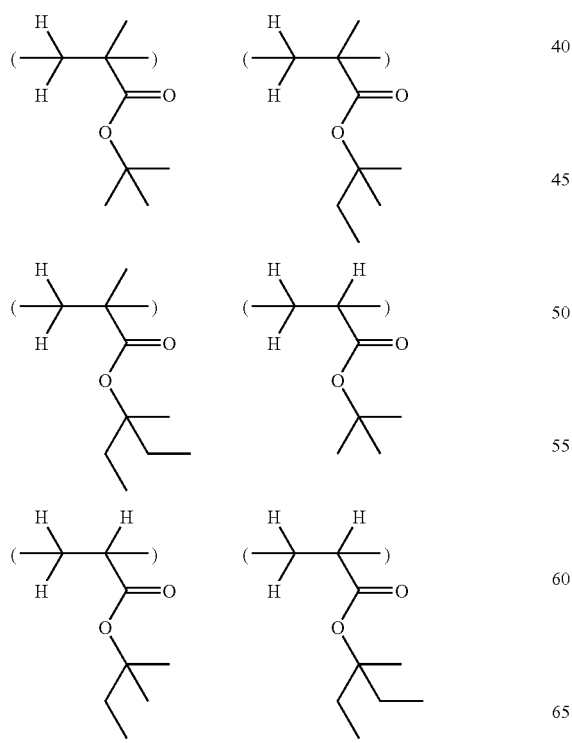
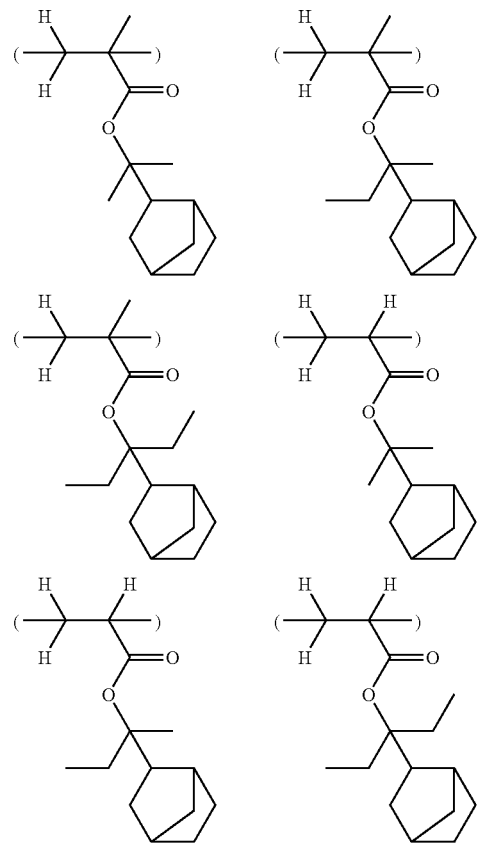

-continued
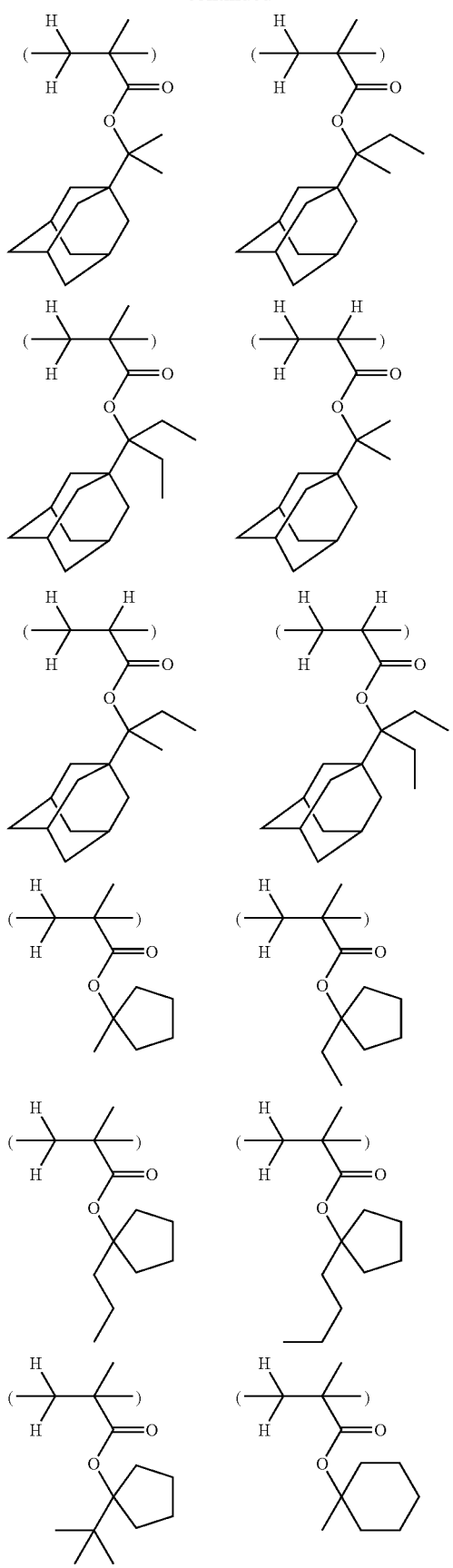
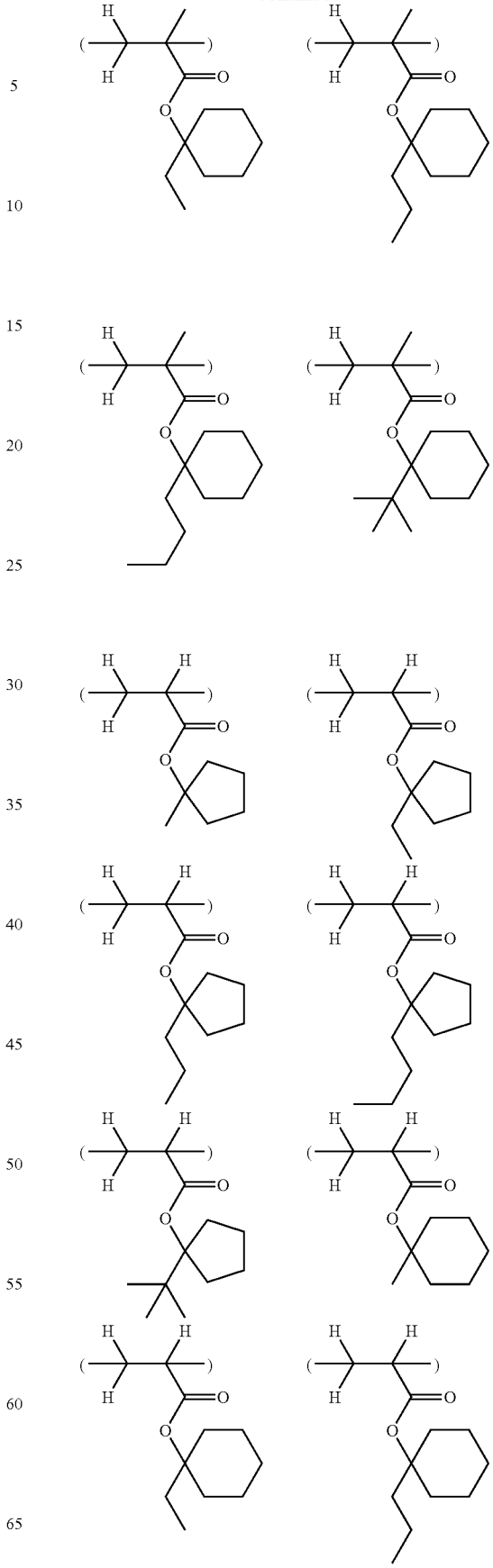

-continued
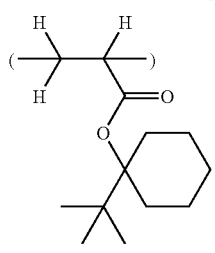 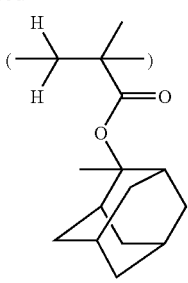 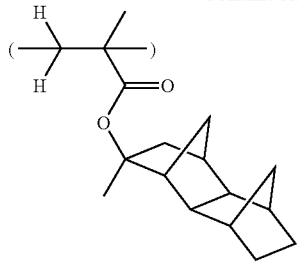
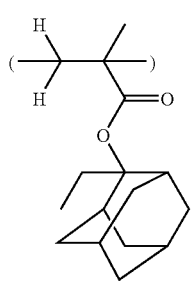 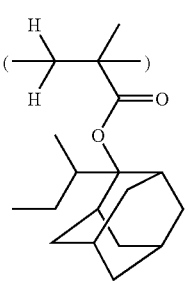 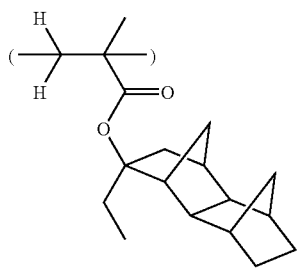
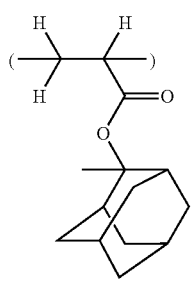 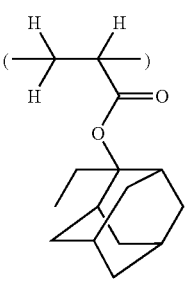 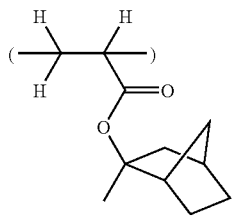 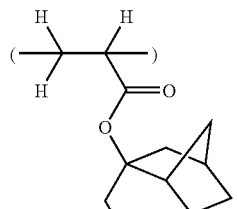
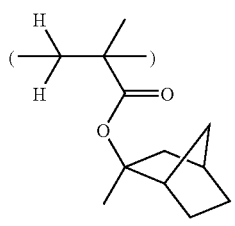 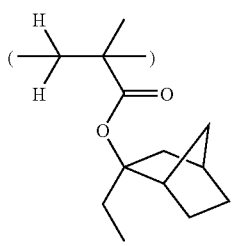 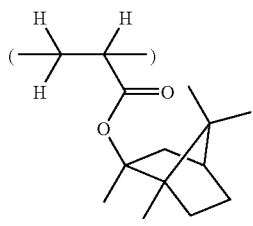 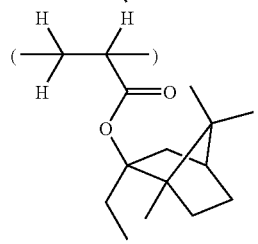
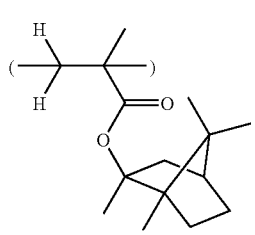 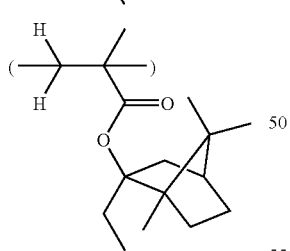 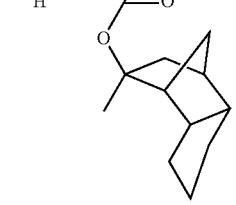 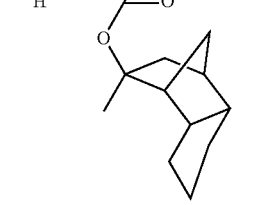
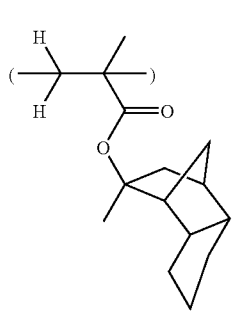 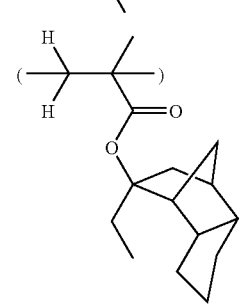 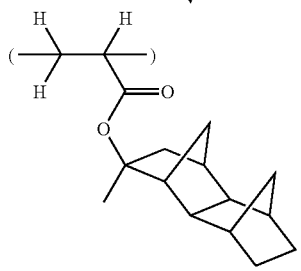

-continued
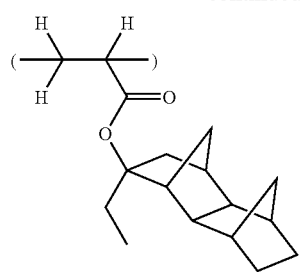 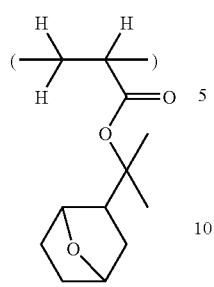 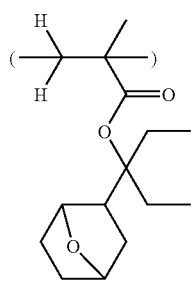 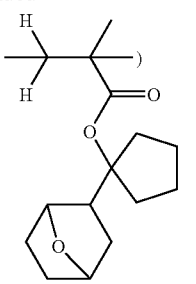
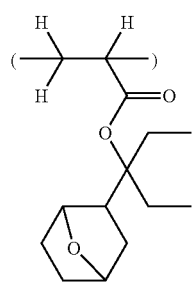 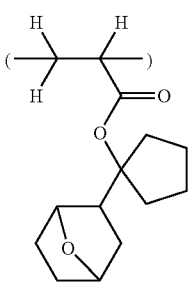 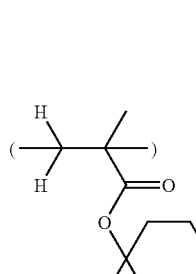 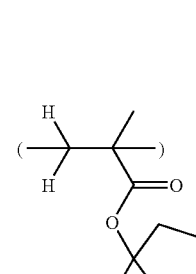
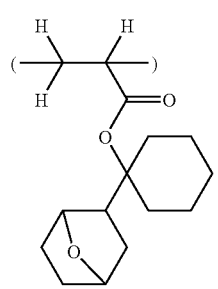 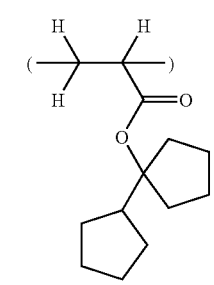 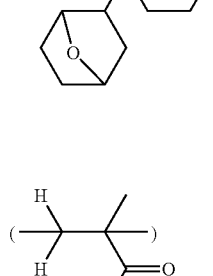 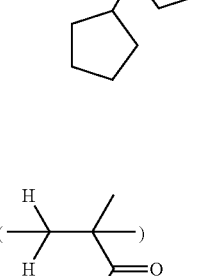
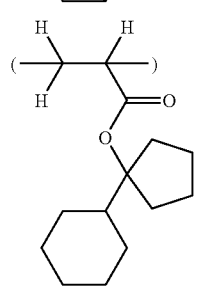 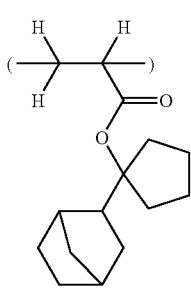 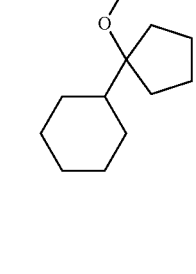 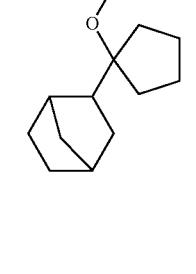
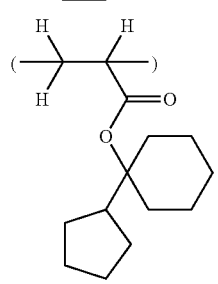 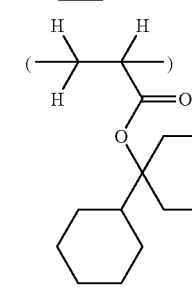 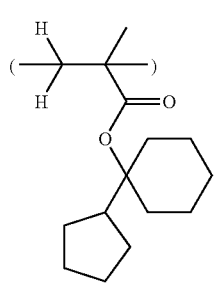 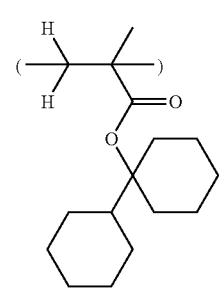
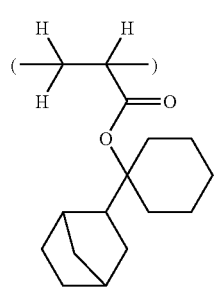 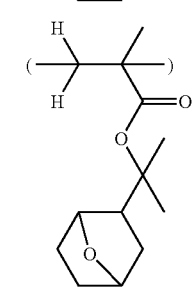 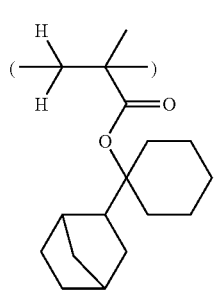 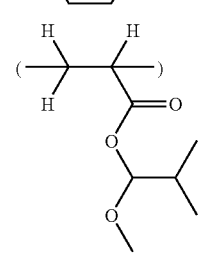

-continued
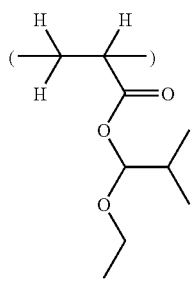 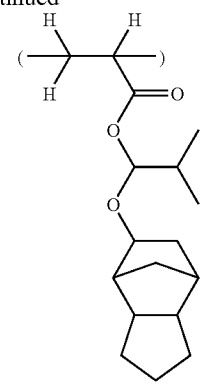
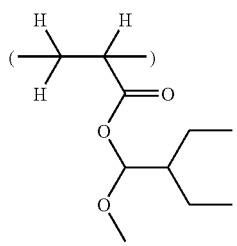 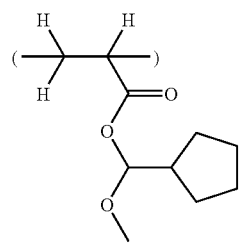
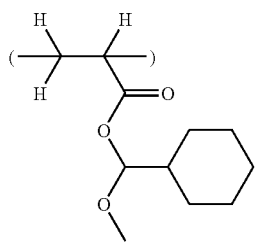 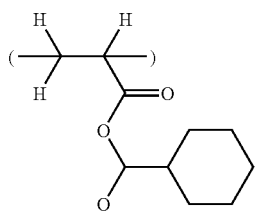
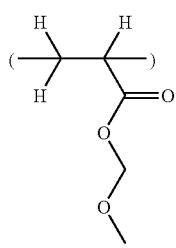 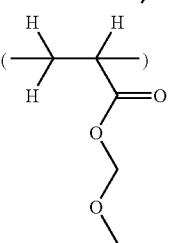
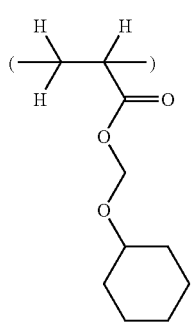 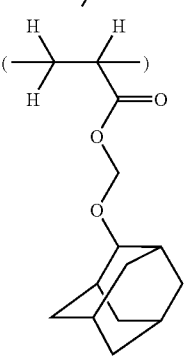
-continued
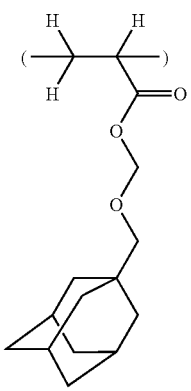 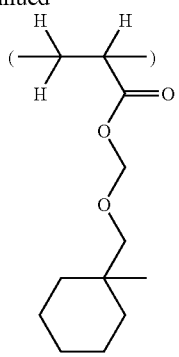
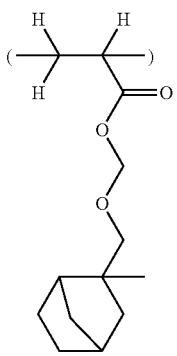 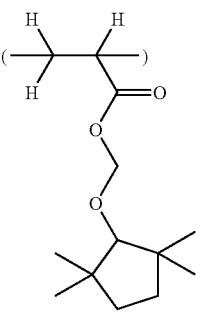
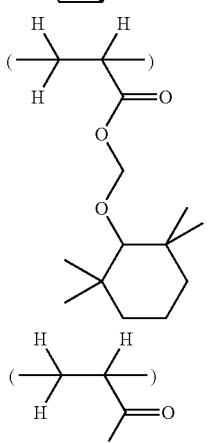 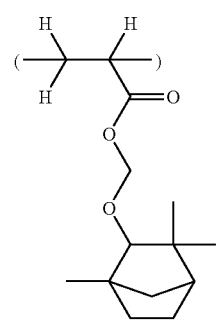
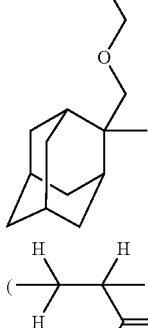 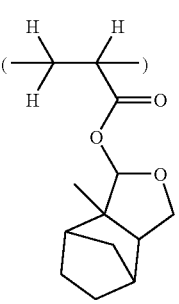
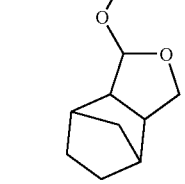 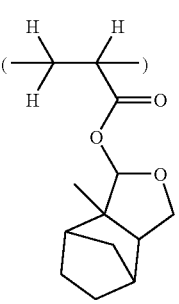

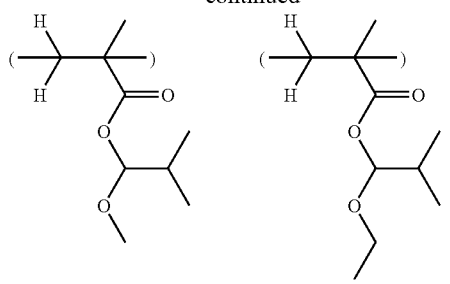

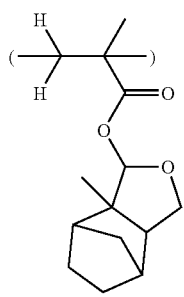
Illustrative, non-limiting examples of the recurring units of formula (6a) are given below.
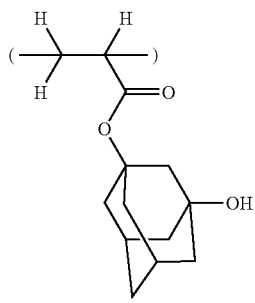
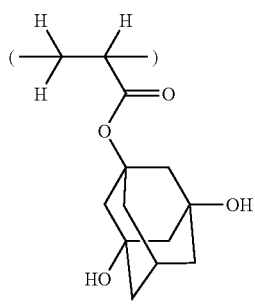
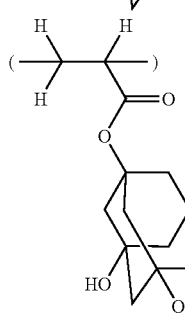
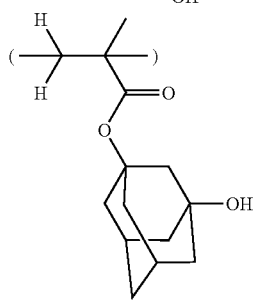
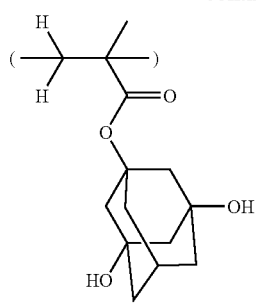
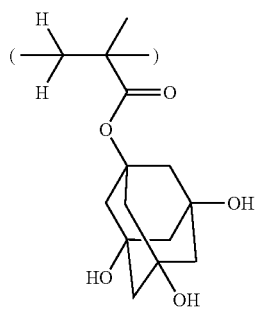
Illustrative, non-limiting examples of the recurring units of formula (7a) are given below wherein Me is methyl.
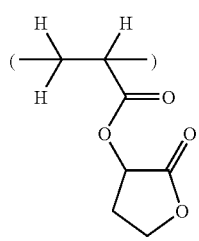 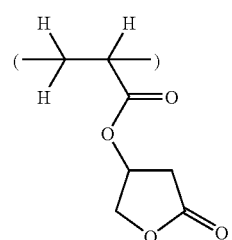
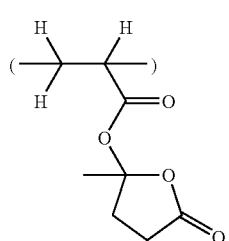
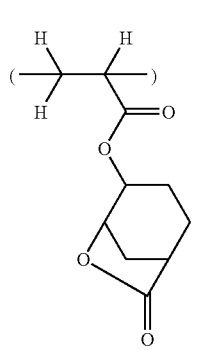 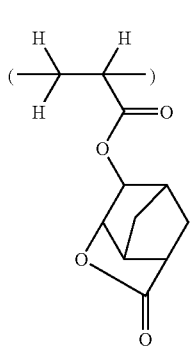

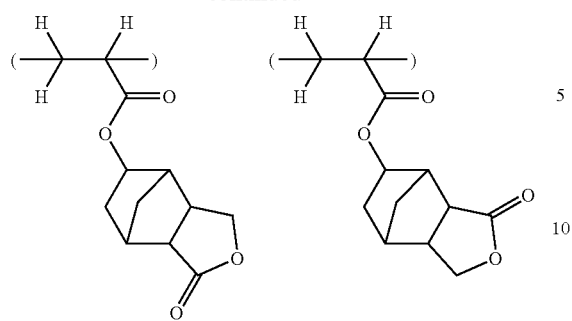
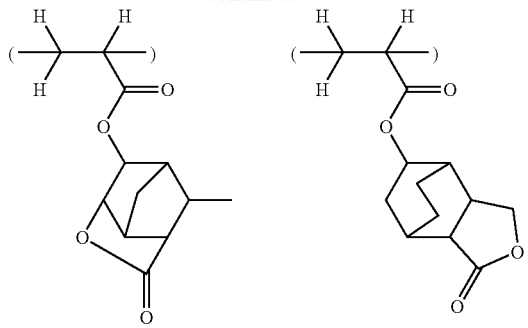
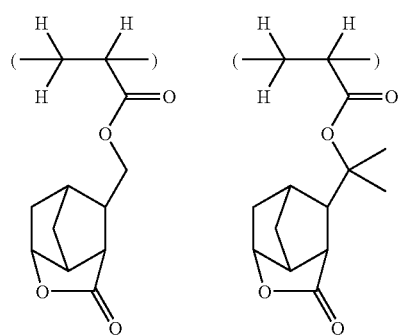
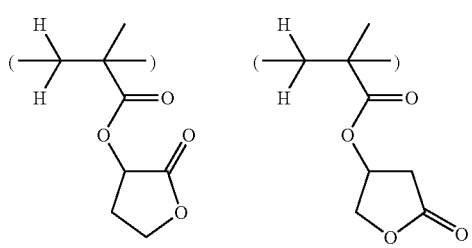
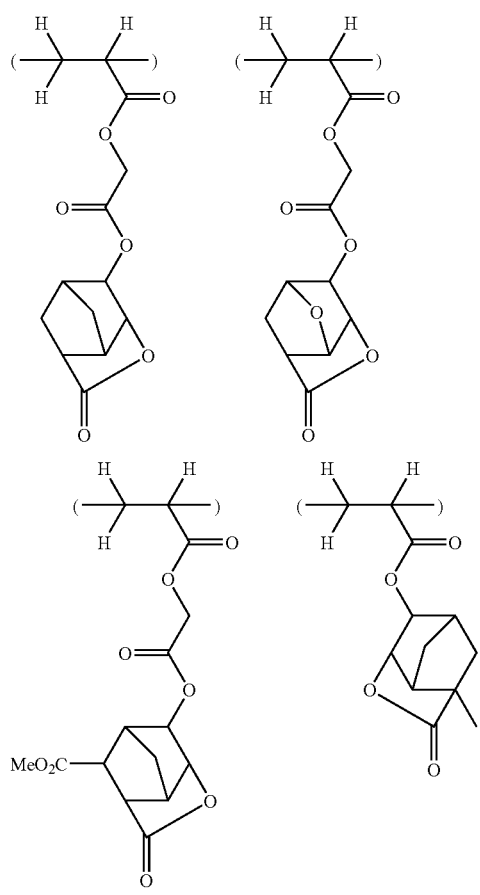
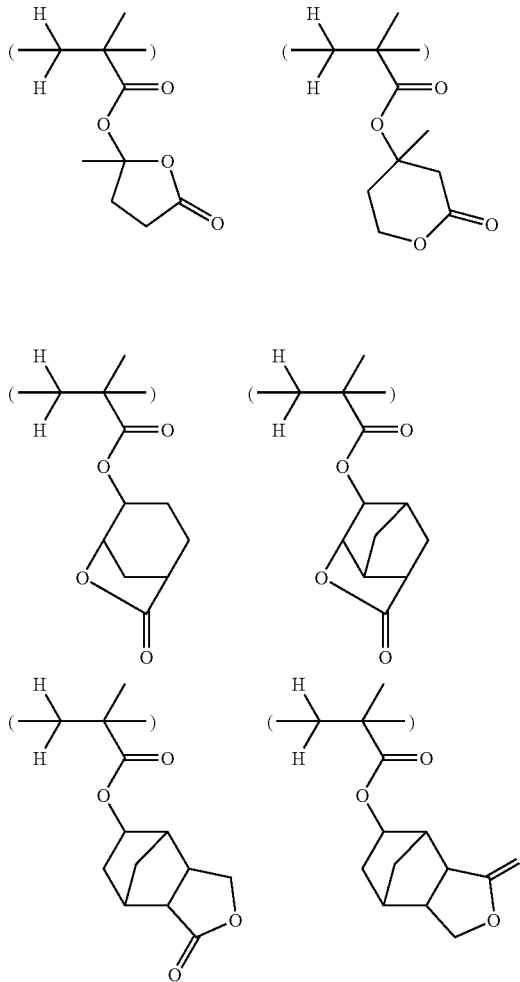

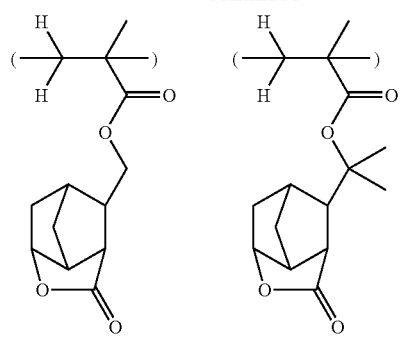
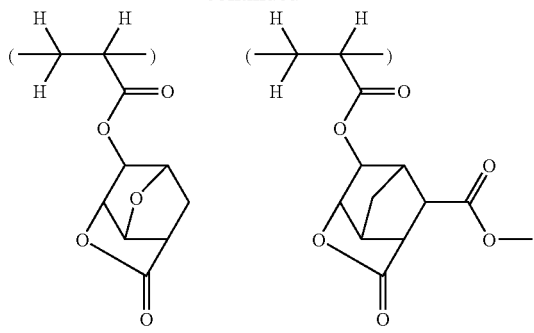
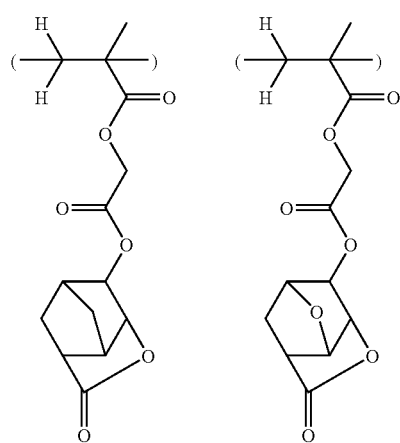
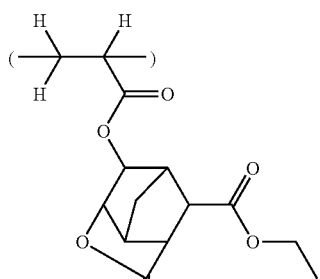
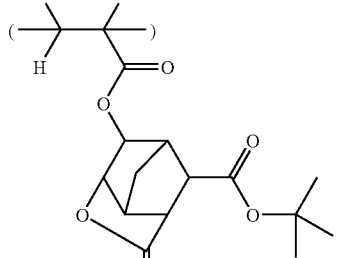
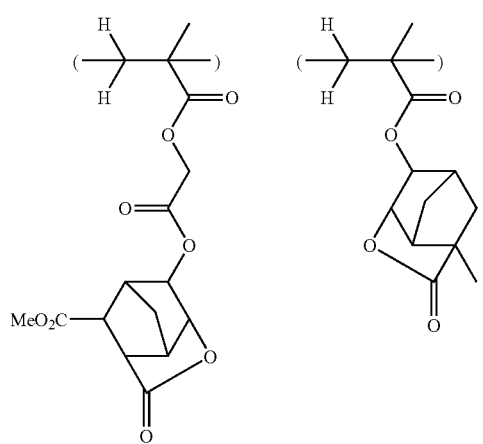
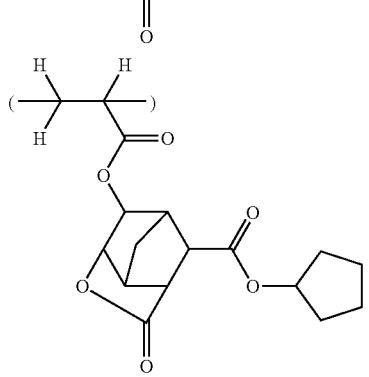
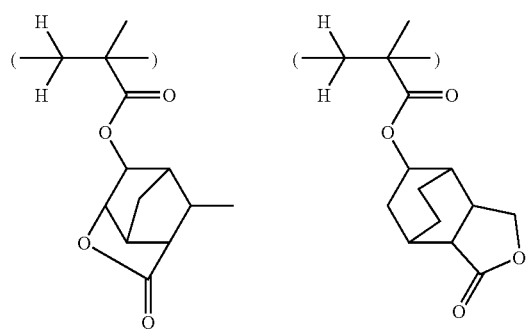
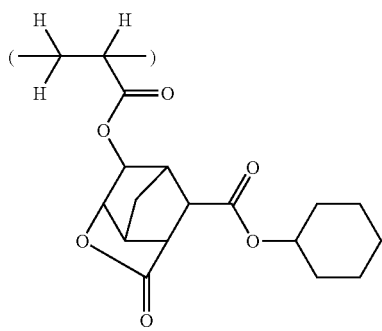

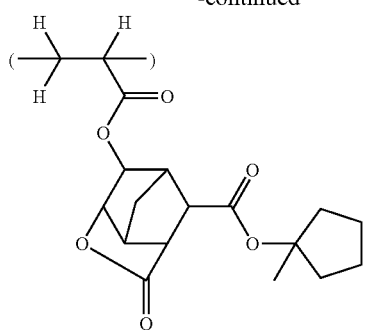
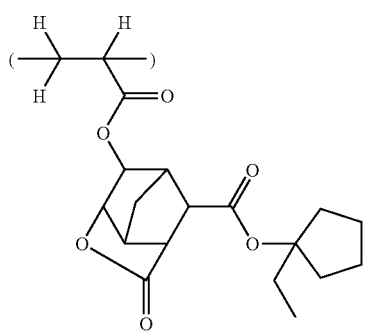
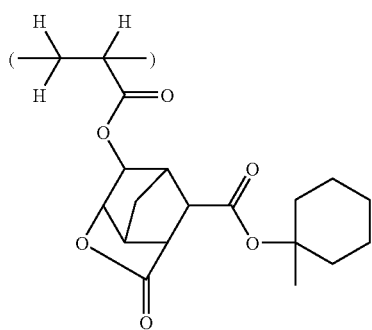
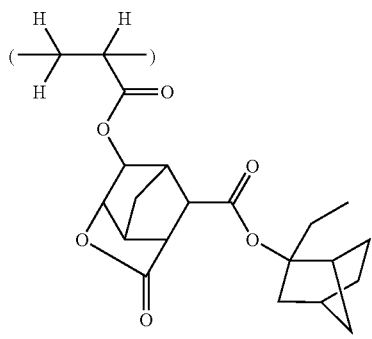
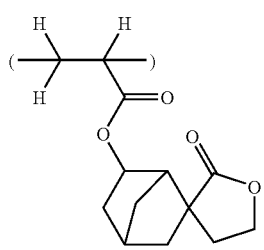
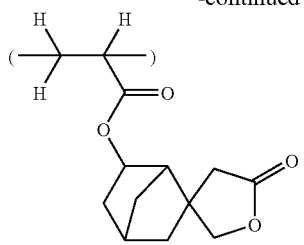
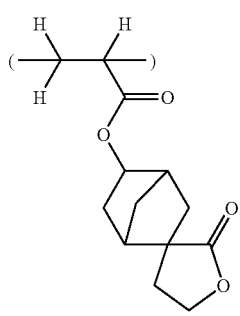
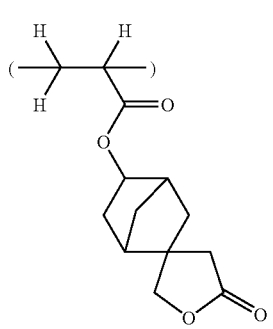
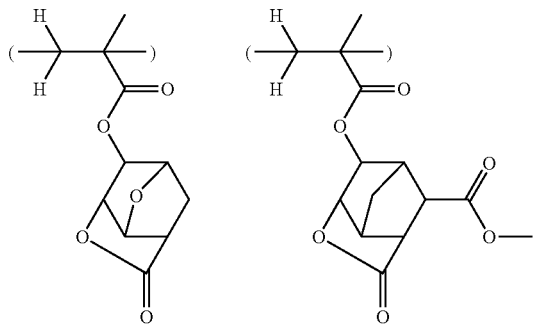
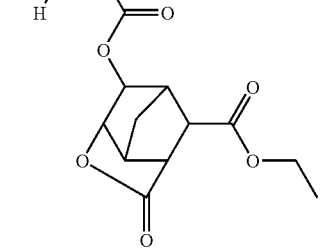

37
-continued
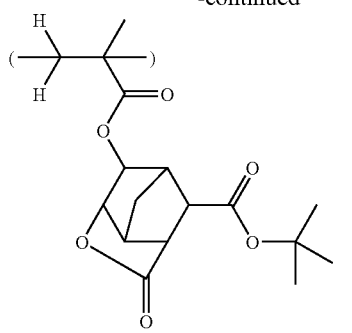
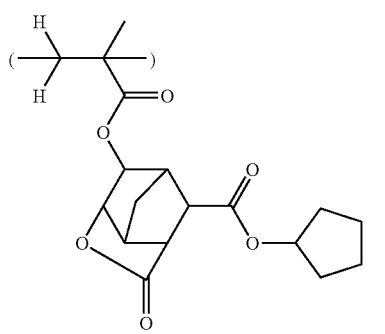
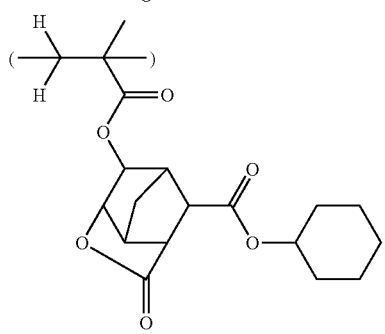
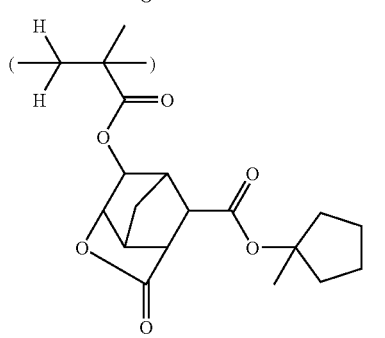
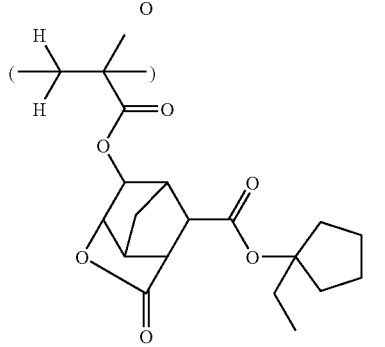
38
-continued
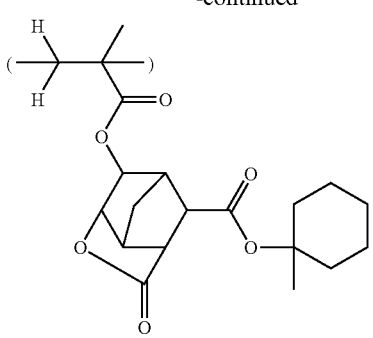
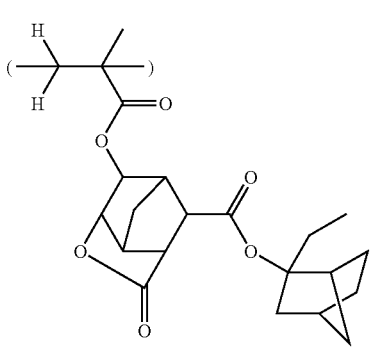
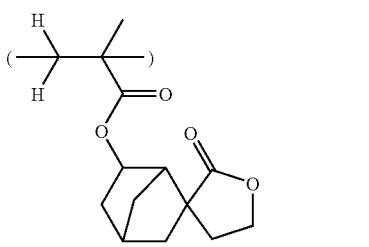
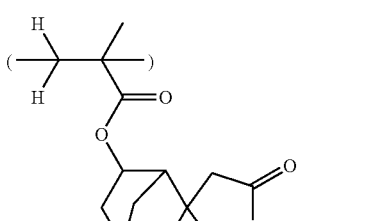
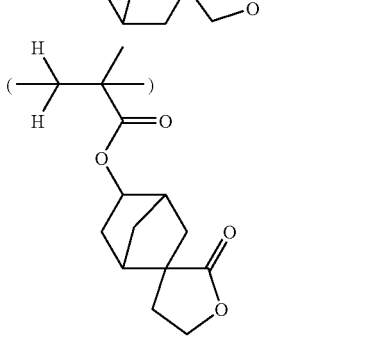

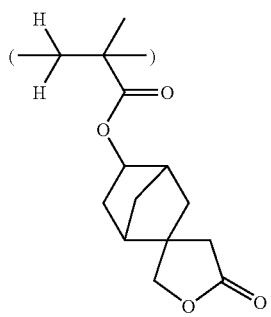
Illustrative, non-limiting examples of the recurring units of formula (8a) are given below.
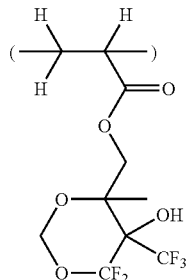
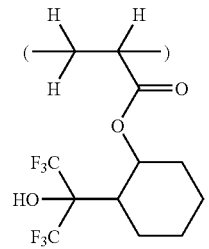
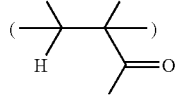
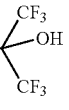
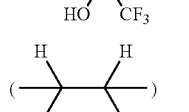
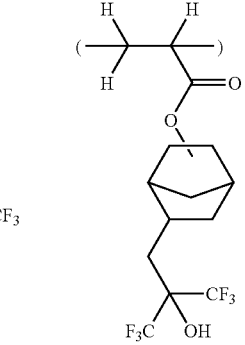
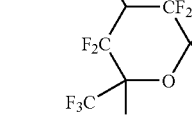
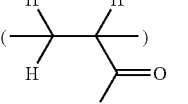
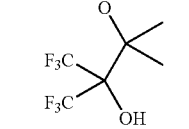
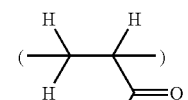
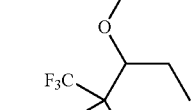
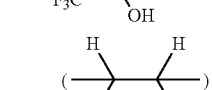
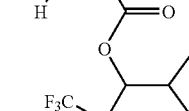
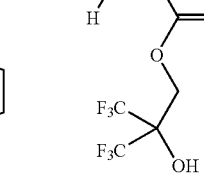

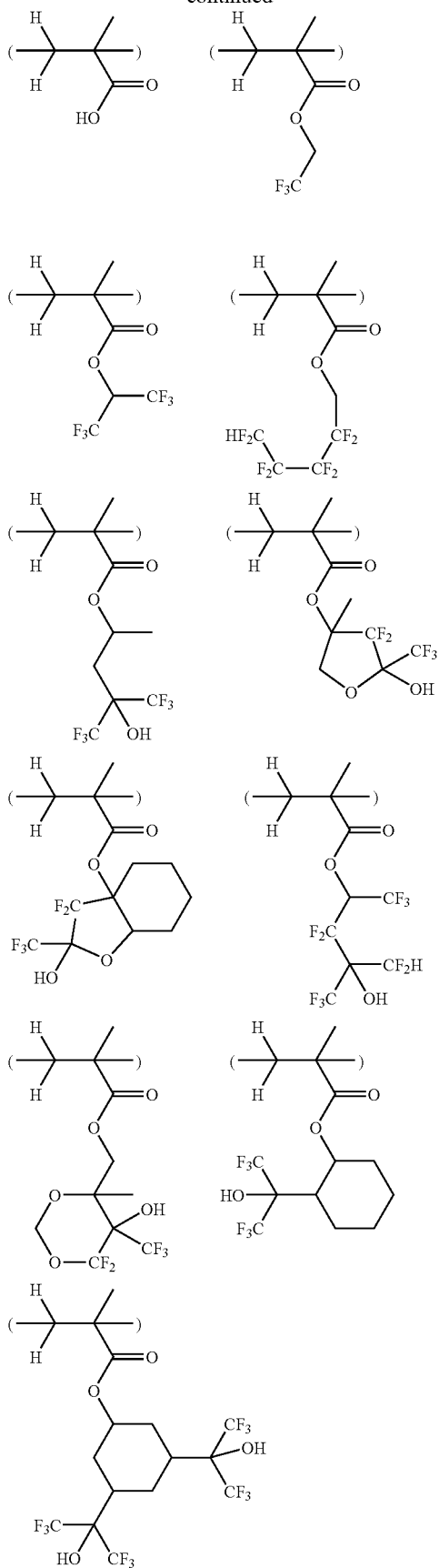

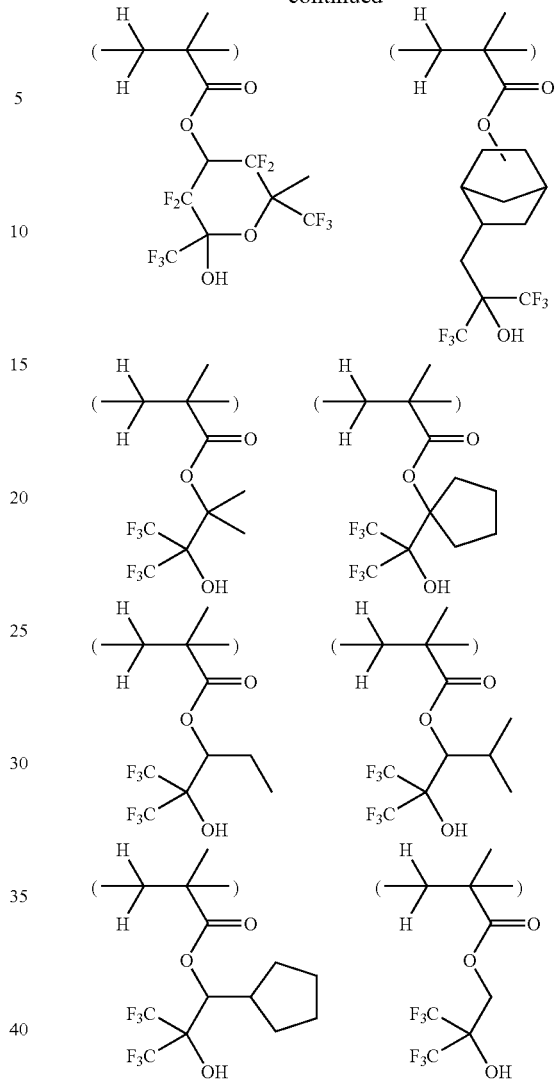

The polymer of the invention may further comprise recurring units derived from another monomer having a carbon-to-carbon double bond other than the foregoing. Examples of the additional monomer include substituted acrylic acid esters such as methyl methacrylate, methyl crotonate, dimethyl maleate, and dimethyl itaconate, unsaturated carboxylic acids such as maleic acid, fumaric acid and itaconic acid, cyclic olefins such as norbornene, norbornene derivatives, and tetracyclo[4.4.0.1$^{2,5}$.1$^{7,10}$]dodecene derivatives, unsaturated acid anhydrides such as itaconic anhydride, and other monomers.

The polymers have a weight average molecular weight (Mw) of 1,000 to 500,000, and preferably 3,000 to 100,000, as measured by gel permeation chromatography (GPC) versus polystyrene standards. Outside the range, a polymer may suffer an extreme drop of etching resistance or a reduced resolution due to a failure to provide a difference in dissolution rate before and after exposure.

In the inventive polymer, the preferred proportion of respective recurring units derived from discrete monomers may fall, for example, in the range (mol %) shown below, but is not limited thereto. The polymer may consist essentially of:

(I) from more than 0 mol % to 100 mol %, preferably 2 to 70 mol %, and more preferably 5 to 50 mol % of constituent units having formula (1a) derived from monomer having formula (1);

(II) from 0 mol % to less than 100 mol %, preferably 1 to 95 mol %, and more preferably 20 to 80 mol % of constituent units of one or more type having formulae (5a) to (8a); and optionally, (III) from 0 mol % to 80 mol %, preferably 0 to 70 mol %, and more preferably 0 to 50 mol % of constituent units of one or more type derived from the additional monomer(s).

Preferably, the polymer contains 1 to 95 mol %, especially 20 to 80 mol % of recurring units having formula (5a); 0 to 95 mol %, especially 0 to 50 mol % of recurring units having formula (6a); 0 to 95 mol %, especially 20 to 80 mol % of recurring units having formula (7a); and 0 to 95 mol %, especially 0 to 50 mol % of recurring units having formula (8a).

The polymer of the invention may be prepared through copolymerization reaction using the compound having formula (1) as a first monomer and one or more compounds having a polymerizable double bond as second and subsequent monomers. Each of the hydroxyl-containing compound having formula (1) as a first monomer and second and subsequent monomers which are used in the copolymerization process may contain oligomeric and polymeric fractions which are preferably present in an amount of up to 10 mol %, more nreferably up to 3 mol %, and even more preferably up to 1 mol % based on the monomer reactant.

Various modes of copolymerization reaction may be used for the preparation of the inventive polymer. The preferred modes are radical polymerization, anionic polymerization and coordination polymerization.

For radical polymerization, preferred reaction conditions include (a) a solvent selected from hydrocarbons such as benzene, ethers such as tetrahydrofuran, alcohols such as ethanol, and ketones such as methyl isobutyl ketone; (b) a polymerization initiator selected from azo compounds such as 2,2'-azobisisobutyronitrile, and peroxides such as benzoyl peroxide and lauroyl peroxide; (c) a reaction temperature in the range of about 0° C. to about 100° C.; and (d) a reaction time in the range of about 0.5 to about 48 hours. Reaction parameters outside these ranges need not be excluded.

For anionic polymerization, preferred reaction conditions include (a) a solvent selected from among hydrocarbons such as benzene, ethers such as tetrahydrofuran, and liquid ammonia, (b) a polymerization initiator selected from metals such as sodium and potassium, alkyl metals such as n-butyllithium and sec-butyllithium, ketyl, and Grignard reagents, (c) a temperature of about −78° C. to about 0° C., (d) a time of about ½ hour to about 48 hours, and (e) a stopper selected from among proton-donative compounds such as methanol, halides such as methyl iodide, and electrophilic compounds. Reaction parameters outside these ranges need not be excluded.

For coordination polymerization, preferred reaction conditions include (a) a solvent selected from among hydrocarbons such as n-heptane and toluene, (b) a catalyst selected from Ziegler-Natta catalysts comprising a transition metal (e.g., titanium) and alkylaluminum, Phillips catalysts of metal oxides having chromium or nickel compounds carried thereon, and olefin-metathesis mixed catalysts as typified by tungsten and rhenium mixed catalysts, (c) a temperature of about 0° C. to about 100° C., and (d) a time of about ½ hour to about 48 hours. Reaction parameters outside these ranges need not be excluded.

Resist Composition

The polymer of the invention is advantageously used as a base resin in a resist composition, and specifically a chemically amplified positive resist composition. Thus the invention provides a resist composition comprising the polymer, and especially a chemically amplified positive resist composition comprising the polymer. The resist composition preferably comprises:

(A) a base resin comprising the inventive polymer,
(B) an acid generator,
(C) an organic solvent, and optionally,
(D) an organic nitrogen-containing compound, and
(E) a surfactant.

For the resist composition, the base resin as component (A) may comprise another resin having a dissolution rate in an alkaline developer that increases under the action of an acid, if desired, as well as the inventive polymer. Exemplary other resins include, but are not limited to, (i) poly(meth)acrylic acid derivatives, (ii) norbornene derivative/maleic anhydride copolymers, (iii) hydrogenated products of ring-opening metathesis polymers (ROMP), and (iv) vinyl ether/maleic anhydride/(meth)acrylic acid derivative copolymers.

The hydrogenated products of ROMP (iii) are synthesized by the method illustrated in Examples of JP-A 2003-66612. Illustrative examples of such hydrogenated polymers include those polymers having the recurring units shown below, but are not limited thereto.

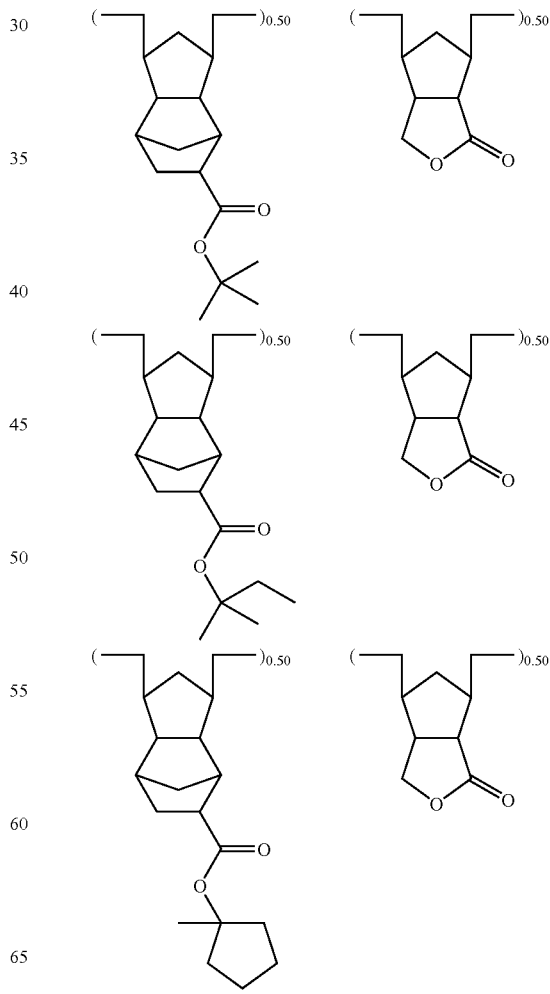

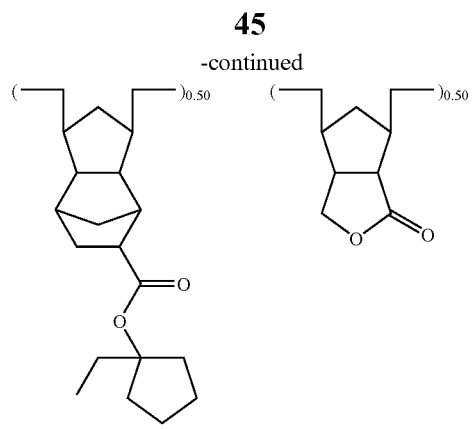
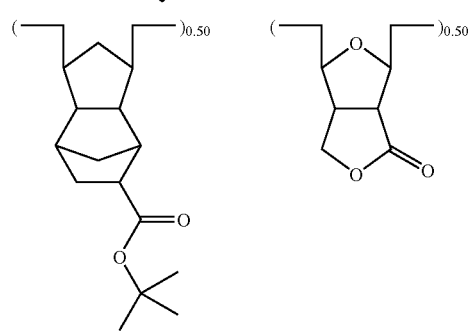
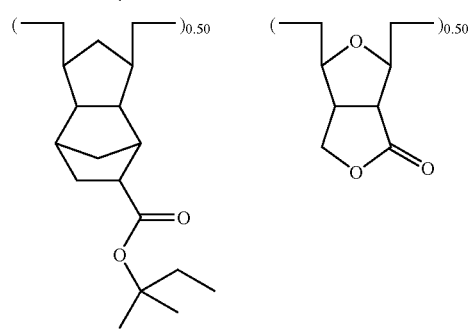
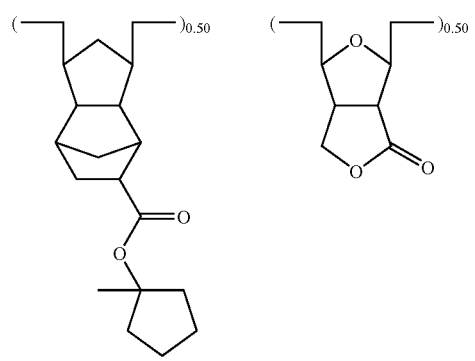
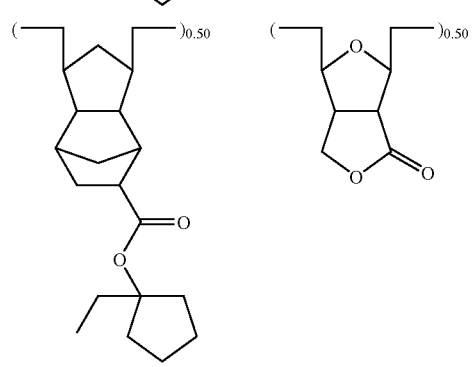
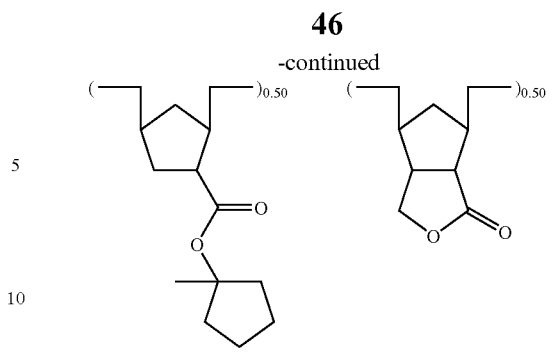
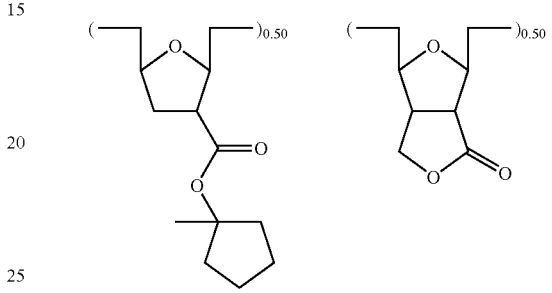
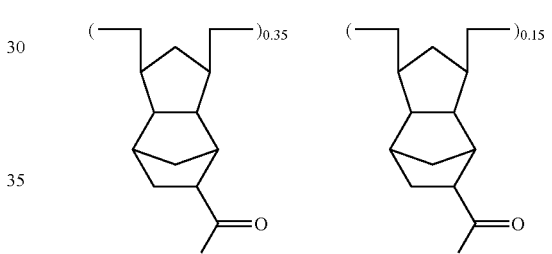
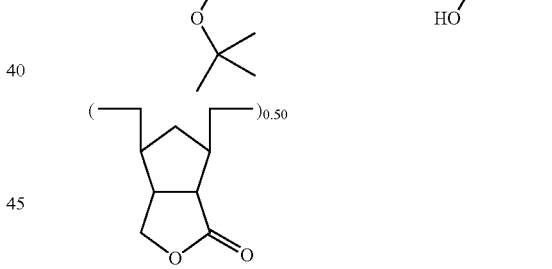
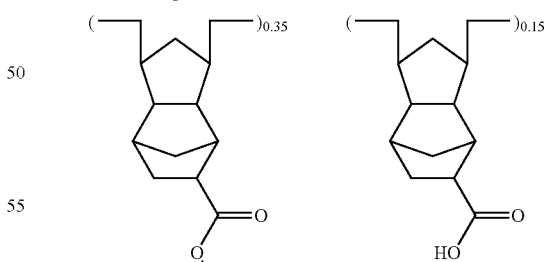
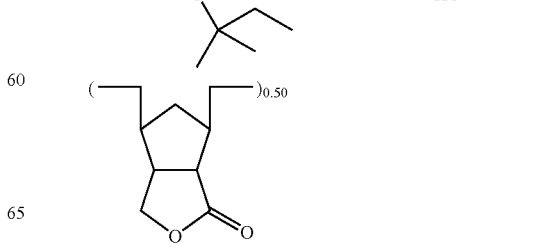

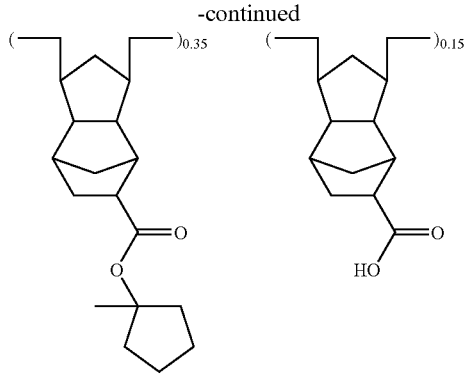
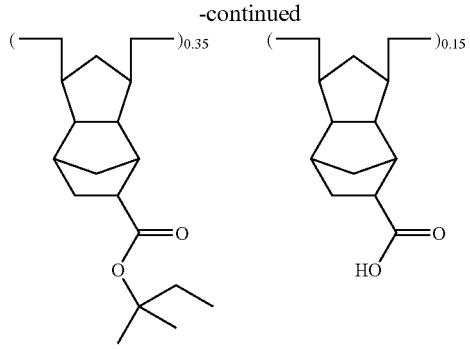
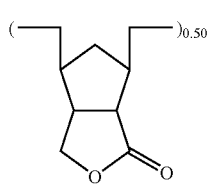
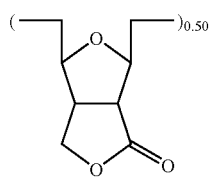
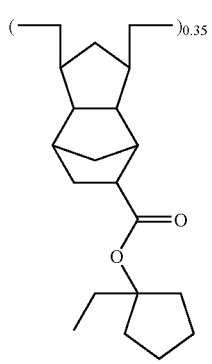
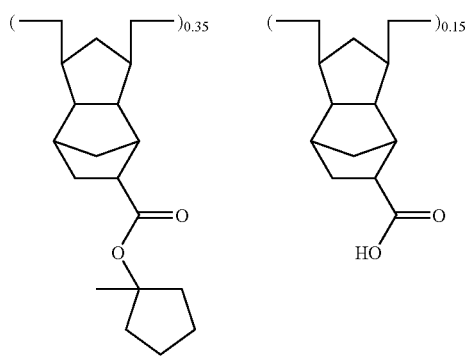
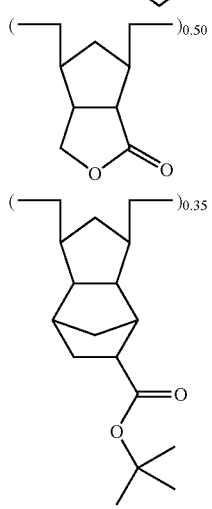
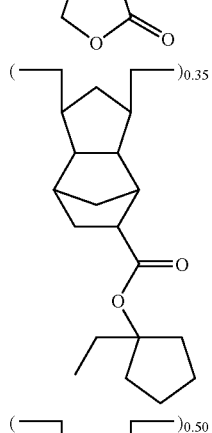

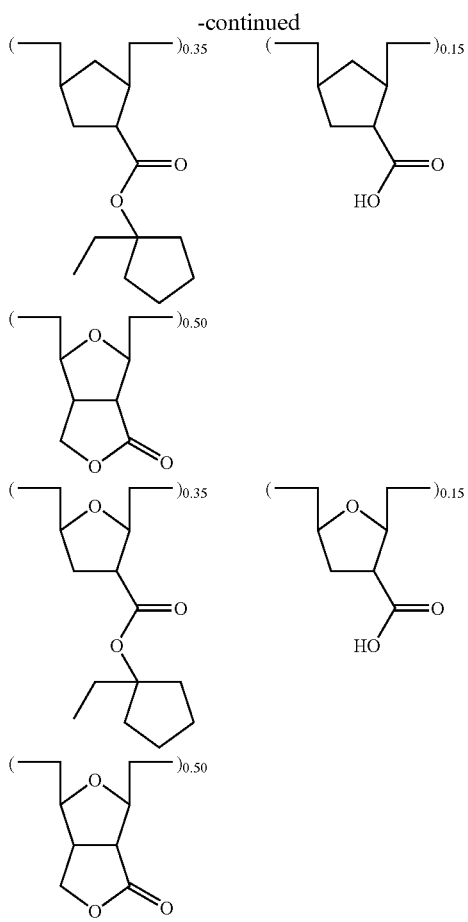

The inventive polymer and the other polymer are preferably blended in a weight ratio from 100:0 to 10:90, more preferably from 100:0 to 20:80. If the blend ratio of the inventive polymer is below this range, the resist composition would become poor in some of the desired properties. The properties of the resist composition can be adjusted by properly changing the blend ratio of the inventive polymer. The polymer is not limited to one type and a mixture of two or more polymers may be added. The use of plural polymers allows for easy adjustment of resist properties.

Acid Generator

In the resist composition of the invention, an acid generator is generally included. A typical acid generator is a photoacid generator (PAG) which may be any compound capable of generating an acid in response to high-energy radiation. Suitable photoacid generators include sulfonium salts, iodonium salts, sulfonyldiazomethane, N-sulfonyloxyimide, and oxime-O-sulfonate acid generators. Exemplary acid generators are given below while they may be used alone or in admixture of two or more.

Sulfonium salts are salts of sulfonium cations with sulfonates, bis(substituted alkylsulfonyl)imides and tris(substituted alkylsulfonyl)methides. Exemplary sulfonium cations include triphenylsulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-di-tert-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 2-naphthyldiphenylsulfonium, dimethyl-2-naphthylsulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxo-2-phenylethylthiacyclopentanium, 4-n-butoxynaphthyl-1-thiacyclopentanium, and 2-n-butoxynaphthyl-1-thiacyclopentanium. Exemplary sulfonates include trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, 4-(4'-toluenesulfonyloxy)benzenesulfonate, naphthalenesulfonate, camphorsulfonate, octanesulfonate, dodecylbenzenesulfonate, butanesulfonate, methanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-naphthylethanesulfonate, 1,1,2,2-tetrafluoro-2-(norbornan-2-yl)ethanesulfonate, and 1,1,2,2-tetrafluoro-2-(tetracyclo[4.4.0.1$^{2,5}$.1$^{7,10}$]dodec-3-en-8-yl) ethanesulfonate. Exemplary bis(substituted alkylsulfonyl)imides include bistrifluoromethylsulfonylimide, bispentafluoroethylsulfonylimide, bisheptafluoropropylsulfonylimide, and 1,3-propylenebissulfonylimide. A typical tris(substituted alkylsulfonyl)methide is tristrifluoromethylsulfonylmethide. Sulfonium salts based on combination of the foregoing examples are included.

Iodonium salts are salts of iodonium cations with sulfonates, bis(substituted alkylsulfonyl)imides and tris(substituted alkylsulfonyl)methides. Exemplary iodonium cations are aryliodonium cations including dinhenyliodinium, bis(4-tert-butylphenyl)iodonium, 4-tert-butoxyphenylphenyliodonium, and 4-methoxyphenylphenyliodonium. Exemplary sulfonates include trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, 4-(4-toluenesulfonyloxy)benzenesulfonate, naphthalenesulfonate, camphorsulfonate, octanesulfonate, dodecylbenzenesulfonate, butanesulfonate, methanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropane-sulfonate, 2-(4-tert-butylbenzoyloxy)-1,1,3,3,3-pentafluoropropane-sulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-naphthylethanesulfonate, 1,1,2,2-tetrafluoro-2-(norbornan-2-yl)ethanesulfonate, and 1,1,2,2-tetrafluoro-2-(tetracyclo[4.4.0.1$^{2,5}$.1$^{7,10}$]dodec-3-en-8-yl) ethanesulfonate. Exemplary bis(substituted alkylsulfonyl)imides include bistrifluoromethylsulfonylimide, bispentafluoroethylsulfonylimide, bisheptafluoropropylsulfonylimide, and 1,3-propylenebissulfonylimide. A typical tris(substituted alkylsulfonyl)methide is tristrifluoromethylsulfonylmethide. Iodonium salts based on combination of the foregoing examples are included.

Exemplary sulfonyldiazomethane compounds include bissulfonyldiazomethane compounds and sulfonyl-carbonyldiazomethane compounds such as bis(ethylsulfonyl)diazomethane, bis(1-methylpropylsulfonyl)diazomethane, bis(2-methylpropylsulfonyl)diazomethane, bis(1,1-dimethylethylsulfonyl)diazomethane, bis(cyclohexylsulfonyl)diazomethane, bis(perfluoroisopropylsulfonyl)diazomethane, bis(phenylsulfonyl)diazomethane, bis(4-methylphenylsulfonyl)diazomethane, bis(2,4-dimethylphenylsulfonyl)diazomethane, bis(2-naphthylsulfonyl)diazomethane, bis(4-acetyloxyphenylsulfonyl)diazomethane, bis(4-methanesulfonyloxyphenylsulfonyl)diazomethane, bis(4-(4-toluenesulfonyloxy)phenylsulfonyl)diazomethane, bis(4-(n-hexyloxy)phenylsulfonyl)diazomethane, bis(2-methyl-4-(n-hexyloxy)phenylsulfonyl)diazomethane, bis(2,5-dimethyl-4-(n-hexyloxy)phenylsulfonyl)diazomethane, bis(3,5-dimethyl-4-(n-hexyloxy)phenylsulfonyl)diazomethane, bis(2-methyl-5-isopropyl-4-(n-hexyloxy)phenylsulfonyl)-diazomethane, 4-methylphenylsulfonylbenzoyldiazomethane, tert-butylcarbonyl-4-methylphenylsulfonyldiazomethane, 2-naphthylsulfonylbenzoyldiazomethane, 4-methylphenylsulfonyl-2-naphthoyldiazomethane, methylsulfonylbenzoyldiazomethane, and tert-butoxycarbonyl-4-methylphenylsulfonyldiazomethane.

N-sulfonyloxyimide photoacid generators include combinations of imide skeletons with sulfonates. Exemplary imide skeletons are succinimide, naphthalene dicarboxylic acid imide, phthalimide, cyclohexyldicarboxylic acid imide, 5-norbornene-2,3-dicarboxylic acid imide, and 7-oxabicyclo[2.2.1]-5-heptene-2,3-dicarboxylic acid imide. Exemplary sulfonates include trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, naphthalenesulfonate, camphorsulfonate, octanesulfonate, dodecylbenzenesulfonate, butanesulfonate, methanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-adamantanecarbonyloxy-1,1,3,3,3-pentafluoropropane-sulfonate, 2-acetyloxy-1,1,3,3,3-pentafluoropropane-sulfonate, 1,1,3,3,3-pentafluoro-2-hydroxypropane-sulfonate, 1,1,3,3,3-pentafluoro-2-tosyloxypropanesulfonate, 1,1-difluoro-2-naphthylethanesulfonate, 1,1,2,2-tetrafluoro-2-(norbornan-2-yl)ethanesulfonate, and 1,1,2,2-tetrafluoro-2-(tetracyclo[4.4.0.1$^{2,5}$.1$^{7,10}$]dodec-3-en-8-yl)ethanesulfonate.

Benzoinsulfonate photoacid generators include benzoin tosylate, benzoin mesylate, and benzoin butanesulfonate.

Pyrogallol trisulfonate photoacid generators include pyrogallol, phloroglucinol, catechol, resorcinol, and hydroquinone, in which all the hydroxyl groups are substituted by trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonaLe, 4-trifluoromethylbenzenesulfonate, 4-fluorobenzenesulfonate, toluenesulfonate, benzenesulfonate, naphthalenesulfonate, camphorsulfonate, octanesulfonate, dodecylbenzenesulfonate, butanesulfonate, methanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-adamantanecarbonyloxy-1,1,3,3,3-pentafluoropropane-sulfonate, 2-acetyloxy-1,1,3,3,3-pentafluoropropane-sulfonate, 1,1,3,3,3-pentafluoro-2-hydroxypropane-sulfonate, 1,1,3,3,3-pentafluoro-2-tosyloxypropanesulfonate, 1,1-difluoro-2-naphthylethanesulfonate, 1,1,2,2-tetrafluoro-2-(norbornan-2-yl)ethanesulfonate, and 1,1,2,2-tetrafluoro-2-(.tetracyclo[4.4.0.1$^{2,5}$.1$^{7,10}$]dodec-3-en-8-yl)ethanesulfonate.

Nitrobenzyl sulfonate photoacid generators include 2,4-dinitrobenzyl sulfonate, 2-nitrobenzyl sulfonate, and 2,6-dinitrobenzyl sulfonate, with exemplary sulfonates including trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, toluenesulfonate, benzenesulfonate, naphthalenesulfonate, camphorsulfonate, octanesulfonate, dodecylbenzenesulfonate, butanesulfonate, methanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoronropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-adamantanecarbonyloxy-1,1,3,3,3-pentafluoropropane-sulfonate, 2-acetyloxy-1,1,3,3,3-pentafluoropropane-sulfonate, 1,1,3,3,3-pentafluoro-2-hydroxypropane-sulfonate, 1,1,3,3,3-pentafluoro-2-tosyloxypropanesulfonate, 1,1-difluoro-2-naphthylethanesulfonate, 1,1,2,2-tetrafluoro-2-(norbornan-2-yl)ethanesulfonate, and 1,1,2,2-tetrafluoro-2-(tetracyclo[4.4.0.1$^{2,5}$.1$^{7,10}$]dodec-3-en-8-yl) ethanesulfonate. Also useful are analogous nitrobenzyl sulfonate compounds in which the nitro group on the benzyl side is substituted by a trifluoromethyl group.

Sulfone photoacid generators include bis(phenylsulfonyl)methane, bis(4-methylphenylsulfonyl)methane, bis(2-naphthylsulfonyl)methane, 2,2-bis(phenylsulfonyl)propane, 2,2-bis(4-methylphenylsulfonyl)propane, 2,2-bis(2-naphthylsulfonyl)propane, 2-methyl-2-(p-toluenesulfonyl)propiophenone, 2-cyclohexylcarbonyl-2-(p-toluenesulfonyl)propane, and 2,4-dimethyl-2-(p-toluenesulfonyl)pentan-3-one.

Photoacid generators in the form of glyoxime derivatives are described in Japanese Patent No. 2,906,999 and JP-A 9-301948 and include bis-O-(p-toluenesulfonyl)-α-dimethylglyoxime, bis-O-(p-toluenesulfonyl)-α-diphenylglyoxime, bis-O-(p-toluenesulfonyl)-α-dicyclohexylglyoxime, bis-O-(p-toluenesulfonyl)-2,3-pentanedioneglyoxime, bis-O-(n-butanesulfonyl)-α-dimethylglyoxime, bis-O-(n-butanesulfonyl)-α-diphenylglyoxime, bis-O-(n-butanesulfonyl)-α-dicyclohexylglyoxime, bis-O-(methanesulfonyl)-α-dimethylglyoxime, bis-O-(trifluoromethanesulfonyl)-α-dimethylglyoxime, bis-O-(2,2,2-trifluoroethanesulfonyl)-α-dimethylglyoxime, bis-O-(10-camphorsulfonyl)-α-dimethylglyoxime, bis-O-(benzenesulfonyl)-α-dimethylglyoxime, bis-O-(p-fluorobenzenesulfonyl)-α-dimethylglyoxime, bis-O-(p-trifluoromethylbenzenesulfonyl)-α-dimethylglyoxime, bis-O-(xylenesulfonyl)-α-dimethylglyoxime, bis-O-(trifluoromethanesulfonyl)-nioxime, bis-O-(2,2,2-trifluoroethanesulfonyl)-nioxime, bis-O-(10-camphorsulfonyl)-nioxime, bis-O-(benzenesulfonyl)-nioxime, bis-O-(p-fluorobenzenesulfonyl)-nioxime, bis-O-(p-trifluoromethylbenzenesulfonyl)-nioxime, and bis-O-(xylenesulfonyl)-nioxime.

Also included are the oxime sulfonates described in U.S. Pat. No. 6,004,724, for example, (5-(4-toluenesulfonyl)oxyimino-5H-thiophen-2-ylidene)phenyl-acetonitrile, (5-(10-camphorsulfonyl)oxyimino-5H-thiophen-2-ylidene)phenyl-acetonitrile, (5-n-octanesulfonyloxyimino-5H-thiophen-2-ylidene)phenyl-acetonitrile, (5-(4-toluenesulfonyl)oxyimino-5H-thiophen-2-ylidene)(2-methylphenyl)acetonitrile, (5-(10-camphorsulfonyl)oxyimino-5H-thiophen-2-ylidene)(2-methylphenyl)acetonitrile, (5-n-octanesulfonyloxyimino-5H-thiophen-2-ylidene)(2-methylphenyl)acetonitrile, etc. Also included are the oxime sulfonates described in U.S. Pat. No. 6,916,591, for example, (5-(4-(4-toluenesulfonyloxy)benzenesulfonyl)oxyimino-5H-thiophen-2-ylidene)phenylacetonitrile and (5-(2,5-bis(4-toluenesulfonyloxy)benzenesulfonyl)oxyimino-5H-thiophen-2-ylidene)phenylacetonitrile.

Also included are the oxime sulfonates described in U.S. Pat. No. 6,261,738 and JP-A 2000-314956, for example, 2,2,2-trifluoro-1-phenyl-ethanone oxime-O-methylsulfonate; 2,2,2-trifluoro-1-phenyl-ethanone oxime-O-(10-camphorylsulfonate); 2,2,2-trifluoro-1-phenyl-ethanone oxime-O-(4-methoxyphenylsulfonate); 2,2,2-trifluoro-1-phenyl-ethanone oxime-O-(1-naphthylsulfonate); 2,2,2-trifluoro-1-phenyl-ethanone oxime-O-(2-naphthylsulfonate); 2,2,2-trifluoro-1-phenyl-ethanone oxime-O-(2,4,6-trimethylphenylsulfonate); 2,2,2-trifluoro-1-(4-methylphenyl)-ethanone oxime-O-(10-camphorylsulfonate); 2,2,2-trifluoro-1-(4-methylphenyl)-ethanone oxime-O-(methylsulfonate); 2,2,2-trifluoro-1-(2-methylphenyl)-ethanone oxime-O-(10-camphorylsulfonate); 2,2,2-trifluoro-1-(2,4-dimethylphenyl)-ethanone oxime-O-(10-camphorylsulfonate); 2,2,2-trifluoro-1-(2,4-dimethylphenyl)-ethanone oxime-O-(1-naphthylsulfonate); 2,2,2-trifluoro-1-(2,4-dimethylphenyl)-ethanone oxime-O-(2-naphthylsulfonate); 2,2,2-trifluoro-1-(2,4,6-trimethylphenyl)-ethanone oxime-O-(10-camphorylsulfonate); 2,2,2-trifluoro-1-(2,4,6-trimethylphenyl)-ethanone oxime-O-(2-naphthylsulfonate); 2,2,2-trifluoro-1-(4-methoxyphenyl)-ethanone oxime-O-methylsulfonate; 2,2,2-trifluoro-1-(4-methylthiophenyl)-ethanone oxime-O-methylsulfonate; 2,2,2-trifluoro-1-(3,4-dimethoxyphenyl)-ethanone oxime-O-methylsulfonate; 2,2,3,3,4,4,4-heptafluoro-1-phenyl-butanone oxime-O-(10-camphorylsulfonate); 2,2,2-trifluoro-1-(phenyl)-ethanone oxime-O-methylsulfonate; 2,2,2-trifluoro-1-(phenyl)-ethanone oxime-O-10-camphorylsulfonate; 2,2,2-trifluoro-1-(phenyl)-ethanone oxime-O-(4-methoxyphenyl)sulfonate; 2,2,2-trifluoro-1-(phenyl)-ethanone oxime-O-(1-naphthyl)sulfonate; 2,2,2-trifluoro-1-(phenyl)-ethanone oxime-O-(2-naphthyl)sulfonate; 2,2,2-trifluoro-1-(phenyl)-ethanone oxime-O-(2,4,6-trimethylphenyl)sulfonate; 2,2,2-trifluoro-1-(4-methylphenyl)-ethanone oxime-O-(10-camphoryl)sulfonate; 2,2,2-trifluoro-1-(4-methylphenyl)-ethanone oxime-O-methyl-sulfonate; 2,2,2-trifluoro-1-(2-methylphenyl)-ethanone oxime-O-(10-camphoryl)sulfonate; 2,2,2-trifluoro-1-(2,4-dimethylphenyl)-ethanone oxime-O-(1-naphthyl)sulfonate; 2,2,2-trifluoro-1-(2,4-dimethylphenyl)-ethanone oxime-O-(2-naphthyl)sulfonate; 2,2,2-trifluoro-1-(2,4,6-trimethyl-phenyl)-ethanone oxime-O-(10-camphoryl)sulfonate; 2,2,2-trifluoro-1-(2,4,6-trimethylphenyl)-ethanone oxime-O-(1-naphthyl)sulfonate; 2,2,2-trifluoro-1-(2,4,6-trimethyl-phenyl)-ethanone oxime-O-(2-naphthyl)sulfonate; 2,2,2-trifluoro-1-(4-methoxyphenyl)-ethanone oxime-O-methylsulfonate; 2,2,2-trifluoro-1-(4-thiomethylphenyl)-ethanone oxime-O-methylsulfonate; 2,2,2-trifluoro-1-(3,4-dimethoxyphenyl)-ethanone oxime-O-methylsulfonate; 2,2,2-trifluoro-1-(4-methoxyphenyl)-ethanone oxime-O-(4-methylphenyl)sulfonate; 2,2,2-trifluoro-1-(4-methoxyphenyl)-ethanone oxime-O-(4-methoxyphenyl)sulfonate; 2,2,2-trifluoro-1-(4-methoxyphenyl)-ethanone oxime-O-(4-dodecylphenyl)-sulfonate; 2,2,2-trifluoro-1-(4-methoxyphenyl)-ethanone oxime-O-octylsulfonate; 2,2,2-trifluoro-1-(4-thiomethyl-phenyl)-ethanone oxime-O-(4-methoxyphenyl)sulfonate; 2,2,2-trifluoro-1-(4-thiomethylphenyl)-ethanone oxime-O-(4-dodecylphenyl)sulfonate; 2,2,2-trifluoro-1-(4-thiomethyl-phenyl)-ethanone oxime-O-octylsulfonate; 2,2,2-trifluoro-1-(4-thiomethylphenyl)-ethanone oxime-O-(2-naphthyl)sulfonate; 2,2,2-trifluoro-1-(2-methylphenyl)-ethanone oxime-O-methyl-sulfonate; 2,2,2-trifluoro-1-(4-methylphenyl)ethanone oxime-O-phenylsulfonate; 2,2,2-trifluoro-1-(4-chlorophenyl)-ethanone oxime-O-phenylsulfonate; 2,2,3,3,4,4,4-heptafluoro-1-(phenyl)-butanone oxime-O-(10-camphoryl)sulfonate; 2,2,2-trifluoro-1-naphthyl-ethanone oxime-O-methylsulfonate; 2,2,2-trifluoro-2-naphthyl-ethanone oxime-O-methylsulfonate; 2,2,2-trifluoro-1-[4-benzylphenyl]-ethanone oxime-O-methylsulfonate; 2,2,2-trifluoro-1-[4-(phenyl-1,4-dioxa-but-1-yl)phenyl]-ethanone oxime-O-methylsulfonate; 2,2,2-trifluoro-1-naphthyl-ethanone oxime-O-propylsulfonate; 2,2,2-trifluoro-2-naphthyl-ethanone oxime-O-propylsulfonate; 2,2,2-trifluoro-1-[4-benzylphenyl]-ethanone oxime-O-propyl-sulfonate; 2,2,2-trifluoro-1-[4-methylsulfonylphenyl]-ethanone oxime-O-propylsulfonate; 1,3-bis[1-(4-phenoxy-phenyl)-2,2,2-trifluoroethanone oxime-O-sulfonyl]phenyl; 2,2,2-trifluoro-1-[4-methylsulfonyloxyphenyl]-ethanone oxime-O-propylsulfonate; 2,2,2-trifluoro-1-[4-methylcarbonyloxyphenyl]-ethanone oxime-O-propylsulfonate; 2,2,2-trifluoro-1-[6H,7H-5,8-dioxonaphth-2-yl]-ethanone oxime-O-propylsulfonate; 2,2,2-trifluoro-1-[4-methoxycarbonylmethoxyphenyl]-ethanone oxime-O-propylsulfonate; 2,2,2-trifluoro- 1-[4-(methoxycarbonyl)-(4-amino-1-oxa-pent-1-yl)-phenyl]-ethanone oxime-O-propylsulfonate; 2,2,2-trifluoro-1-[3,5-dimethyl-4-ethoxyphenyl]-ethanone oxime-O-propylsulfonate; 2,2,2-trifluoro-1-[4-benzyloxyphenyl]-ethanone oxime-O-propylsulfonate; 2,2,2-trifluoro-1-[2-thiophenyl]-ethanone oxime-O-propylsulfonate; 2,2,2-trifluoro-1-[1-dioxa-thiophen-2-yl)]-ethanone oxime-O-propylsulfonate; 2,2,2-trifluoro-1-(4-(3-(4-(2,2,2-trifluoro-1-(trifluoromethanesulfonyloxyimino)-ethyl)-phenoxy)-propoxy)-phenyl)ethanone oxime-(trifluoromethanesulfonate); 2,2,2-trifluoro-1-(4-(3-(4-(2,2,2-trifluoro-1-(1-propanesulfonyloxyimino)-ethyl)-phenoxy)-propoxy)-phenyl)ethanone oxime(1-propanesulfonate); and 2,2,2-trifluoro-1-(4-(3-(4-(2,2,2-trifluoro-1-(1-butane-sulfonyloxyimino)-ethyl)-phenoxy)-propoxy)-phenyl)ethanone oxime(1-butanesulfonate). Also included are the oxime sulfonates described in U.S. Pat. No. 6,916,591, for example, 2,2,2-trifluoro-1-(4-(3-(4-(2,2,2-trifluoro-1-(4-(4-methyl-phenylsulfonyloxy)phenylsulfonyloxyimino)-ethyl)-phenoxy)-propoxy)-phenyl)ethanone oxime(4-(4-methylphenylsulfonyloxy)-phenylsulfonate) and 2,2,2-trifluoro-1-(4-(3-(4-(2,2,2-trifluoro-1-(2,5-bis(4-methylphenylsulfonyloxy)benzene-sulfonyloxy)phenylsulfonyloxyimino)-ethyl)-phenoxy)-propoxy)-phenyl)ethanone oxime(2,5-bis(4-methylphenylsulfonyloxy)-benzenesulfonyloxy)phenylsulfonate).

Also included are the oxime sulfonates described in JP-A 9-95479 and JP-A 9-230588 and the references cited therein, for example, α-(p-toluenesulfonyloxyimino)-phenylacetonitrile, α-(p-chlorobenzenesulfonyloxyimino)-phenylacetonitrile, α-(4-nitrobenzenesulfonyloxyimino)-phenylacetonitrile, α-(4-nitro-2-trifluoromethylbenzenesulfonyloxyimino)-phenylacetonitrile, α-(benzenesulfonyloxyimino)-4-chlorophenylacetonitrile, α-(benzenesulfonyloxyimino)-2,4-dichlorophenylacetonitrile, α-(benzenesulfonyloxyimino)-2,6-dichlorophenylacetonitrile, α-(benzenesulfonyloxyimino)-4-methoxyphenylacetonitrile, α-(2-chlorobenzenesulfonyloxyimino)-4-methoxyphenylacetonitrile, α-(benzenesulfonyloxyimino)-2-thienylacetonitrile, α-(4-dodecylbenzenesulfonyloxyimino)-phenylacetonitrile, α-[(4-toluenesulfonyloxyimino)-4-methoxyphenyl]acetonitrile, α-[(dodecylbenzenesulfonyloxyimino)-4-methoxyphenyl]acetonitrile, α-(tosyloxyimino)-3-thienylacetonitrile, α-(methylsulfonyloxyimino)-1-cyclopentenylacetonitrile, α-(ethylsulfonyloxyimino)-1-cyclopentenylacetonitrile, α-(isopropylsulfonyloxyimino)-1-cyclopentenylacetonitrile, α-(n-butylsulfonyloxyimino)-1-cyclopentenylacetonitrile, α-(ethylsulfonyloxyimino)-1-cyclohexenylacetonitrile, α-(isopropylsulfonyloxyimino)-1-cyclohexenylacetonitrile, and α-(n-butylsulfonyloxyimino)-1-cyclohexenylacetonitrile.

Also included are oxime sulfonates having the following formula as described, for example, in WO 2004/074242.

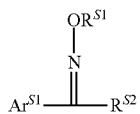

Herein $R^{s1}$ is a substituted or unsubstituted $C_1$-$C_{10}$ haloalkyl-sulfonyl or halobenzenesulfonyl group, $R^{s2}$ is a $C_1$-$C_{11}$ haloalkyl group, and $Ar^{s1}$ is substituted or unsubstituted aromatic or hetero-aromatic group. Suitable oxime sulfonates include 2-[2,2,3,3,4,4,5,5-octafluoro-1-(nonafluorobutylsulfonyloxyimino)-pentyl]-fluorene, 2-[2,2,3,3,4,4-pentafluoro-1-(nonafluorobutylsulfonyloxyimino)-butyl]-fluorene, 2-[2,2,3,3,4,4,5,5,6,6-decafluoro-1-(nonafluorobutylsulfonyloxyimino)-hexyl]-fluorene, 2-[2,2,3,3,4,4,5,5-octafluoro-1-(nonafluorobutylsulfonyloxyimino)-pentyl]-4-biphenyl, 2-[2,2,3,3,4,4-pentafluoro-1-(nonafluorobutylsulfonyloxyimino)-butyl]-4-biphenyl, and 2-[2,2,3,3,4,4,5,5,6,6-decafluoro-1-(nonafluorobutylsulfonyloxyimino)-hexyl]-4-biphenyl.

Suitable bisoxime sulfonates include those described in JP-A 9-208554, for example, bis(α-(4-toluenesulfonyloxy)imino)-p-phenylenediacetonitrile, bis(α-(benzenesulfonyloxy)imino)-p-phenylenediacetonitrile, bis(α-(methanesulfonyloxy)imino)-p-phenylenediacetonitrile, bis(α-(butanesulfonyloxy)imino)-p-phenylenediacetonitrile, bis(α-(10-camphorsulfonyloxy)imino)-p-phenylenediacetonitrile, bis(α-(4-toluenesulfonyloxy)imino)-p-phenylenediacetonitrile, bis(α-(trifluoromethanesulfonyloxy)imino)-p-phenylenediacetonitrile, bis(α-(4-methoxybenzenesulfonyloxy)imino)-p-phenylenediacetonitrile, bis(α-(4-toluenesulfonyloxy)imino)-m-phenylenediacetonitrile, bis(α-(benzenesulfonyloxy)imino)-m-phenylenediacetonitrile, bis(α-(methanesulfonyloxy)imino)-m-phenylenediacetonitrile, bis(α-(butanesulfonyloxy)imino)-m-phenylenediacetonitrile, bis(α-(10-camphorsulfonyloxy)imino)-m-phenylenediacetonitrile, bis(α-(4-toluenesulfonyloxy)imino)-m-phenylenediacetonitrile, bis(α-(trifluoromethanesulfonyloxy)imino)-m-phenylenediacetonitrile, bis(α-(4-methoxybenzenesulfonyloxy)imino)-m-phenylenediacetonitrile, etc.

Of these, preferred photoacid generators are sulfonium salts, bissulfonyldiazomethanes, N-sulfonyloxyimides, oxime-O-sulfonates and glyoxime derivatives. More preferred photoacid generators are sulfonium salts, bissulfonyldiazomethanes, N-sulfonyloxyimides, and oxime-O-sulfonates. Typical examples include triphenylsulfonium p-toluenesulfonate, triphenylsulfonium camphorsulfonate, triphenylsulfonium pentafluorobenzenesulfonate, triphenylsulfonium nonafluorobutanesulfonate, triphenylsulfonium 4-(4'-toluenesulfonyloxy)benzenesulfonate, triphenylsulfonium 2,4,6-triisopropylbenzenesulfonate, 4-tert-butoxyphenyldiphenylsulfonium p-toluenesulfonate, 4-tert-butoxyphenyldiphenylsulfonium camphorsulfonate, 4-tert-butoxyphenyldiphenylsulfonium 4-(4'-toluenesulfonyloxy)benzenesulfonate, tris(4-methylphenyl)sulfonium camphorsulfonate, tris(4-tert-butylphenyl)sulfonium camphorsulfonate, 4-tert-butylphenyldiphenylsulfonium camphorsulfonate, 4-tert-butylphenyldiphenylsulfonium nonafluoro-1-butanesulfonate, 4-tert-butylphenyldiphenylsulfonium pentafluoroethyl-perfluorocyclohexanesulfonate, 4-tert-butylphenyldiphenylsulfonium perfluoro-1-octanesulfonate, triphenylsulfonium 1,1-difluoro-2-naphthyl-ethanesulfonate, triphenylsulfonium 1,1,2,2-tetrafluoro-2-(norbornan-2-yl)ethanesulfonate, bis(tert-butylsulfonyl)diazomethane, bis(cyclohexylsulfonyl)diazomethane, bis(2,4-dimethylphenylsulfonyl)diazomethane, bis(4-(n-hexyloxy)phenylsulfonyl)diazomethane, bis(2-methyl-4-(n-hexyloxy)phenylsulfonyl)diazomethane, bis(2,5-dimethyl-4-(n-hexyloxy)phenylsulfonyl)diazomethane, bis(3,5-dimethyl-4-(n-hexyloxy)phenylsulfonyl)diazomethane, bis(2-methyl-5-isopropyl-4-(n-hexyloxy)phenylsulfonyl)diazomethane, bis(4-tert-butylphenylsulfonyl)diazomethane, N-camphorsulfonyloxy-5-norbornene-2,3-dicarboxylic acid imide, N-p-toluenesulfonyloxy-5-norbornene-2,3-dicarboxylic acid imide, 2-[2,2,3,3,4,4,5,5-octafluoro-1-(nonafluorobutylsulfonyloxyimino)-pentyl]-fluorene, 2-[2,2,3,3,4,4-pentafluoro-1-(nonafluorobutylsulfonyloxyimino)-butyl]-fluorene, and 2-[2,2,3,3,4,4,5,5,6,6-decafluoro-1-(nonafluorobutylsulfonyloxyimino)-hexyl]-fluorene.

In the resist composition, an appropriate amount of the photoacid generator is, but not limited to, 0.1 to 20 parts, and especially 0.1 to 10 parts by weight per 100 parts by weight of the base resin (A). Excessive amounts of the PAG may give rise to such problems as degraded resolution and foreign matter upon development and/or resist film peeling. The PAG may be used alone or in admixture of two or more. The transmittance of the resist film can be controlled by using a PAG having a low transmittance at the exposure wavelength and adjusting the amount of the PAG added.

In the resist composition, there may be added a compound which is decomposed with an acid to generate another acid, that is, acid-amplifier compound. For these compounds, reference should be made to J. Photopolym. Sci. and Tech., 8, 43-44, 45-46 (1995), and ibid., 9, 29-30 (1996).

Examples of the acid-amplifier compound include tert-butyl-2-methyl-2-tosyloxymethyl acetoacetate and 2-phenyl-2-(2-tosyloxyethyl)-1,3-dioxolane, but are not limited thereto. Of well-known photoacid generators, many of those compounds having poor stability, especially poor thermal stability exhibit an acid amplifier-like behavior.

In the resist composition, an appropriate amount of the acid-amplifier compound is up to 2 parts, and preferably up to 1 part by weight per 100 parts by weight of the base resin (A). Excessive amounts of the acid amplifier compound make diffusion control difficult, leading to degradation of resolution and pattern profile.

Organic Solvent

The organic solvent (C) used herein may be any organic solvent in which the base resin, acid generator, and other components are soluble. Illustrative, non-limiting, examples of the organic solvent include ketones such as cyclohexanone and methyl amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone. These solvents may be used alone or in combinations of two or more thereof. Of the above organic solvents, it is recommended to use diethylene glycol dimethyl ether, 1-ethoxy-2-propanol, PGMEA, and mixtures thereof because the acid generator is most soluble therein.

An appropriate amount of the organic solvent used is 200 to 1,000 parts, especially 400 to 800 parts by weight per 100 parts by weight of the base resin (A).

N-Containing Compound

In the resist composition, an organic nitrogen-containing compound or compounds may be compounded as component (D). The organic nitrogen-containing compound used herein is preferably a compound capable of suppressing the rate of diffusion when the acid generated by the acid generator diffuses within the resist film. The inclusion of organic nitrogen-containing compound holds down the rate of acid diffusion within the resist film, resulting in better resolution. In addition, it suppresses changes in sensitivity following exposure and reduces substrate and environment dependence, as well as improving the exposure latitude and the pattern profile.

Suitable organic nitrogen-containing compounds include primary, secondary, and tertiary aliphatic amines, mixed amines, aromatic amines, heterocyclic amines, nitrogen-containing compounds having carboxyl group, nitrogen-containing compounds having sulfonyl group, nitrogen-containing compounds having hydroxyl group, nitrogen-containing compounds having hydroxyphenyl group, alcoholic nitrogen-containing compounds, amide derivatives, imide derivatives, and carbamate derivatives.

Examples of suitable primary aliphatic amines include ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of suitable secondary aliphatic amines include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Examples of suitable tertiary aliphatic amines include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic and heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 4-pyrrolidinopyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, auinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable nitrogen-containing compounds having carboxyl group include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Examples of suitable nitrogen-containing compounds having sulfonyl group include 3-pyridinesulfonic acid and pyridinium p-toluenesulfonate. Examples of suitable nitrogen-containing compounds having hydroxyl group, nitrogen-containing compounds having hydroxyphenyl group, and alcoholic nitrogen-containing compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Examples of suitable amide derivatives include formamide, N-methylformamide, N,N-dimethylformamide, acetamide, N-methylacetamide, N,N-dimethylacetamide, propionamide, benzamide, and 1-cyclohexylpyrrolidone. Suitable imide derivatives include phthalimide, succinimide, and maleimide. Suitable carbamate derivatives include N-t-butoxycarbonyl-N,N-dicyclohexylamine, N-t-butoxycarbonylbenzimidazole and oxazolidinone.

In addition, organic nitrogen-containing compounds of the following general formula (B)-1 may also be included alone or in admixture.

$$N(X)_n(Y)_{3-n} \quad (B)\text{-}1$$

In the formula, n is equal to 1, 2 or 3; side chain Y is independently hydrogen or a straight, branched or cyclic $C_1$-$C_{20}$ alkyl group which may contain an ether or hydroxyl group; and side chain X is independently selected from groups of the following general formulas (X)-1 to (X)-3, and two or three X's may bond together to form a ring.

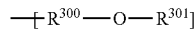
(X)-1

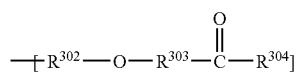
(X)-2

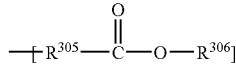
(X)-3

In the formulas, $R^{300}$, $R^{302}$ and $R^{305}$ are independently straight or branched $C_1$-$C_4$ alkylene groups; $R^{301}$ and $R^{304}$ are independently hydrogen or a straight, branched or cyclic $C_1$-$C_{20}$ alkyl group which may contain one or more hydroxyl, ether, ester groups or lactone rings; $R^{303}$ is a single bond or a straight or branched $C_1$-$C_4$ alkylene group; and $R^{306}$ is a straight, branched or cyclic $C_1$-$C_{20}$ alkyl group which may contain one or more hydroxyl, ether, ester groups or lactone rings.

Illustrative examples of the compounds of formula (B)-1 include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, 1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)amine, tris(2-pivaloyloxyethyl)amine, N,N-bis(2-acetoxyethyl)-2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxycarbonylmethyl)oxyethyl]amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl)amine, N,N-bis(2-hydroxyethyl)-2-(methoxycarbonyl)ethylamine, N,N-bis(2-acetoxyethyl)-2-(methoxycarbonyl)ethylamine, N,N-bis(2-hydroxyethyl)-2-(ethoxycarbonyl)ethylamine, N,N-bis(2-acetoxyethyl)-2-(ethoxycarbonyl)ethylamine, N,N-bis(2-hydroxyethyl)-2-(2-methoxyethoxycarbonyl)ethylamine, N,N-bis(2-acetoxyethyl)-2-(2-methoxyethoxycarbonyl)ethylamine, N,N-bis (2-hydroxyethvl)-2-(2-hydroxyethoxycarbonyl)ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]ethylamine, N,N-bis(2-acetoxyethyl)-2-[(methoxycarbonyl)methoxycarbonyl]ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl)ethylamine, N,N-bis(2-acetoxyethyl)-2-(tetrahydrofurfuryloxycarbonyl)ethylamine, N,N-bis(2-hydroxyethyl)-2-[(2-oxotetrahydrofuran-3-yl)oxy-carbonyl]ethylamine, N,N-bis(2-acetoxyethyl)-2-[(2-oxotetrahydrofuran-3-yl)oxy-carbonyl]ethylamine, N,N-bis(2-hydroxyethyl)-2-(4-hydroxybutoxycarbonyl)ethylamine, N,N-bis(2-formyloxyethyl)-2-(4-formyloxybutoxycarbonyl)ethylamine, N,N-bis(2-formyloxyethyl)-2-(2-formyloxyethoxycarbonyl)ethylamine, N,N-bis(2-methoxyethyl)-2-(methoxycarbonyl)ethylamine, N-(2-hydroxyethyl)-bis[2-(methoxycarbonyl)ethyl]amine, N-(2-acetoxyethyl)-bis[2-(methoxycarbonyl)ethyl]amine, N-(2-hydroxyethyl)-bis[2-(ethoxycarbonyl)ethyl]amine, N-(2-acetoxyethyl)-bis[2-(ethoxycarbonyl)ethyl]amine, N-(3-hydroxy-1-propyl)-bis[2-(methoxycarbonyl)ethyl]amine, N-(3-acetoxy-1-propyl)- bis[2-(methoxycarbonyl)ethyl]amine, N-(2-methoxyethyl)-bis[2-(methoxycarbonyl)ethyl]amine, N-butyl-bis[2-(methoxycarbonyl)ethyl]amine, N-butyl-bis[2-(2-methoxyethoxycarbonyl)ethyl]amine, N-methyl-bis(2-acetoxyethyl)amine, N-ethyl-bis(2-acetoxyethyl)amine, N-methyl-bis(2-pivaloyloxyethyl)amine, N-ethyl-bis[2-(methoxycarbonyloxy)ethyl]amine, N-ethyl-bis[2-(tert-butoxycarbonyloxy)ethyl]amine, tris(methoxycarbonylmethyl)amine, tris(ethoxycarbonylmethyl)amine, N-butyl-bis(methoxycarbonylmethyl)amine, N-hexyl-bis(methoxycarbonylmethyl)amine, and β-(diethylamino)-δ-valerolactone.

Also useful are one or more organic nitrogen-containing compounds having cyclic structure represented by the following general formula (B)-2.

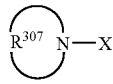
(B)-2

Herein X is as defined above, and $R^{307}$ is a straight or branched $C_2$-$C_{20}$ alkylene group which may contain one or more carbonyl, ether, ester or sulfide groups.

Illustrative examples of the organic nitrogen-containing compounds having formula (B)-2 include 1-[2-(methoxymethoxy)ethyl]pyrrolidine, 1-[2-(methoxymethoxy)ethyl]piperidine, 4-[2-(methoxymethoxy)ethyl]morpholine, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, 2-(1-pyrrolidinyl)ethyl acetate, 2-piperidinoethyl acetate, 2-morpholinoethyl acetate, 2-(1-pyrrolidinyl)ethyl formate, 2-piperidinoethyl propionate, 2-morpholinoethyl acetoxyacetate, 2-(1-pyrrolidinyl)ethyl methoxyacetate, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, methyl 3-(1-pyrrolidinyl)propionate, methyl 3-piperidinopropionate, methyl 3-morpholinopropionate, methyl 3-(thiomorpholino)propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl)propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl)methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, 2-methoxyethyl morpholinoacetate, 2-morpholinoethyl 2-methoxyacetate, 2-morpholinoethyl 2-(2-methoxyethoxy)acetate, 2-morpholinoethyl 2-[2-(2-methoxyethoxy)ethoxy]acetate, 2-morpholinoethyl hexanoate, 2-morpholinoethyl octanoate, 2-morpholinoethyl decanoate, 2-morpholinoethyl laurate, 2-morpholinoethyl myristate, 2-morpholinoethyl palmitate, and 2-morpholinoethyl stearate.

Also, one or more organic nitrogen-containing compounds having cyano group represented by the following general formulae (B)-3 to (B)-6 may be blended.

(B)-3

(B)-4

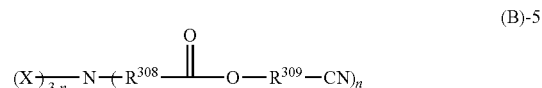
(B)-5

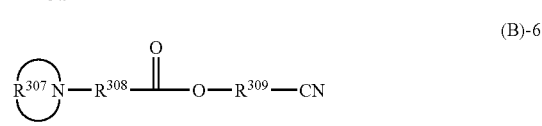
(B)-6

Herein, X, $R^{307}$ and n are as defined above, and $R^{308}$ and $R^{309}$ are each independently a straight or branched $C_1$-$C_4$ alkylene group.

Illustrative examples of the organic nitrogen-containing compounds having cyano represented by formulae (B)-3 to (B)-6 include 3-(diethylamino)propiononitrile, N,N-bis(2-hydroxyethyl)-3-aminopropiononitrile, N,N-bis(2-acetoxyethyl)-3-aminopropiononitrile, N,N-bis(2-formyloxyethyl)-3-aminopropiononitrile, N,N-bis(2-methoxyethyl)-3-aminopropiononitrile, N,N-bis[2-(methoxymethoxy)ethyl]-3-aminopropiononitrile, methyl N-(2-cyanoethyl)-N-(2-methoxyethyl)-3-aminopropionate, methyl N-(2-cyanoethyl)-N-(2-hydroxyethyl)-3-aminopropionate, methyl N-(2-acetoxyethyl)-N-(2-cyanoethyl)-3-aminopropionate, N-(2-cyanoethyl)-N-ethyl-3-aminopropiononitrile, N-(2-cyanoethyl)-N-(2-hydroxyethyl)-3-aminopropiononitrile, N-(2-acetoxyethyl)-N-(2-cyanoethyl)-3-aminopropiononitrile, N-(2-cyanoethyl)-N-(2-formyloxyethyl)-3-aminopropiononitrile, N-(2-cyanoethyl)-N-(2-methoxyethyl)-3-aminopropiononitrile, N-(2-cyanoethyl)-N-[2-(methoxymethoxy)ethyl]-3-aminopropiononitrile, N-(2-cyanoethyl)-N-(3-hydroxy-1-propyl)-3-aminopropiononitrile, N-(3-acetoxy-1-propyl)-N-(2-cyanoethyl)-3-aminopropiononitrile, N-(2-cyanoethyl)-N-(3-formyloxy-1-propyl)-3-aminopropiononitrile, N-(2-cyanoethyl)-N-tetrahydrofurfuryl-3-aminopropiononitrile, N,N-bis(2-cyanoethyl)-3-aminopropiononitrile, diethylaminoacetonitrile, N,N-bis(2-hydroxyethyl)aminoacetonitrile, N,N-bis(2-acetoxyethyl)aminoacetonitrile, N,N-bis(2-formyloxyethyl)aminoacetonitrile, N,N-bis(2-methoxyethyl)aminoacetonitrile, N,N-bis[2-(methoxymethoxy)ethyl]aminoacetonitrile, methyl N-cyanomethyl-N-(2-methoxyethyl)-3-aminopropionate, methyl N-cyanomethyl-N-(2-hydroxyethyl)-3-aminopropionate, methyl N-(2-acetoxyethyl)-N-cyanomethyl-3-aminopropionate N-cyanomethyl-N-(2-hydroxyethyl)aminoacetonitrile, N-(2-acetoxyethyl)-N-(cyanomethyl)aminoacetonitrile, N-cyanomethyl-N-(2-formyloxyethyl)aminoacetonitrile, N-cyanomethyl-N-(2-methoxyethyl)aminoacetonitrile, N-cyanomethyl-N-[2-(methoxymethoxy)ethyl]aminoacetonitrile, N-cyanomethyl-N-(3-hydroxy-1-propyl)aminoacetonitrile, N-(3-acetoxy-1-propyl)-N-(cyanomethyl)aminoacetonitrile, N-cyanomethyl-N-(3-formyloxy-1-propyl)aminoacetonitrile, N,N-bis(cyanomethyl)aminoacetonitrile, 1-pyrrolidinepropiononitrile, 1-piperidinepropiononitrile, 4-morpholinepropiononitrile, 1-pyrrolidineacetonitrile, 1-piperidineacetonitrile, 4-morpholineacetonitrile, cyanomethyl 3-diethylaminopropionate, cyanomethyl N,N-bis(2-hydroxyethyl)-3-aminopropionate, cyanomethyl N,N-bis(2-acetoxyethyl)-3-aminopropionate, cyanomethyl N,N-bis(2-formyloxyethyl)-3-aminopropionate, cyanomethyl N,N-bis(2-methoxyethyl)-3-aminopropionate, cyanomethyl N,N-bis[2-(methoxymethoxy)ethyl]-3-aminopropionate,
2-cyanoethyl 3-diethylaminopropionate, 2-cyanoethyl N,N-bis(2-hydroxyethyl)-3-aminopropionate, 2-cyanoethyl N,N-bis(2-acetoxyethyl)-3-aminopropionate, 2-cyanoethyl N,N-bis(2-formyloxyethyl)-3-aminopropionate, 2-cyanoethyl N,N-bis(2-methoxyethyl)-3-aminopropionate, 2-cyanoethyl N,N-bis[2-(methoxymethoxy)ethyl]-3-aminopropionate, cyanomethyl 1-pyrrolidinepropionate, cyanomethyl 1-piperidinepropionate, cyanomethyl 4-morpholinepropionate, 2-cyanoethyl 1-pyrrolidinepropionate, 2-cyanoethyl 1-piperidinepropionate, and 2-cyanoethyl 4-morpholinepropionate.

Also included are organic nitrogen-containing compounds of imidazole structure having a polar functional group, represented by the general formula (B)-7.

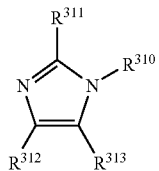

(B)-7

Herein, $R^{310}$ is a straight, branched or cyclic $C_2$-$C_{20}$ alkyl group bearing at least one polar functional group selected from among hydroxyl, carbonyl, ester, ether, sulfide, carbonate, cyano and acetal groups; $R^{311}$, $R^{312}$ and $R^{313}$ are each independently hydrogen, a straight, branched or cyclic $C_1$-$C_{10}$ alkyl group, aryl group or aralkyl group.

Also included are organic nitrogen-containing compounds of benzimidazole structure having a polar functional group, represented by the general formula (B)-8.

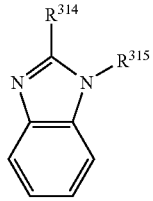

(B)-8

Herein, $R^{314}$ is hydrogen, a straight, branched or cyclic $C_1$-$C_{10}$ alkyl group, aryl group or aralkyl group. $R^{315}$ is a polar functional group-bearing, straight, branched or cyclic $C_1$-$C_{20}$ alkyl group, and the alkyl group contains as the polar functional group at least one group selected from among ester, acetal and cyano groups, and may additionally contain at least one group selected from among hydroxyl, carbonyl, ether, sulfide and carbonate groups.

Further included are heterocyclic nitrogen-containing compounds having a polar functional group, represented by the general formulae (B)-9 and (B)-10.

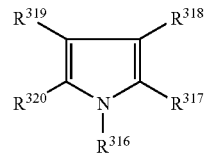

(B)-9

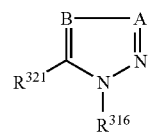

(B)-10

Herein, A is a nitrogen atom or $=C-R^{322}$, B is a nitrogen atom or $=C-R^{323}$, $R^{316}$ is a straight, branched or cyclic $C_2$-$C_{20}$ alkyl group bearing at least one polar functional group selected from among hydroxyl, carbonyl, ester, ether, sulfide, carbonate, cyano and acetal groups; $R^{317}$, $R^{318}$, $R^{319}$ and $R^{320}$ are each independently hydrogen, a straight, branched or cyclic $C_1$-$C_{10}$ alkyl group or aryl group, or a pair of $R^{317}$ and $R^{318}$ and a pair of $R^{319}$ and $R^{320}$, taken together, may form a benzene, naphthalene or pyridine ring with the carbon atoms to which they are attached; $R^{321}$ is hydrogen, a straight, branched or cyclic $C_1$-$C_{10}$ alkyl group or aryl group; $R^{322}$ and $R^{323}$ each are hydrogen, a straight, branched or cyclic $C_1$-$C_{10}$ alkyl group or aryl group, or a pair of $R^{321}$ and $R^{323}$, taken together, may form a benzene or naphthalene ring with the carbon atoms to which they are attached.

Also included are organic nitrogen-containing compounds of aromatic carboxylic ester structure having the general formulae (B)-11 to (B)-14.

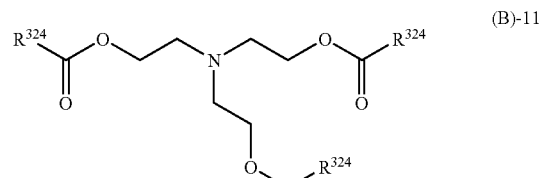

(B)-11

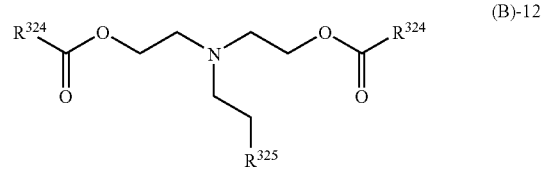

(B)-12

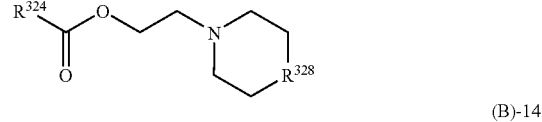

(B)-13

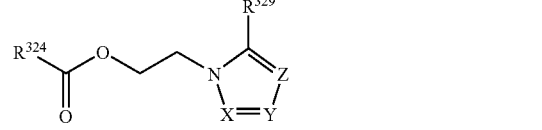

(B)-14

Herein $R^{324}$ is a $C_6$-$C_{20}$ aryl group or $C_4$-$C_{20}$ hetero-aromatic group, in which some or all hydrogen atoms may be replaced by halogen atoms, straight, branched or cyclic $C_1$-$C_{20}$ alkyl groups, $C_6$-$C_{20}$ aryl groups, $C_7$-$C_{20}$ aralkyl groups, $C_1$-$C_{20}$ alkoxy groups, $C_1$-$C_{10}$ acyloxy groups or $C_1$-$C_{10}$ alkylthio groups. $R^{325}$ is $CO_2R^{326}$, $OR^{327}$ or cyano group. $R^{326}$ is a $C_1$-$C_{10}$ alkyl group, in which some methylene groups may be replaced by oxygen atoms. $R^{327}$ is a $C_1$-$C_{10}$ alkyl or acyl group, in which some methylene groups may be replaced by oxygen atoms. $R^{328}$ is a single bond, methylene, ethylene, sulfur atom or —$O(CH_2CH_2O)_n$— group wherein n is 0, 1, 2, 3 or 4. $R^{329}$ is hydrogen, methyl, ethyl or phenyl. X is a nitrogen atom or $CR^{330}$. Y is a nitrogen atom or $CR^{331}$. Z is a nitrogen atom or $CR^{332}$. $R^{330}$, $R^{331}$ and $R^{332}$ are each independently hydrogen, methyl or phenyl. Alternatively, a pair of $R^{330}$ and $R^{331}$ or a pair of $R^{331}$ and $R^{332}$ may bond together to form a $C_6$-$C_{20}$ aromatic ring or $C_2$-$C_{20}$ hetero-aromatic ring with the carbon atoms to which they are attached.

Further included are organic nitrogen-containing compounds of 7-oxanorbornane-2-carboxylic ester structure having the general formula (B)=15.

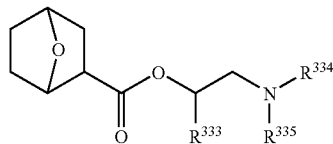

(B)-15

Herein $R^{333}$ is hydrogen or a straight, branched or cyclic $C_1$-$C_{10}$ alkyl group. $R^{334}$ and $R^{335}$ are each independently a $C_1$-$C_{20}$ alkyl group, $C_6$-$C_{20}$ aryl group or $C_7$-$C_{20}$ aralkyl group, which may contain one or more polar functional groups selected from among ether, carbonyl, ester, alcohol, sulfide, nitrile, amine, imine, and amide and in which some hydrogen atoms may be replaced by halogen atoms. $R^{334}$ and $R^{335}$, taken together, may form a heterocyclic or hetero-aromatic ring of 2 to 20 carbon atoms with the nitrogen atom to which they are attached.

The organic nitrogen-containing compounds may be used alone or in admixture of two or more. The organic nitrogen-containing compound is preferably formulated in an amount of 0.001 to 2 parts, and especially 0.01 to 1 part by weight, per 100 parts by weight of the base resin (B). Less than 0.001 phr of the nitrogen-containing compound fails to achieve the desired addition effect whereas more than 2 phr may lead to too low sensitivity.

The resist composition of the invention may include optional ingredients, for example, (E) a surfactant which is commonly used for improving the coating characteristics. Optional ingredients may be added in conventional amounts so long as this does not compromise the objects of the invention.

Nonionic surfactants are preferred, examples of which include perfluoroalkylpolyoxyethylene ethanols, fluorinated alkyl esters, perfluoroalkylamine oxides, perfluoroalkyl EO-addition products, and fluorinated organosiloxane compounds. Useful surfactants are commercially available under the trade names Fluorad FC-430 and FC-431 from Sumitomo 3M, Ltd., Surflon S-141, S-145, KH-10, KH-20, KH-30 and KH-40 from Asahi Glass Co., Ltd., Unidyne DS-401, DS-403 and DS-451 from Daikin Industry Co., Ltd., Megaface F-8151 from Dai-Nippon Ink & Chemicals, Inc., and X-70-092 and X-70-093 from Shin-Etsu Chemical Co., Ltd. Preferred surfactants are Fluorad FC-430 from Sumitomo 3M, Ltd., KH-20 and KH-30 from Asahi Glass Co., Ltd., and X-70-093 from Shin-Etsu Chemical Co., Ltd.

In the resist composition, an additive polymer may be added as another optional ingredient. This additive polymer tends to segregate in the sub-surface region of the resist film and has the functions of tailoring the hydrophilic/hydrophobic balance of the surface, enhancing water repellency, and/or preventing low-molecular-weight fractions from flowing into or out of the resist film when the resist film is in contact with water or another liquid. Such a segregating polymer may be added in conventional amounts as long as the objects of the invention are not compromised and preferably in an amount of up to 15 parts, and more preferably up to 10 parts by weight per 100 parts by weight of the base resin. The lower limit above which the segregating polymer can exert its effect is preferably 1 part.

The segregating polymer is preferably selected from homopolymers and copolymers comprising fluorine-containing units of one or more types, and copolymers comprising fluorine-containing units and other units. Exemplary fluorine-containing units and other units are illustrated below, but not limited thereto.

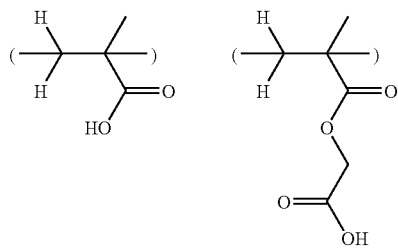

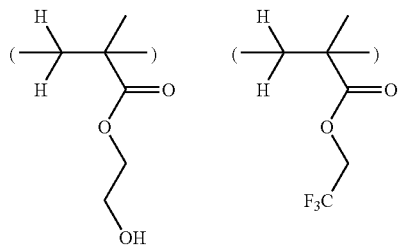

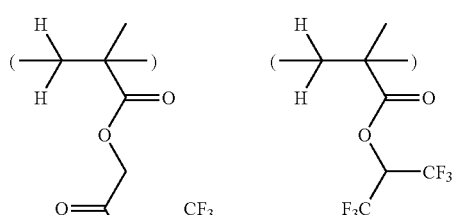

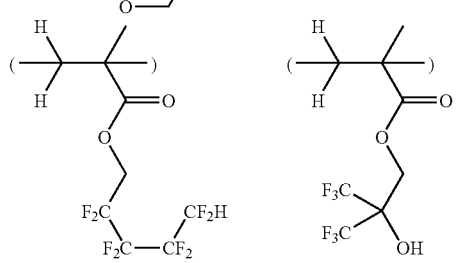

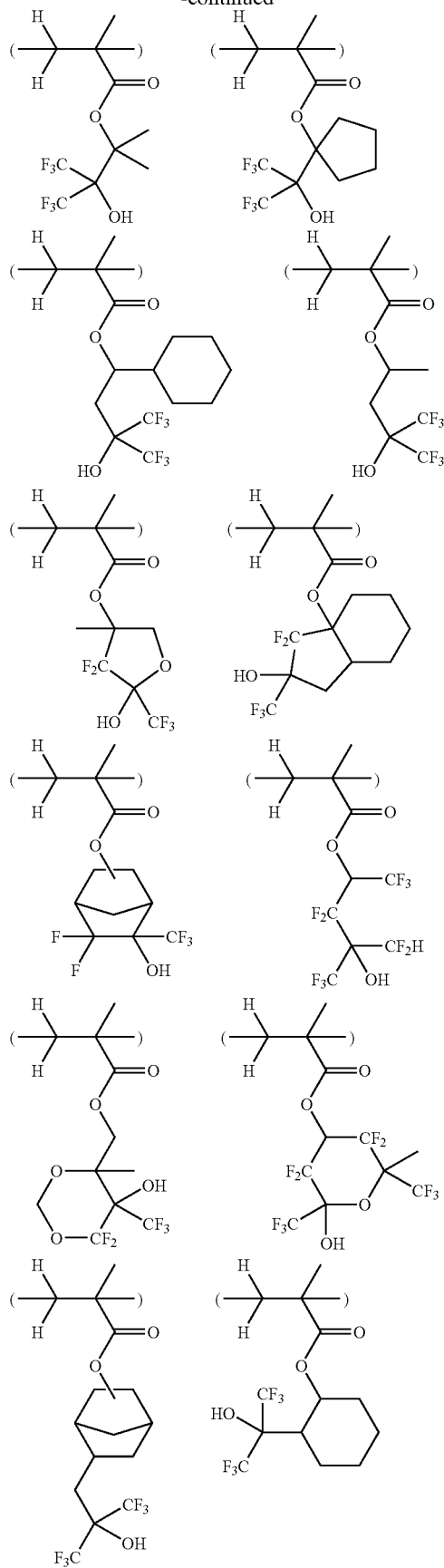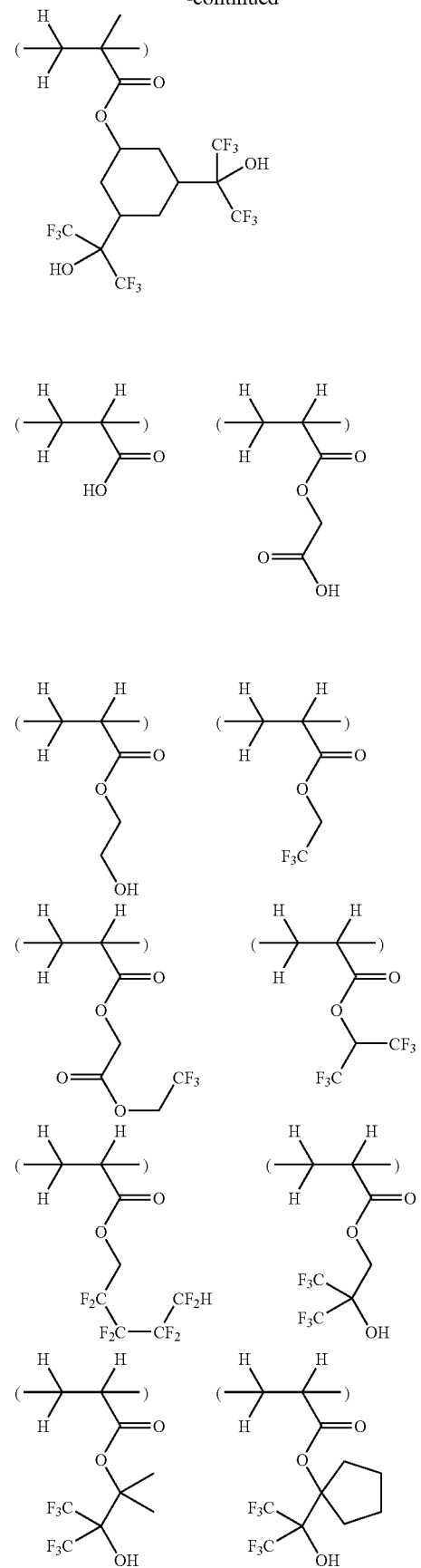

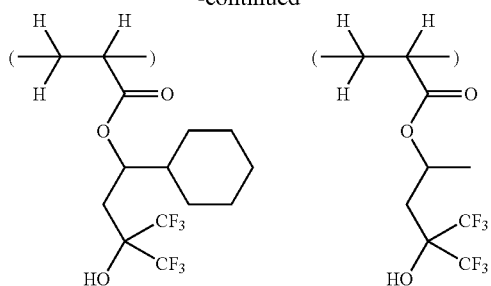
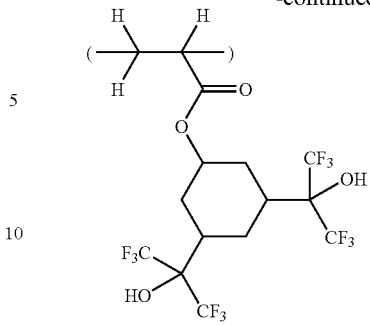
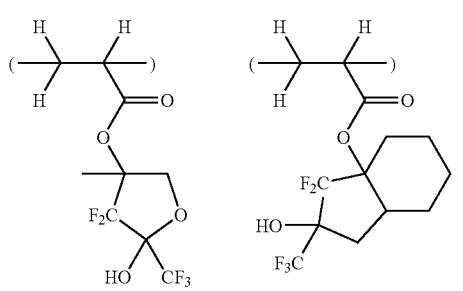
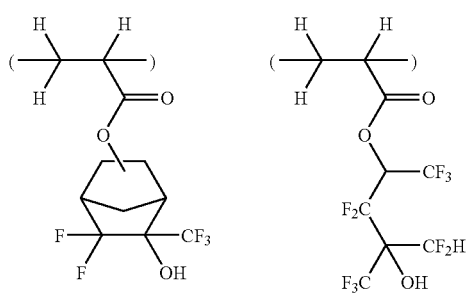
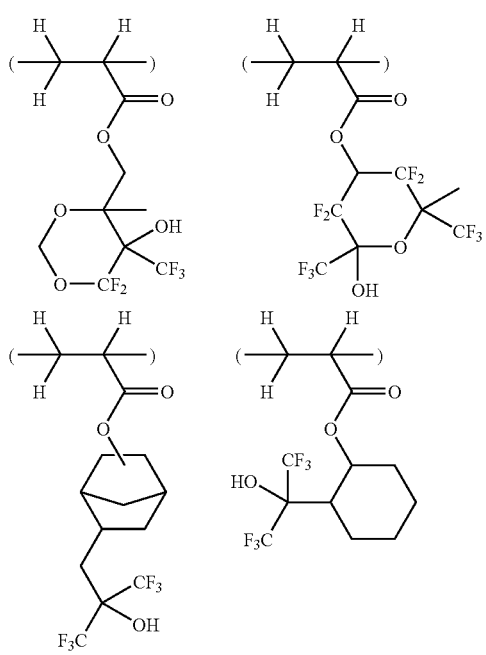

Preferably the segregating polymer has a weight average molecular weight of 1,000 to 50,000, and more preferably 2,000 to 20,000, as measured by GPC versus polystyrene standards. Outside the range, the surface modifying effect may be insufficient or development defects may form.

While the resist composition of the invention typically comprises a polymer or base resin, acid generator, organic solvent and nitrogen-containing compound as described above, there may be added optional other ingredients such as dissolution inhibitors, acidic compounds, stabilizers, and dyes. Optional ingredients may be added in conventional amounts so long as this does not compromise the objects of the invention.

Process

Pattern formation using the resist composition of the invention may be performed by well-known lithography processes. The process generally involves coating, heat treatment (or prebaking), exposure, heat treatment (post-exposure baking, PEB), and development. If necessary, any additional steps may be added.

For pattern formation, the resist composition is first applied onto a substrate (on which an integrated circuit is to be formed, e.g., Si, SiO$_2$, SiN, SiON, TiN, WSi, BPSG, SOG, organic antireflective coating, Cr, CrO, CrON, MoSi, etc.) by a suitable coating technique such as spin coating, roll coating, flow coating, dip coating, spray coating or doctor coating. The coating is prebaked on a hot plate at a temperature of 50 to 150° C. for 1 to 10 minutes, preferably 60 to 140° C. for 1 to 5 minutes. The resulting resist film is generally 0.01 to 2.0 µm thick.

A relationship of a reduced thickness of resist film to an etch selectivity ratio between resist film and processable substrate imposes severer limits on the process. Under consideration is the tri-layer process in which a resist layer, a silicon-containing intermediate layer, an undercoat layer having a high carbon density and high etch resistance, and a processable substrate are laminated in sequence from top to bottom. On etching with oxygen gas, hydrogen gas, ammonia gas or the like, a high etch selectivity ratio is available between the silicon-containing intermediate layer and the undercoat layer, which allows for thickness reduction of the silicon-containing intermediate layer. A relatively high etch selectivity ratio is also available between the monolayer resist and the silicon-containing intermediate layer, which allows for thickness reduction of the monolayer resist. The method for forming the undercoat layer in this case includes a coating and baking method and a CVD method. In the case of coating, novolac resins and resins obtained by polymerization of fused ring-containing olefins are used. In the CVD film formation, reactant gases such as butane, ethane, propane, ethylene and acetylene are used. For the silicon-containing intermediate layer, either a coating method or a CVD method may be employed. The coating method uses silsesquioxane, polyhedral oligomeric silsesquioxane (POSS) and the like while the CVD method uses silane gases as the reactant. The silicon-containing intermediate layer may have an antireflection function with a light absorbing ability and have photo-absorptive groups like phenyl groups, or it may be a SiON film. An organic film may be formed between the silicon-containing intermediate layer and the photoresist, and the organic film in this case may be an organic antireflective coating. After the photoresist film is formed, deionized water rinsing (or post-soaking) may be carried out for extracting the photoacid generator and the like from the film surface or washing away particles, or a protective film may be coated.

With a mask having a desired pattern placed above the resist film, the resist film is then exposed to radiation such as UV, deep-UV, electron beam, x-ray, excimer laser light, γ-ray and synchrotron radiation. The exposure dose is preferably about 1 to 200 mJ/cm$^2$, more preferably about 10 to 100 mJ/cm$^2$. The film is further baked on a hot plate at 60 to 150° C. for 1 to 5 minutes, preferably 80 to 120° C. for 1 to 3 minutes (post-exposure baking=PEB). Thereafter the resist film is developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle and spray techniques. In this way, a desired resist pattern is formed on the substrate. It is appreciated that the resist composition of the invention is suited for nano-scale patterning using such high-energy radiation as deep UV with a wavelength of 254 to 193 nm, vacuum UV with a wavelength of 157 nm, electron beam, soft x-ray, x-ray, excimer laser light γ-ray and synchrotron radiation, and best suited for nano-scale patterning using high-energy radiation in the wavelength range of 180 to 200 nm.

Immersion lithography can be applied to the resist composition of the invention. The ArF immersion lithography uses a liquid having a refractive index of at least 1 and highly transparent at the exposure wavelength such as deionized water or alkanes as the immersion solvent. The immersion lithography involves prebaking a resist film and exposing the resist film to light through a projection lens, with deionized water or similar liquid interposed between the resist film and the projection lens. Since this allows projection lenses to be designed to a numerical aperture (NA) of 1.0 or higher, formation of finer size patterns is possible. The immersion lithography is important for the ArF lithography to survive to the 45-nm node, with a further development thereof being accelerated. In the case of immersion lithography, deionized water rinsing (or post-soaking) may be carried out after exposure for removing water droplets left on the resist film, or a protective coating may be applied onto the resist film after pre-baking, for preventing any leach-out from the resist and improving water slip on the film surface. The resist protective coating used in the immersion lithography is preferably formed from a solution of a polymer having 1,1,1,3,3,3-hexafluoro-2-propanol residue which is insoluble in water, but soluble in an alkaline developer liquid, in a solvent selected from alcohols of at least 4 carbon atoms, ethers of 8 to 12 carbon atoms, and mixtures thereof.

The water immersion lithography using a NA 1.35 lens achieves an ultimate resolution of 40 to 38 nm at the maximum NA, but cannot reach 32 nm. Efforts have been made to develop higher refractive index materials in order to further increase NA. It is the minimum refractive index among projection lens, liquid, and resist film that determines the NA limit of lenses. In the case of water immersion, the refractive index of water is the lowest in comparison with the projection lens (refractive index 1.5 for synthetic quartz) and the resist film (refractive index 1.7 for prior art methacrylate-based film). Thus the NA of projection lens is determined by the refractive index of water. Recent efforts succeeded in developing a highly transparent liquid having a refractive index of 1.65. In this situation, the refractive index of projection lens made of synthetic quartz is the lowest, suggesting a need to develop a projection lens material with a higher refractive index. LuAG (lutetium aluminum garnet Lu$_3$Al$_5$O$_{12}$) having a refractive index of at least 2 is the most promising material.

The resist composition of the invention is applicable to immersion lithography using a high refractive index liquid.

The process that now draws attention as the technology for extending the life of the ArF lithography is a double patterning process involving a first set of exposure and development to form a first pattern and a second set of exposure and development to form a second pattern between features of the first pattern. See Proc. SPIE, Vol. 5754, p1508 (2005). A number of double patterning processes have been proposed. One exemplary process involves a first set of exposure and development to form a photoresist pattern having lines and spaces at intervals of 1:3, processing the underlying layer of hard mask by dry etching, applying another layer of hard mask thereon, a second set of exposure and development of a photoresist film to form a line pattern in the spaces of the first exposure, and processing the hard mask by dry etching, thereby forming a line-and-space pattern at a half pitch of the first pattern. An alternative process involves a first set of exposure and development to form a photoresist pattern having spaces and lines at intervals of 1:3, processing the underlying layer of hard mask by dry etching, applying a photoresist layer thereon, a second set of exposure and development to form a second space pattern on the remaining hard mask portion, and processing the hard mask by dry etching. In either process, the hard mask is processed by two dry etchings.

While the former process requires two applications of hard mask, the latter process uses only one layer of hard mask, but requires to form a trench pattern which is difficult to resolve as compared with the line pattern. The latter process includes the use of a negative resist material in forming the trench pattern. This allows for use of high contrast light as in the formation of lines as a positive pattern. However, since the negative resist material has a lower dissolution contrast than the positive resist material, a comparison of the formation of lines from the positive resist material with the formation of a trench pattern of the same size from the negative resist material reveals that the resolution achieved with the negative resist material is lower. After a wide trench pattern is formed from the positive resist material by the latter process, there may be applied a thermal flow method of heating the substrate for shrinkage of the trench pattern, or a RELACS method of coating a water-soluble film on the trench pattern as developed and heating to induce crosslinking at the resist film surface for achieving shrinkage of the trench pattern. These have the drawbacks that the proximity bias is degraded and the process is further complicated, leading to reduced throughputs.

Both the former and latter processes require two etchings for substrate processing, leaving the issues of a reduced throughput and deformation and misregistration of the pattern by two etchings. One method that proceeds with a single etching is by using a negative resist material in a first exposure and a positive resist material in a second exposure. Another method is by using a positive resist material in a first exposure and a negative resist material in a higher alcohol of 4 or more carbon atoms, in which the positive resist material is not dissolvable, in a second exposure. However, these methods using negative resist materials with low resolution entail degradation of resolution.

If first exposure is followed by second exposure at a half-pitch shifted position, the optical energy of second exposure offsets the optical energy of first exposure so that the contrast becomes zero. If a contrast enhancement layer (CEL) is formed on the resist film, the incident light to the resist film becomes nonlinear so that the first and second exposures do not offset each other. Thus an image having a half pitch is formed. See Jpn. J. Appl. Phy. Vol. 33 (1994) p6874-6877. It is expected that similar effects are produced by using an acid generator capable of two photon absorption to provide a nonlinear contrast.

The critical issue associated with double patterning is an overlay accuracy between first and second patterns. Since the magnitude of misregistration is reflected by a variation of line size, an attempt to form 32-nm lines at an accuracy of 10%, for example, requires an overlay accuracy within 3.2 nm. Since currently available scanners have an overlay accuracy of the order of 8 nm, a significant improvement in accuracy is necessary.

Now under investigation is the resist pattern freezing technology involving forming a first resist pattern on a substrate, taking any suitable means for insolubilizing the resist pattern with respect to the resist solvent and alkaline developer, applying a second resist thereon, and forming a second resist pattern in space portions of the first resist pattern. With this freezing technology, etching of the substrate is required only once, leading to improved throughputs and avoiding the problem of misregistration due to stress relaxation of the hard mask during etching. In the freezing technology, development efforts are focused on the step of forming a resist film on the first resist pattern and the optical or thermal step of insolubilizing the resist pattern. The resist composition of the invention is also applicable to such a process. Examples of light used for the freezing purpose include preferably light with a wavelength of up to 300 nm, more preferably up to 200 nm, specifically ArF excimer light of wavelength 193 nm, $Xe_2$ excimer light of 172 nm, $F_2$ excimer light of 157 nm, $Kr_2$ excimer light of 146 nm, and $Ar_2$ excimer light of 126 nm, and the exposure dose in the case of light is preferably in the range of 10 mJ/cm² to 10 J/cm². Irradiation from an excimer laser of sub-200 nm wavelength, especially 193 nm, 172 nm, 157 nm, 146 nm, and 122 nm, or an excimer lamp not only causes the photoacid generator to generate an acid, but also promotes photo-induced crosslinking reaction. In a further example where a thermal acid generator in the form of an ammonium salt is added to a photoresist composition, specifically in an amount of 0.001 to 20 parts, more specifically 0.01 to 10 parts by weight per 100 parts by weight of the base resin, an acid can be generated by heating. In this case, acid generation and crosslinking reaction proceed simultaneously. The preferred heating conditions include a temperature of 100 to 300° C., and especially 130 to 250° C., and a time of 10 to 300 seconds. As a result, a crosslinked resist film is formed which is insoluble in solvents and alkaline developers.

EXAMPLE

Examples of the invention are given below by way of illustration and not by way of limitation. All parts (pbw) and percents (%) are by weight unless otherwise stated. The abbreviation "Mw" is a weight average molecular weight as measured by GPC using polystyrene standards.

Monomers within the scope of the invention were synthesized according to the following formulation.

Synthesis Example 1

Synthesis of (2-hydroxymethyl-2-adamantyl)methyl methacrylate (Monomer 1)

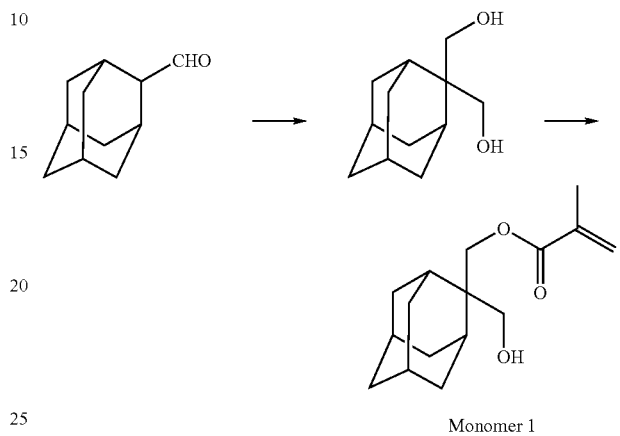

Monomer 1

Synthesis Example 1-1

Synthesis of 2,2-adamantane dimethanol

To a mixture of 283 g of 2-adamantane carbaldehyde (which had been synthesized by Darzen reaction of adamantanone with chloroacetate, hydrolysis of the resulting glycidyl ester, and subsequent heating for decarbonation), 300 g of tetrahydrofuran, and 500 ml of methanol under ice cooling, 380 g of a 37% formaldehyde aqueous solution was added and then 350 g of a 25% sodium hydroxide aqueous solution was added dropwise over 30 minutes. After the completion of dropwise addition, the ice bath was removed, and the reaction mixture was stirred for 18 hours at room temperature. The reaction mixture was poured into a saturated sodium chloride aqueous solution, which was extracted with a 1:1 tetrahydrofuran/ethyl acetate mixture. The crude product obtained by concentrating the organic layer was recrystallized from n-hexane/diethyl ether, collecting 288 g (yield 85%) of the target compound.

2,2-adamantane dimethanol colorless solid
IR (KBr disk): ν=3432, 2912, 2861, 1467, 1066, 1031, 1010 cm⁻¹
$^1$H-NMR (600 MHz in DMSO-$d_6$): δ=1.45 (4H, br.d-like, J=12.8 Hz), 1.59-1.64 (4H, m), 1.80 (2H, br.s), 1.95 (4H, br.d-like, J=12.4 Hz), 3.60 (4H, d, J=5.5 Hz), 4.19 (2H, t, J=5.5 Hz) ppm
$^{13}$C-NMR(150 MHz in DMSO-$d_6$): δ=27.67, 28.27, 32.37, 39.17, 42.38, 62.04 ppm Synthesis Example 1-2

Synthesis via route 1 of (2-hydroxymethyl-2-adamantyl)-methyl methacrylate

A mixture of 2.0 g of 2,2-adamantane dimethanol, 1.0 g of methacrylic acid, 0.19 g of p-toluenesulfonic acid monohydrate, 20 g of toluene, and 2.0 mg of 2,2'-methylene-bis(6-t-butyl-p-cresol) was heated at 120° C. for 6 hours while the water being formed was azeotroped off. After the reaction mixture resumed room temperature, 20 g of water was added to quench the reaction. The reaction solution was washed with saturated sodium hydrogen carbonate aqueous solution and saturated saline, dried over sodium sulfate, and concentrated in vacuum, obtaining 2.8 g of a crude product. It was purified by silica gel chromatography, collecting 0.4 g (yield 16%) of the target compound and 80 mg of the by-product, (2-methacryloyloxymethyl-2-adamantyl)methyl methacrylate.

(2-hydroxymethyl-2-adamantyl)methyl methacrylate colorless solid

IR (KBr disk): ν=3529, 2912, 2863, 1698, 1635, 1454, 1330, 1299, 1189, 1037, 1024, 1010, 985, 958, 941, 813, 505 cm$^{-1}$ $^1$H-NMR (600 MHz in DMSO-d$_6$): δ=1.47-1.55 (4H, m), 1.63-1.67 (4H, m), 1.81-1.85 (2H, br.s-like), 1.85-1.87 [6H, m (including 3H, s)], 1.92 (2H, br.d-like, J=11.5 Hz), 1.98 (2H, br.d-like, J=13.3 Hz), 3.60 (2H, d, J=5.5 Hz), 4.28 (1H, s), 4.43 (1H, t, J=5.0, 5.5 Hz), 5.63 (1H, t-like, J=1.5 Hz), 5.99 (1H, s-like) ppm $^{13}$C-NMR (150 MHz in DMSO-d$_6$): δ=17.98, 27.32, 27.45, 28.59, 31.99, 32.35, 38.92, 41.94, 60.40, 63.87, 125.27, 136.18, 166.56 ppm GC-MS (EI): (m/z)$^+$=27, 41, 55, 69, 91, 105, 119, 133, 148, 165, 179, 195, 218, 233, 248, 265 [(M–H)$^+$]

(2-methacryloyloxymethyl-2-adamantyl)methyl methacrylate colorless solid

IR (KBr disk): ν=2979, 2927, 2898, 2863, 1706, 1635, 1479, 1452, 1375, 1326, 1295, 1186, 1162, 1097, 1012, 973, 954, 941, 815 cm$^{-1}$ $^1$H-NMR (600 MHz in CDCl$_3$): δ=1.61-1.66 (4H, m), 1.72 (2H, br.s-like), 1.80 (2H, br.s-like), 1.89-1.93 [8H, m (including 6H, s)], 2.01-2.05 (4H, d-like, J=12.8 Hz), 4.41 (4H, s), 5.53 (2H, t-like, J=1.5 Hz), 6.06 (2H, s-like) ppm $^{13}$C-NMR (150 MHz in CDCl$_3$): δ=18.33, 27.64, 29.61, 32.56, 39.18, 41.51, 64.78, 125.50, 136.26, 167.36 ppm Synthesis Example 1-3

Synthesis Via Route 2 of (2-hydroxymethyl-2-adamantyl)-methyl methacrylate

A mixture of 100 g of 2,2-adamantane dimethanol, 48.2 g of methacrylic acid, 20 g of toluene, 25 g of acidic ion-exchange resin Amberlist-15, and 0.1 g of 2,2'-methylenebis (6-t-butyl-p-cresol) was heated at 120° C. for 6 hours while the water being formed was azeotroped off. After the reaction mixture resumed room temperature, it was filtered through Celite. The filtrate was concentrated in vacuum. 300 g of hexane was added to the concentrate for recrystallization. The crystals were recovered and dried in vacuum, obtaining 45.0 g (yield 33%) of the target compound. The spectral data of this compound were identical with those of the product in Synthesis Example 1-2.

Synthesis Example 2

Synthesis of (2-hydroxylmethyl-2-norbornyl)methyl methacrylate (Monomer 2)

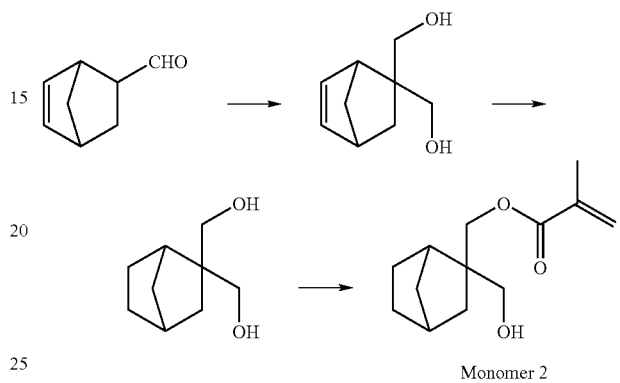

Monomer 2

Synthesis Example 2-1

Synthesis of norbornane-2,2-dimethanol

To a mixture of 364 g of 5-norbornene-2-carbaldehyde (which had been synthesized by Diels-Alder reaction of acrolein with cyclopentadiene) and 1500 ml of methanol under ice cooling, 560 g of a 37% formaldehyde aqueous solution was added and then 546 g of a 25% sodium hydroxide aqueous solution was added dropwise over 30 minutes. After the completion of dropwise addition, the ice bath was removed, and the reaction mixture was stirred for 18 hours at room temperature. The reaction mixture was concentrated by distilling off methanol under a reduced pressure. The resulting solid was dissolved in tetrahydrofuran and washed with a sodium hydroxide aqueous solution. The organic layer was concentrated in vacuum, obtaining crude 5-norbornene-2,2-dimethanol. This crude product was combined with 500 ml of tetrahydrofuran and 10 g of 5% palladium on activated carbon as a hydrogenation catalyst. Hydrogenation was carried out under a hydrogen pressure of 1.4 MPa in an autoclave which was maintained at 30-40° C. by occasional placement in a water bath. The reaction mixture was filtered of the catalyst, combined with ethyl acetate, and washed with a saturated potassium carbonate aqueous solution. The organic layer was dried over sodium sulfate and concentrated in vacuum, obtaining 435 g (yield 94%) of the target compound.

norbornane-2,2-dimethanol colorless solid

IR (KBr disk): ν=3322, 2950, 2875, 1461, 1409, 1049, 1025 cm$^{-1}$ $^1$H-NMR (600 MHz in DMSO-d$_6$): δ=0.57 (1H, dd, J=2.8, 12.4 Hz), 0.99-1.05 (1H, m), 1.06 (1H, br.d-like, J=9.63 Hz), 1.16-1.21 (1H, m), 1.12-1.29 (1H, m), 1.42-1.49 (2H, m), 1.56-1.62 (1H, m), 1.96 (1H, d-like, J=3.6 Hz), 2.11 (1H, t-like, J=4.1 Hz), 3.13 (1H, d, J=10.6 Hz), 3.22 (1H, d, J=10.5

Hz), 3.39 (1H, d, J=10.1 Hz), 3.46 (1H, d, J=10.5 Hz), 4.36 (1H, br.s), 4.47 (1H, br.s) ppm $^{13}$C-NMR (150 MHz in DMSO-d$_6$): δ=27.67, 28.27, 32.37, 39.17, 42.38, 62.04 ppm GC-MS (EI): (m/z)$^+$=41, 57, 79, 91, 107, 125, 138 [(M−H$_2$O)$^+$]

Synthesis Example 2-2

Synthesis of (2-hydroxylmethyl-2-norbornyl)methyl methacrylate

A mixture of 6.43 g of norbornane-2,2-dimethanol, 4.25 g of methacrylic acid, 0.1 g of p-toluenesulfonic acid monohydrate, 60 ml of toluene, and 2.0 mg of 4-methoxyphenol was heated at 120° C. for 6 hours while the water being formed was azeotroped off. After the reaction mixture resumed room temperature, ethyl acetate was added. The reaction solution was washed with saturated sodium hydrogen carbonate aqueous solution and saturated saline, dried over sodium sulfate, and concentrated in vacuum, obtaining 7.43 g of a crude product. It was purified by silica gel chromatography, collecting 4.64 g (yield 51%) of the target compound and 0.48 g of the by-product, (2-methacryloyloxymethyl-2-norbornyl)methyl methacrylate.

(2-hydroxymethyl-2-norbornyl)methyl methacrylate (Mixture of Approx. 1:1 Exo/Endo-Isomers)

colorless solid

IR (film): ν=3502, 2954, 2881, 1739, 1718, 1637, 1456, 1322, 1301, 1240, 1170, 1047, 1027 cm$^{-1}$ $^1$H-NMR (600 MHz in DMSO-d$_6$): δ=0.76 (1H, dd, J=2.3, 12.4 Hz), 1.12-1.16 (2H, m), 1.22-1.64 (5H, m), 1.87 (3H, s-like), 1.96-1.99 (2H, m), 2.14-2.18 (1H, m), 3.17 (0.5H, dd, J=5.6, 10.4 Hz), 3.28 (0.5H, dd, J=4.6, 10.6 Hz), 3.17 (0.5H, dd, J=5.6, 10.4 Hz), 3.35 (0.5H, dd, J=5.6, 10.5 Hz), 3.41 (0.5H, dd, J=5.1, 10.5 Hz), 3.87 (0.5H, d, J=11.0 Hz), 3.88 (0.5H, d, J=10.5 Hz), 4.03 (0.5H, d, J=11.0 Hz), 4.13 (0.5H, d, J=11.0 Hz), 4.54 (1H, t, J=5.1 Hz), 4.59 (1H, t, J=5.0 Hz), 5.63-5.65 (1H, m), 5.99-6.01 (1H, m) ppm $^{13}$C-NMR (150 MHz in DMSO-d$_6$): δ=17.92 (0.5C), 17.94 (0.5C), 23.79 (0.5C), 23.92 (0.5C), 28.13, 36.33 (0.5C), 36.41 (0.5C), 37.16 (0.5C), 37.22 (0.5C), 37.34 (0.5C), 37.40 (0.5C), 40.19 (0.5C), 40.23 (0.5C), 45.41 (0.5C), 45.48 (0.5C), 62.28 (0.5C), 63.73 (0.5C), 65.47 (0.5C), 66.48 (0.5C), 125.26 (0.5C), 125.31 (0.5C), 136.15 (1C), 166.53 (0.5C), 166.69 (0.5C) ppm GC-MS (EI): (m/z)$^+$=29, 41, 55, 69, 79, 93, 108, 120, 138

(2-methacryloyloxymethyl-2-norbornyl)methyl methacrylate colorless solid

IR (film): ν=2956, 2871, 1718, 1639, 1456, 1322, 1297, 1160, 1016 cm$^{-1}$ $^1$H-NMR (600 MHz in DMSO-d$_6$): δ=0.96 (1H, dd, J=2.3, 12.8 Hz), 1.11-1.16 (1H, m), 1.20 (1H, br.d-like, J=10.1 Hz), 1.33-1.41 (2H, m), 1.45-1.56 (2H, m), 1.60 (1H, br.d-like, J=10.1 Hz), 1.85 (3H, s-like), 1.85 (3H, s-like), 2.12 (1H, br.d-like, J=3.7 Hz), 2.21 (1H, br.t-like, J=3.6 Hz), 3.95 (1H, d, J=10.7 Hz), 3.96 (1H, d, J=9.8 Hz), 4.02 (1H, d, J=11.0 Hz), 4.15 (1H, d, J=11.4 Hz), 5.64-5.66 (2H, m), 5.99-6.01 (2H, m) ppm $^{13}$C-NMR (150 MHz in DMSO-d$_6$): δ=17.88, 17.90, 23.76, 27.79, 36.29, 37.08, 37.45, 40.47, 43.89, 65.79, 66.67, 125.67, 125.71, 135.78 (2C), 166.30, 166.43 ppm GC-MS (EI): (m/z)$^+$=41, 55, 69, 79, 91, 107, 121, 137, 193, 207, 292 (M$^+$)

Synthesis Example 3

Synthesis of (1-hydroxymethyl-1-cyclopentyl)methyl methacrylate (Monomer 3)

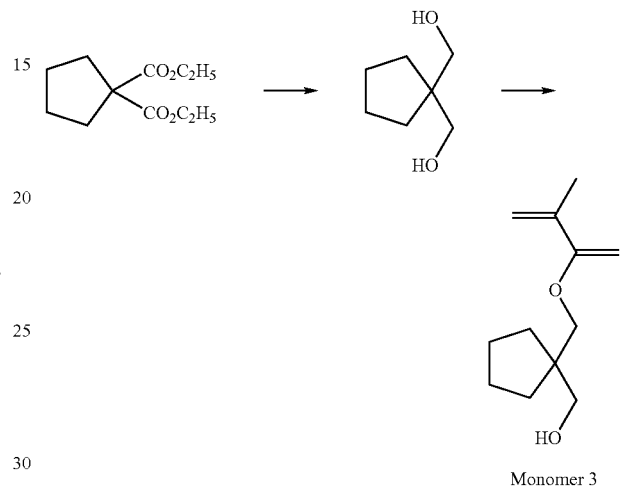

Monomer 3

In a nitrogen atmosphere, a mixture of 268 g of diethyl tetramethylenemalonate (which had been synthesized from diethyl malonate and 1,4-dibromobutane by a malonate synthesis standard technique) and 400 ml of tetrahydrofuran was added dropwise to a mixture of 80.0 g of lithium aluminum hydride (LiAlH$_4$) and 1,000 ml of tetrahydrofuran under ice cooling. The reaction mixture was stirred for 3 hours at room temperature, after which it was ice cooled again. To the reaction mixture which was kept below 30° C. and vigorously stirred, 80 ml of water, 80 ml of a 15% sodium hydroxide aqueous solution, and 240 ml of water were added dropwise in sequence. The resulting crystals were filtered off. The filtrate was concentrated in vacuum, obtaining 150 g (crude yield 92%) of a crude product. By the same procedure as in Synthesis Example 2-2 except that the crude product was used instead of norbornane-2,2-dimethanol, it was converted into a methacryloyl form, obtaining the target compound (yield 35%).

(1-hydroxymethyl-1-cyclopentyl)Methyl Methacrylate Colorless Liquid

IR (film): ν=3465, 2952, 2869, 1718, 1637, 1454, 1321, 1297, 1170, 1045, 1014 cm$^{-1}$ $^1$H-NMR (600 MHz in DMSO-d$_6$): δ=1.29-1.45 (4H, m), 1.51-1.57 (4H, m), 1.87 (3H, s), 3.24 (2H, d, J=5.5 Hz), 3.93 (2H, s), 4.67 (1H, t, J=5.5 Hz), 5.64 (1H, t-like, J=1.4 Hz), 6.00 (1H, s) ppm $^{13}$C-NMR (150 MHz in DMSO-d$_6$): δ=17.94, 25.05, 31.43, 47.29, 64.66, 67.79, 125.30, 136.11, 166.63 ppm GC-MS (EI): (m/z)$^+$=31, 41, 67, 82, 94, 112, 129, 150

GC-MS (CI, isobutanone): (m/z)$^+$=95, 113, 199 [(M+H)$^+$]

Synthesis Example 4

Synthesis of (3-hydroxy-2,2-dimethyl)propyl methacrylate (Monomer 4)

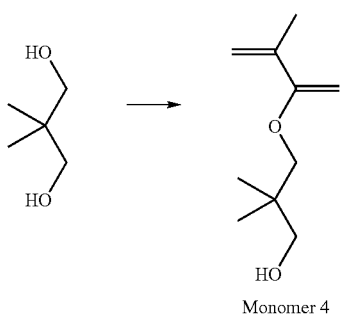

Monomer 4

By the same procedure as in Synthesis Example 2-2 except that 2,2-dimethyl-1,3-propane diol (or neopentane diol) was used instead of norbornane-2,2-dimethanol, the diol was converted into a methacryloyl form. There were obtained the target compound in a yield of 42% and a by-product, 3-methacryloyloxy-2,2-dimethylpropyl methacrylate in a yield of 29%.

(3-hydroxy-2,2-dimethyl)Propyl Methacrylate

Colorless Liquid

IR (film): ν=3467, 2962, 2875, 1718, 1639, 1475, 1456, 1402, 1369, 1322, 1299, 1170, 1054 cm$^{-1}$ $^1$H-NMR (600 MHz in DMSO-d$_6$): δ=0.84 (6H, s), 1.88 (3H, s), 3.19 (2H, d, J=5.5 Hz), 3.84 (2H, s), 4.62 (1H, t, J=5.5 Hz), 5.64 (1H, t-like, J=1.4 Hz), 6.02 (1H, s) ppm $^{13}$C-NMR (150 MHz in DMSO-d$_6$): δ=17.94, 21.35, 35.89, 66.77, 69.43, 125.34, 136.08, 166.47 ppm

3-methacryloyloxy-2,2-dimethylpropyl methacrylate colorless liquid

IR (film): ν=2967, 1722, 1639, 1475, 1454, 1402, 1371, 1321, 1295, 1159 cm$^{-1}$ $^1$H-NMR (600 MHz in DMSO-d$_6$): δ=0.96 (6H, s), 1.86 (6H, s-like), 3.93 (4H, s), 5.67 (1H, quint-like, J=1.4 Hz), 6.00 (1H, t, J=1.9 Hz) ppm $^{13}$C-NMR (150 MHz in DMSO-d$_6$): δ=17.88, 21.31, 34.73, 68.92, 125.73, 135.76, 166.23 ppm Polymers within the scope of the invention were synthesized according to the following formulation.

Synthesis Example 5-1

Synthesis of Polymer 1

In a nitrogen atmosphere, 5.3 g of (2-hydroxymethyl-2-adamantyl)methyl methacrylate, 6.6 g of 3-ethyl-3-exo-tetracyclo[4.4.0.1$^{2,5}$.1$^{7,10}$]dodecanyl methacrylate, 8.1 g of 4,8-dioxatricyclo[4.2.1.0$^{3,7}$]nonan-5-on-2-yl methacrylate, 0.53 g of 2,2'-azobisisobutyronitrile, and 0.19 g of 2-mercaptoethanol were dissolved in 5.5 g of PGMEA and 6.2 g of γ-butyrolactone. In a nitrogen atmosphere, with stirring, the solution was added dropwise to 16.4 g of PGMEA and 18.6 g of γ-butyrolactone at 80° C. over 4 hours. After the completion of dropwise addition, the polymerization solution was stirred at 80° C. for a further 2 hours, cooled to room temperature, and then added dropwise to 320 g of methanol. The solids precipitated were separated by filtration, washed twice with 120 g of methanol, and vacuum dried at 50° C. for 16 hours. There was obtained a polymer (designated Polymer 1) in white powder solid form in an amount of 45.5 g (yield 91%).

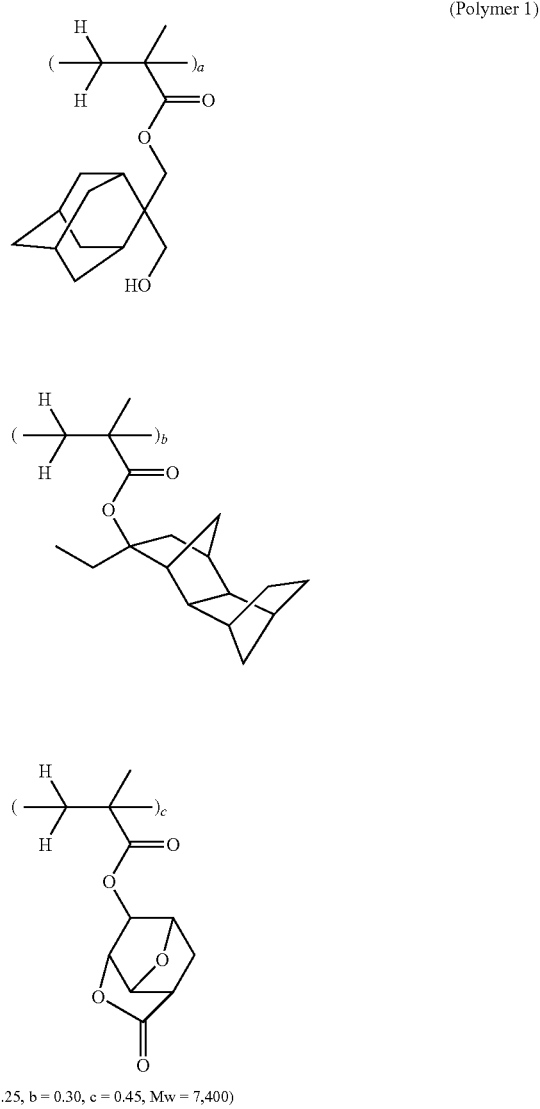

(Polymer 1)

(a = 0.25, b = 0.30, c = 0.45, Mw = 7,400)

Synthesis Examples 5-2 to 5-30 & Comparative Synthesis Examples 1-1 to 1-4

Synthesis of Polymer 2 to 34

Polymers 2 to 34 shown in Table 1 were synthesized by the same procedure as Synthesis Example 5-1 except that the type and proportion of monomers were changed, with their compositional proportion (in molar ratio) and Mw being shown in Table 1. The structure of the units in Table 1 is shown in Tables 2 to 5.

TABLE 1

|  | Resin | Unit 1 (ratio) | Unit 2 (ratio) | Unit 3 (ratio) | Unit 4 (ratio) | Mw |
|---|---|---|---|---|---|---|
| Synthesis Example 5-1 | Polymer 1 | H-1M (0.25) | A-1M (0.30) | B-3M (0.45) | — | 7,400 |
| Synthesis Example 5-2 | Polymer 2 | H-2M (0.25) | A-1M (0.30) | B-3M (0.45) | — | 7,200 |
| Synthesis Example 5-3 | Polymer 3 | H-3M (0.25) | A-1M (0.30) | B-3M (0.45) | — | 7,500 |
| Synthesis Example 5-4 | Polymer 4 | H-4M (0.25) | A-1M (0.30) | B-3M (0.45) | — | 7,900 |
| Synthesis Example 5-5 | Polymer 5 | H-1M (0.25) | A-1M (0.25) | B-3M (0.40) | C-3M (0.10) | 7,800 |
| Synthesis Example 5-6 | Polymer 6 | H-2M (0.25) | A-1M (0.25) | B-3M (0.40) | C-3M (0.10) | 6,900 |
| Synthesis Example 5-7 | Polymer 7 | H-3M (0.25) | A-1M (0.25) | B-3M (0.40) | C-3M (0.10) | 7,000 |
| Synthesis Example 5-8 | Polymer 8 | H-4M (0.25) | A-1M (0.25) | B-3M (0.40) | C-3M (0.10) | 6,700 |
| Synthesis Example 5-9 | Polymer 9 | H-1M (0.25) | A-1M (0.25) | B-3M (0.40) | C-1M (0.10) | 6,800 |
| Synthesis Example 5-10 | Polymer 10 | H-1M (0.25) | A-2M (0.40) | B-3M (0.35) | — | 6,500 |
| Synthesis Example 5-11 | Polymer 11 | H-1M (0.35) | A-3M (0.35) | B-5M (0.30) | — | 6,600 |
| Synthesis Example 5-12 | Polymer 12 | H-1M (0.30) | A-3M (0.35) | B-8M (0.35) | — | 6,800 |
| Synthesis Example 5-13 | Polymer 13 | H-1M (0.35) | A-3M (0.35) | B-7M (0.30) | — | 6,400 |
| Synthesis Example 5-14 | Polymer 14 | H-1M (0.25) | A-1M (0.25) | B-3M (0.40) | C-2M (0.10) | 6,900 |
| Synthesis Example 5-15 | Polymer 15 | H-1M (0.25) | A-1M (0.25) | B-3M (0.40) | C-4M (0.10) | 7,400 |
| Synthesis Example 5-16 | Polymer 16 | H-1M (0.25) | A-1M (0.25) | B-3M (0.40) | C-5M (0.10) | 6,600 |
| Synthesis Example 5-17 | Polymer 17 | H-1M (0.25) | A-5M (0.30) | B-3M (0.35) | C-1M (0.10) | 7,100 |
| Synthesis Example 5-18 | Polymer 18 | H-1M (0.25) | A-5M (0.30) | B-3M (0.35) | C-2M (0.10) | 6,700 |
| Synthesis Example 5-19 | Polymer 19 | H-1M (0.25) | A-1M (0.20) | B-3M (0.35) | A-5M (0.20) | 6,800 |
| Synthesis Example 5-20 | Polymer 20 | H-1M (0.25) | A-6M (0.25) | B-3M (0.40) | C-3M (0.10) | 6,800 |
| Synthesis Example 5-21 | Polymer 21 | H-1M (0.30) | A-1M (0.30) | B-9M (0.40) | — | 6,500 |
| Synthesis Example 5-22 | Polymer 22 | H-1M (0.25) | A-1M (0.35) | B-4M (0.40) | — | 6,600 |
| Synthesis Example 5-23 | Polymer 23 | H-1M (0.15) | A-1M (0.30) | B-9M (0.30) | B-6M (0.25) | 6,800 |
| Synthesis Example 5-24 | Polymer 24 | H-1M (0.10) | A-1M (0.50) | B-9M (0.30) | A-8M (0.10) | 6,400 |
| Synthesis Example 5-25 | Polymer 25 | H-1M (0.25) | A-4M (0.35) | B-3M (0.40) | — | 6,900 |
| Synthesis Example 5-26 | Polymer 26 | H-1M (0.25) | A-4M (0.35) | B-3M (0.30) | C-1M (0.10) | 7,400 |
| Synthesis Example 5-27 | Polymer 27 | H-1M (0.25) | A-4M (0.20) | B-3M (0.15) | A-7M (0.40) | 6,600 |
| Synthesis Example 5-28 | Polymer 28 | H-1M (0.25) | A-7M (0.30) | B-3M (0.45) | — | 7,100 |
| Synthesis Example 5-29 | Polymer 29 | H-1M (0.15) | A-1M (0.30) | B-3M (0.45) | B-1M (0.10) | 6,900 |
| Synthesis Example 5-30 | Polymer 30 | H-1M (0.15) | A-1M (0.30) | B-3M (0.45) | B-2M (0.10) | 6,800 |
| Comparative Synthesis Example 1-1 | Polymer 31 | A-1M (0.30) | B-1M (0.25) | B-3M (0.45) | — | 6,700 |
| Comparative Synthesis Example 1-2 | Polymer 32 | A-1M (0.25) | B-1M (0.25) | B-3M (0.40) | C-3M (0.10) | 7,000 |
| Comparative Synthesis Example 1-3 | Polymer 33 | A-1M (0.30) | B-2M (0.25) | B-3M (0.45) | — | 6,800 |
| Comparative Synthesis Example 1-4 | Polymer 34 | A-1M (0.25) | B-2M (0.25) | B-3M (0.40) | C-3M (0.10) | 6,800 |

TABLE 2

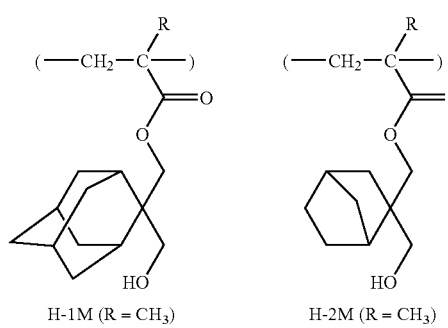

H-1M (R = CH$_3$)   H-2M (R = CH$_3$)

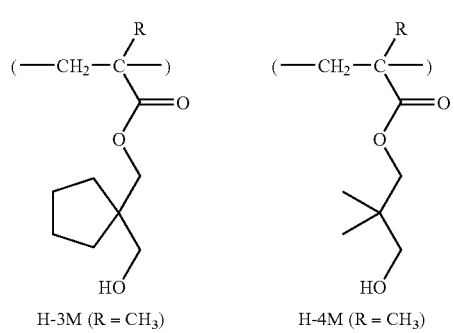

H-3M (R = CH$_3$)   H-4M (R = CH$_3$)

TABLE 3

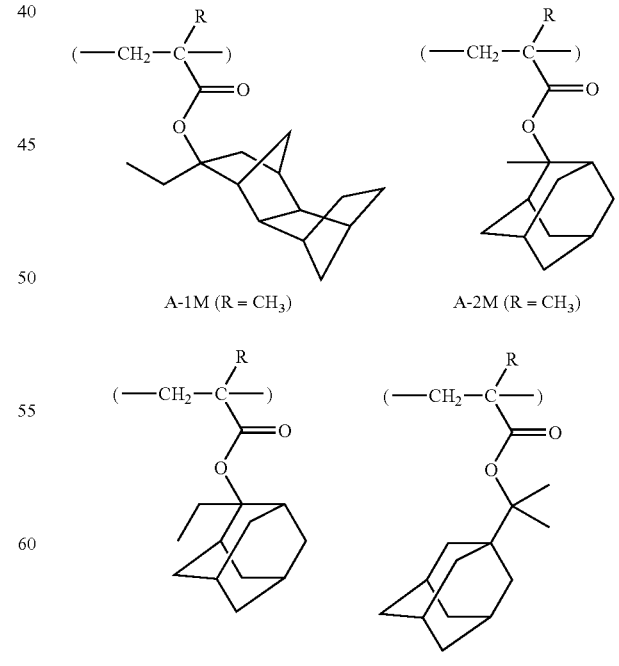

A-1M (R = CH$_3$)   A-2M (R = CH$_3$)

A-3M (R = CH$_3$)   A-4M (R = CH$_3$)

TABLE 3-continued
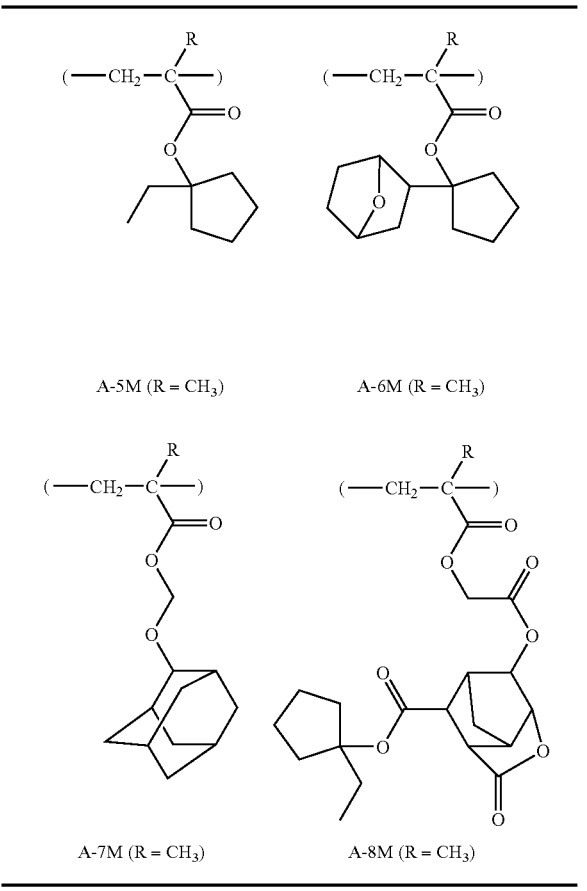
TABLE 4
TABLE 4-continued
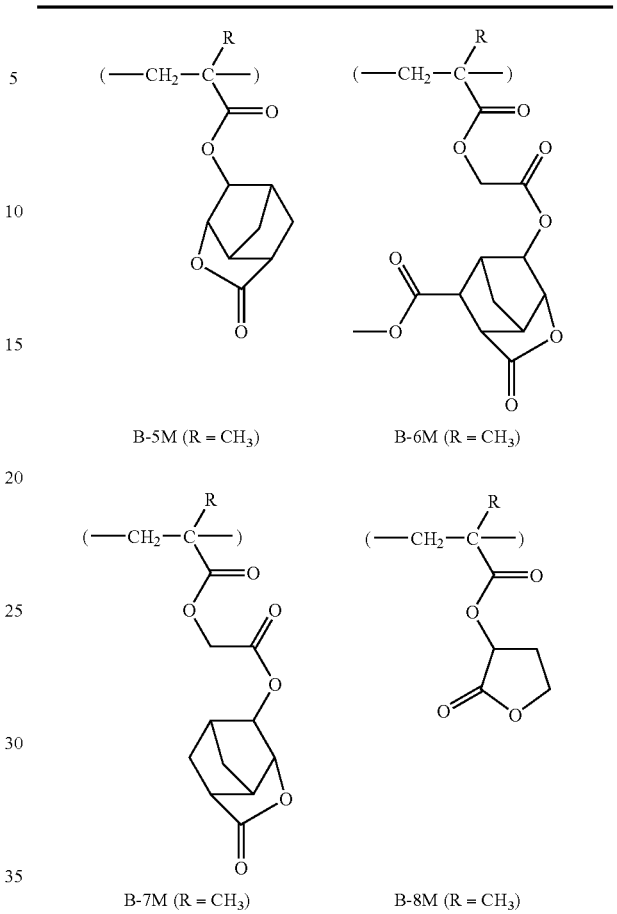
TABLE 5
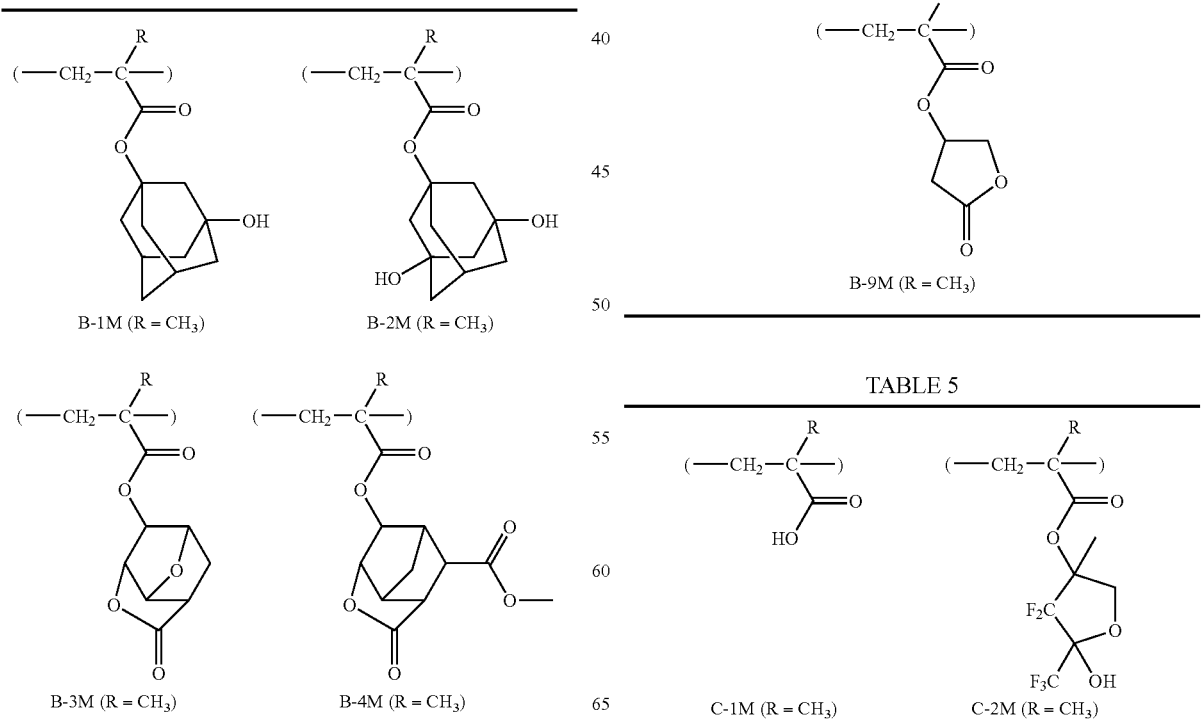

TABLE 5-continued

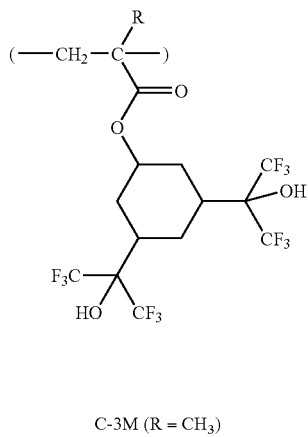

C-3M (R = CH₃)

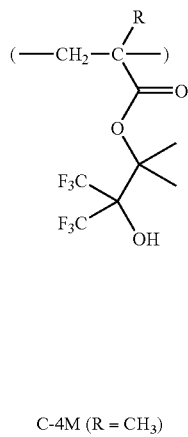

C-4M (R = CH₃)

TABLE 5-continued

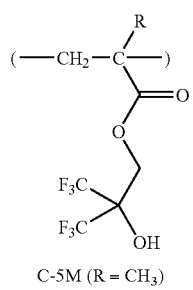

C-5M (R = CH₃)

Preparation of Resist Compositions

Examples 1-1 to 1-20 & Comparative Examples 1-1 to 1-4

Resist compositions were prepared by using inventive resins (Polymer 1 to 20) or comparative resins (Polymers 31 to 34) as the base resin, and dissolving the polymer, an acid generator (PAG), and a nitrogen-containing compound (Base) in a solvent mixture (PGMEA and CyHO) containing 0.01 wt % of surfactant KH-20 (Asahi Glass Co., Ltd.) in accordance with the recipe shown in Table 6. These compositions were each filtered through a Teflon® filter having a pore diameter 0.2 μm, thereby giving inventive resist solutions (R-01 to 20) and comparative resist solutions (R-21 to 24).

TABLE 6

| | Resist | Resin (pbw) | PAG (pbw) | Base (pbw) | Solvent 1 (pbw) | Solvent 2 (pbw) |
|---|---|---|---|---|---|---|
| Example 1-1 | R-01 | Polymer 1 (80) | PAG-1 (10.1) | Base-1 (1.47) | PGMEA (1,120) | CyHO (480) |
| Example 1-2 | R-02 | Polymer 2 (80) | PAG-1 (10.1) | Base-1 (1.47) | PGMEA (1,120) | CyHO (480) |
| Example 1-3 | R-03 | Polymer 3 (80) | PAG-1 (10.1) | Base-1 (1.47) | PGMEA (1,120) | CyHO (480) |
| Example 1-4 | R-04 | Polymer 4 (80) | PAG-1 (10.1) | Base-1 (1.47) | PGMEA (1,120) | CyHO (480) |
| Example 1-5 | R-05 | Polymer 5 (80) | PAG-1 (10.1) | Base-1 (1.47) | PGMEA (1,120) | CyHO (480) |
| Example 1-6 | R-06 | Polymer 6 (80) | PAG-1 (10.1) | Base-1 (1.47) | PGMEA (1,120) | CyHO (480) |
| Example 1-7 | R-07 | Polymer 7 (80) | PAG-1 (10.1) | Base-1 (1.47) | PGMEA (1,120) | CyHO (480) |
| Example 1-8 | R-08 | Polymer 8 (80) | PAG-1 (10.1) | Base-1 (1.47) | PGMEA (1,120) | CyHO (480) |
| Example 1-9 | R-09 | Polymer 9 (80) | PAG-1 (10.1) | Base-1 (1.47) | PGMEA (1,120) | CyHO (480) |
| Example 1-10 | R-10 | Polymer 10 (80) | PAG-1 (10.1) | Base-1 (1.47) | PGMEA (1,120) | CyHO (480) |
| Example 1-11 | R-11 | Polymer 11 (80) | PAG-1 (10.1) | Base-1 (1.47) | PGMEA (1,120) | CyHO (480) |
| Example 1-12 | R-12 | Polymer 12 (80) | PAG-1 (10.1) | Base-1 (1.47) | PGMEA (1,120) | CyHO (480) |
| Example 1-13 | R-13 | Polymer 13 (80) | PAG-1 (10.1) | Base-1 (1.47) | PGMEA (1,120) | CyHO (480) |
| Example 1-14 | R-14 | Polymer 14 (80) | PAG-1 (10.1) | Base-1 (1.47) | PGMEA (1,120) | CyHO (480) |
| Example 1-15 | R-15 | Polymer 15 (80) | PAG-1 (10.1) | Base-1 (1.47) | PGMEA (1,120) | CyHO (480) |
| Example 1-16 | R-16 | Polymer 16 (80) | PAG-1 (10.1) | Base-1 (1.47) | PGMEA (1,120) | CyHO (480) |
| Example 1-17 | R-17 | Polymer 17 (80) | PAG-1 (10.1) | Base-1 (1.47) | PGMEA (1,120) | CyHO (480) |
| Example 1-18 | R-18 | Polymer 18 (80) | PAG-1 (10.1) | Base-1 (1.47) | PGMEA (1,120) | CyHO (480) |
| Example 1-19 | R-19 | Polymer 19 (80) | PAG-1 (10.1) | Base-1 (1.47) | PGMEA (1,120) | CyHO (480) |
| Example 1-20 | R-20 | Polymer 20 (80) | PAG-1 (10.1) | Base-1 (1.47) | PGMEA (1,120) | CyHO (480) |
| Comparative Example 1-1 | R-21 | Polymer 31 (80) | PAG-1 (10.1) | Base-1 (1.47) | PGMEA (1,120) | CyHO (480) |
| Comparative Example 1-2 | R-22 | Polymer 32 (80) | PAG-1 (10.1) | Base-1 (1.47) | PGMEA (1,120) | CyHO (480) |
| Comparative Example 1-3 | R-23 | Polymer 33 (80) | PAG-1 (10.1) | Base-1 (1.47) | PGMEA (1,120) | CyHO (480) |
| Comparative Example 1-4 | R-24 | Polymer 34 (80) | PAG-1 (10.1) | Base-1 (1.47) | PGMEA (1,120) | CyHO (480) |

The acid generator, base and solvent shown in Table 6 have the following meanings.

PAG-1: triphenylsulfonium 2-(adamantane-1-carbonyloxy)-1,1,3,3,3-pentafluoropropane-1-sulfonate Base-1: 2-morpholinoethyl 2-[2-(2-methoxyethoxy)ethoxy]acetate PGMEA: propylene glycol monomethyl ether acetate CyHO: cyclohexanone

Evaluation of Resist Compositions

Examples 2-1 to 2-20 & Comparative Examples 2-1 to 2-4

Each of inventive resist compositions (R-01 to 20) and comparative resist compositions (R-21 to 24) in Example 1 was spin coated on a silicon wafer having an antireflective coating (ARC-29A, Nissan Chemical Co., Ltd.) of 78 nm thick and baked at 110° C. for 60 seconds, forming a resist film of 150 nm thick. The wafer was exposed by means of an ArF excimer laser stepper (Nikon Corp., NA 0.85), post-exposure baked (PEB) for 60 seconds, and puddle developed with a 2.38 wt % tetramethylammonium hydroxide aqueous solution for 30 seconds, forming a 1:1 line-and-space pattern. During the PEB, an optimum temperature for each resist composition was employed.

The wafer as developed was observed under a top-down scanning electron microscope (TDSEM). The optimum exposure (Eop) was defined as the exposure dose (mJ/cm$^2$) which provided a 1:1 resolution at the top and bottom of a 80-nm grouped line-and-space pattern. The maximum resolution of the resist was defined as the minimum line width (nm) of a line-and-space pattern that was resolved and separated at the optimum exposure, with smaller values indicating better resolution. For the evaluation of proximity bias or pattern density dependency, a 1:10 isolated line pattern with an on-mask size of 130 nm was formed at the optimum exposure and determined for an actual on-wafer size, which was reported as mask fidelity (on-wafer size, a larger size being better). For the evaluation of exposure latitude, an exposure dose tolerance which provided a pattern size of 80 nm±10% when the exposure dose was changed from the optimum was determined, and the tolerance value was divided by the optimum dose and expressed in percent. A greater value indicates a smaller performance change with a change of exposure dose, that is, better exposure latitude.

Table 7 tabulates the test results (Eop, maximum resolution, mask fidelity, and exposure latitude) of the inventive and comparative resist compositions.

TABLE 7

|  | Resist | PEB temp. | Eop | Maximum resolution | Mask fidelity | Exposure latitude |
|---|---|---|---|---|---|---|
| Example 2-1 | R-01 | 100° C. | 32.0 mJ/cm$^2$ | 65 nm | 80 nm | 14% |
| Example 2-2 | R-02 | 100° C. | 34.0 mJ/cm$^2$ | 65 nm | 78 nm | 13% |
| Example 2-3 | R-03 | 100° C. | 33.0 mJ/cm$^2$ | 70 nm | 75 nm | 13% |
| Example 2-4 | R-04 | 100° C. | 31.0 mJ/cm$^2$ | 70 nm | 75 nm | 12% |
| Example 2-5 | R-05 | 100° C. | 33.0 mJ/cm$^2$ | 65 nm | 80 nm | 14% |
| Example 2-6 | R-06 | 100° C. | 34.0 mJ/cm$^2$ | 65 nm | 75 nm | 13% |
| Example 2-7 | R-07 | 100° C. | 32.0 mJ/cm$^2$ | 70 nm | 75 nm | 13% |
| Example 2-8 | R-08 | 100° C. | 31.0 mJ/cm$^2$ | 65 nm | 70 nm | 12% |
| Example 2-9 | R-09 | 100° C. | 30.0 mJ/cm$^2$ | 70 nm | 80 nm | 14% |
| Example 2-10 | R-10 | 115° C. | 38.0 mJ/cm$^2$ | 70 nm | 75 nm | 13% |
| Example 2-11 | R-11 | 100° C. | 37.0 mJ/cm$^2$ | 65 nm | 75 nm | 13% |
| Example 2-12 | R-12 | 90° C. | 35.0 mJ/cm$^2$ | 65 nm | 70 nm | 12% |
| Example 2-13 | R-13 | 100° C. | 36.0 mJ/cm$^2$ | 70 nm | 75 nm | 13% |
| Example 2-14 | R-14 | 100° C. | 32.0 mJ/cm$^2$ | 65 nm | 70 nm | 12% |
| Example 2-15 | R-15 | 100° C. | 34.0 mJ/cm$^2$ | 65 nm | 75 nm | 13% |
| Example 2-16 | R-16 | 100° C. | 33.0 mJ/cm$^2$ | 70 nm | 70 nm | 12% |
| Example 2-17 | R-17 | 105° C. | 33.0 mJ/cm$^2$ | 65 nm | 75 nm | 13% |
| Example 2-18 | R-18 | 105° C. | 35.0 mJ/cm$^2$ | 65 nm | 70 nm | 12% |
| Example 2-19 | R-19 | 100° C. | 31.0 mJ/cm$^2$ | 70 nm | 80 nm | 14% |
| Example 2-20 | R-20 | 105° C. | 35.0 mJ/cm$^2$ | 65 nm | 70 nm | 12% |
| Comparative Example 2-1 | R-21 | 105° C. | 32.0 mJ/cm$^2$ | 75 nm | 60 nm | 10% |
| Comparative Example 2-2 | R-22 | 105° C. | 33.0 mJ/cm$^2$ | 75 nm | 60 nm | 10% |
| Comparative Example 2-3 | R-23 | 105° C. | 35.0 mJ/cm$^2$ | 80 nm | 65 nm | 11% |
| Comparative Example 2-4 | R-24 | 105° C. | 35.0 mJ/cm$^2$ | 80 nm | 65 nm | 11% |

It is seen from the results of Table 7 that the resist compositions within the scope of the invention display improved resolution when processed by ArF excimer laser lithography.

Japanese Patent Application No. 2008-069020 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A hydroxyl-containing monomer having the general formula (1):

wherein $R^1$ is hydrogen, fluorine, methyl or trifluoromethyl, $R^2$ and $R^3$ bond together to form a $C_3$-$C_{12}$ aliphatic hydrocarbon ring with the carbon atom to which they are attached.

2. The monomer of claim 1, wherein the aliphatic hydrocarbon ring that $R^2$ and $R^3$ form is selected from the group consisting of cyclopropane, cyclobutane, cyclopentane, cyclohexane, bicyclo[2,2,1]heptane, bicyclo[2.2.2]octane, tricyclo[5.2.1.0$^{2,6}$]decane, adamantane, tetracyclo[4.4.0.1$^{2,5}$.1$^{7,10}$]dodecane, fused rings containing at least one of the foregoing, substituted forms of the foregoing in which some hydrogen atoms are replaced by straight, branched or cyclic monovalent hydrocarbon groups, and the foregoing groups containing an unsaturated bond.

3. The monomer of claim 1, wherein the aliphatic hydrocarbon ring that $R^2$ and $R^3$ form is a bridged hydrocarbon ring.

4. The monomer of claim 1, which is selected from a monomer having a formula selected from the group consisting of:

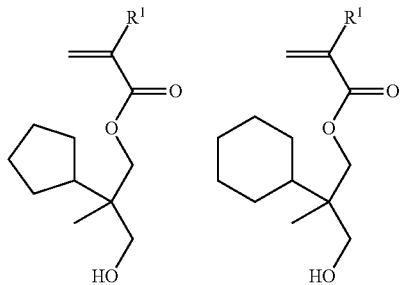

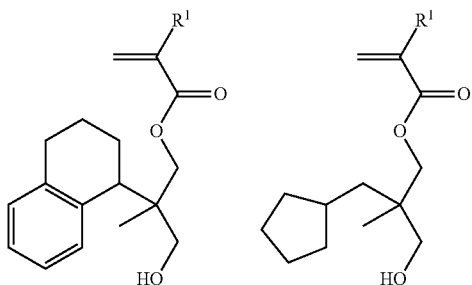

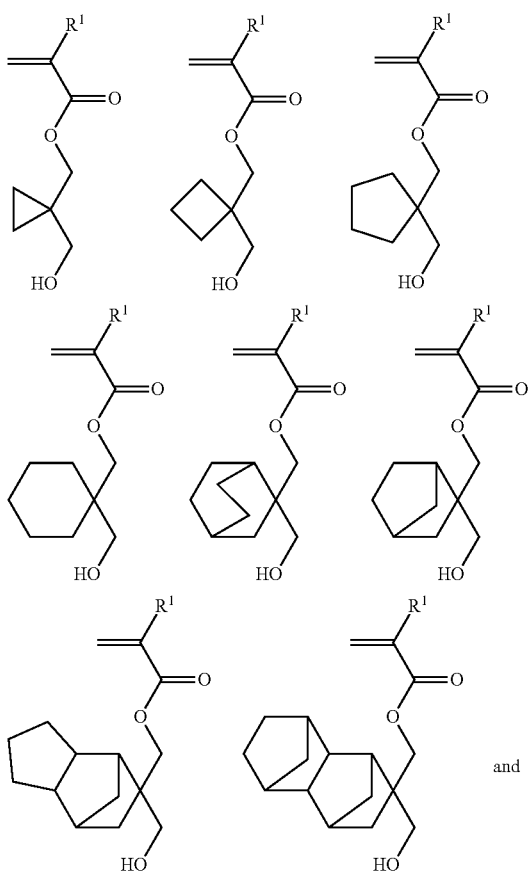

and

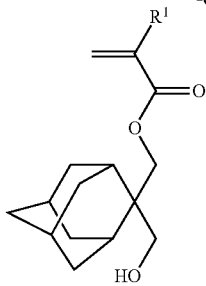

wherein $R^1$ is as defined above.

5. A polymer comprising recurring units derived from the hydroxyl-containing monomer of any one of claims 1, 2, 3 or 4, the recurring units being represented by the general formula (1a):

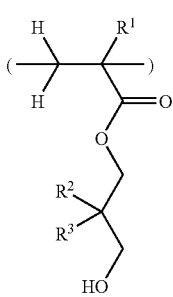

(1a)

wherein $R^1$ is hydrogen, fluorine, methyl or trifluoromethyl, and $R^2$ and $R^3$ bond together to form a $C_3$-$C_{12}$ aliphatic hydrocarbon ring with the carbon atom to which they are attached.

6. The polymer of claim 5, which further comprises recurring units of at least one type selected from the following general formulae (5a) to (8a):

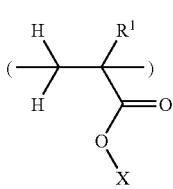

(5a)

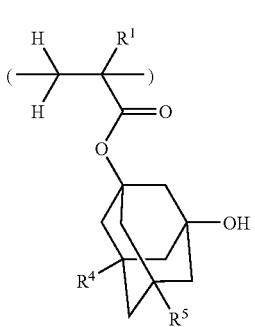

(6a)

-continued

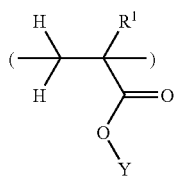
(7a)

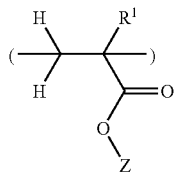
(8a)

wherein $R^1$ is as defined above, $R^4$ and $R^5$ are each independently hydrogen or hydroxyl, X denotes an acid labile group, Y denotes a substituent group having lactone structure, and Z denotes hydrogen, a $C_1$-$C_{15}$ fluoroalkyl group or a $C_1$-$C_{15}$ fluoroalcohol-containing substituent group.

7. A resist composition comprising the polymer of claim 6 as a base resin.

8. A process for forming a pattern, comprising the steps of applying the resist composition of claim 7 onto a substrate, heat treating, exposing to high-energy radiation or electron beam through a photomask, optionally heat treating, and developing with a developer.

9. A resist composition comprising the polymer of claim 5 as a basin resin

10. A process for forming a pattern, comprising the steps of applying the resist composition of claim 9 onto a substrate, heat treating, exposing to high-energy radiation or electron beam through a photomask, optionally heat treating, and developing with a developer.

* * * * *